(12) United States Patent
Galipeau et al.

(10) Patent No.: US 9,375,465 B2
(45) Date of Patent: Jun. 28, 2016

(54) CONJUGATES OF GM-CSF AND IL-7, COMPOSITIONS AND METHODS RELATED THERETO

(71) Applicants: EMORY UNIVERSITY, Atlanta, GA (US); CHILDREN'S HEALTHCARE OF ATLANTA, INC., Atlanta, GA (US)

(72) Inventors: Jacques Galipeau, Atlanta, GA (US); Hsiang-Chuan Hsieh, Atlanta, GA (US)

(73) Assignees: Emory University, Atlanta, GA (US); Children's Healthcare of Atlanta, Inc., Atlanta, GA (US)

( * ) Notice: Subject to any disclaimer, the term of this patent is extended or adjusted under 35 U.S.C. 154(b) by 0 days.

(21) Appl. No.: 14/355,673

(22) PCT Filed: Nov. 13, 2012

(86) PCT No.: PCT/US2012/064769
§ 371 (c)(1),
(2) Date: May 1, 2014

(87) PCT Pub. No.: WO2013/074489
PCT Pub. Date: May 23, 2013

(65) Prior Publication Data
US 2014/0369956 A1 Dec. 18, 2014

Related U.S. Application Data

(60) Provisional application No. 61/559,355, filed on Nov. 14, 2011.

(51) Int. Cl.
| | | |
|---|---|---|
| *A61K 38/19* | (2006.01) | |
| *A61K 39/00* | (2006.01) | |
| *C07K 14/535* | (2006.01) | |
| *C07K 14/54* | (2006.01) | |
| *A61K 39/39* | (2006.01) | |
| *A61K 35/14* | (2015.01) | |
| *A61K 38/00* | (2006.01) | |

(52) U.S. Cl.
CPC ............ *A61K 39/0005* (2013.01); *A61K 35/14* (2013.01); *A61K 39/0011* (2013.01); *A61K 39/39* (2013.01); *C07K 14/535* (2013.01); *C07K 14/5418* (2013.01); *A61K 38/00* (2013.01); *A61K 2039/5158* (2013.01); *A61K 2039/55522* (2013.01); *A61K 2039/55527* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 7,217,421 B1 | 5/2007 | McArthur | |
| 7,323,549 B2 | 1/2008 | Lauder | |
| 7,960,514 B2 | 6/2011 | Lauder | |
| 2005/0053579 A1* | 3/2005 | Galipeau et al. | 424/85.1 |
| 2010/0021421 A1 | 1/2010 | Galipeau | |
| 2011/0124552 A1 | 5/2011 | Galipeau | |
| 2011/0150828 A1 | 6/2011 | Galipeau | |
| 2012/0164101 A1 | 6/2012 | Galipeau | |
| 2014/0348781 A1 | 11/2014 | Galipeau | |

FOREIGN PATENT DOCUMENTS

| | | |
|---|---|---|
| WO | 03/035105 | 5/2003 |
| WO | 2005/014642 | 2/2005 |
| WO | 2008/014612 | 2/2008 |
| WO | 2010/020766 | 2/2010 |
| WO | 2014/066443 | 5/2014 |

OTHER PUBLICATIONS

Li et al. Recombinant IL-7 enhances the potency of GM-CSF-secreting tumor cell immunotherapy. Clin Immunol. May 2007;123(2):155-65.*

Williams et al. GM-CSF-based fusion cytokines as ligands for immune modulation.. J Immunol. May 15, 2011;186(10): 5527-32.*

Hsieh et al. In vivo administration of a novel synthetic GMCSF and IL7 fusion cytokine (GIF17) leads to transient thymic hyperplasia by driving double-negative (ON), singlepositive CD8 (SPCD8) and gamma-delta thymocyte proliferation, Journal of Imnmology, 2012, 188, 165.7.

Williams et al. GMCSF Interleukin fusion cytokhles induce novel immune effectors that can serve as biopharmaceuticals for treatment of autoimmunity and cancer J Intern Med, 2011, 269: 74-84.

Li et al., Recombinant IL-7 enhances the potency of GM-CSF-secreting tumor cell immunotherapy, Clinical Immunology, 2007, 123, 155-165.

Extended European Search Report 2015.

Pellegrini et al.,Adjuvant IL-7 antagonizes multiple cellular and molecular inhibitory networks to enhance immunotherapies Nature Medicine, 2009, 15, 528-536.

(Continued)

*Primary Examiner* — Dong Jiang
(74) *Attorney, Agent, or Firm* — Emory Patent Group

(57) ABSTRACT

In certain embodiments, this disclosure relates to conjugates comprising GM-CSF and IL-7 and uses related thereto, e.g., enhancing the adaptive immune system. Typically the GM-CSF and IL-7 are connected by a polymer linker, e.g., polypeptide. In certain embodiments, the disclosure relates to nucleic acids encoding these polypeptide conjugates, vectors comprising nucleic acid encoding polypeptide conjugates, and protein expression systems comprising these vectors such as infectious viral particles and host cells comprising such a nucleic acids.

2 Claims, 22 Drawing Sheets

(56) References Cited

OTHER PUBLICATIONS

Schroten-Loef et al., A prostate cancer vaccine comprising whole cells secreting IL-7, effective against subcutaneous challenge, requires local GM-CSF for intra-prostatic efficacy, Cancer Immunol, Immunother, 2009, 58:373-381.

Williams and Park, Hematopoietic Effects of a Granulocyte-Macrophage Colony-Stimulating Factor/Interleukin-3 Fusion Protein, Cancer, 1991, 67(10 Suppl):2705-7.

Jacobsen et al. IL-7 stimulates CSF-induced proliferation of murine bone marrow macrophages and Mac-1+ myeloid progenitors in vitro. J Immunol. 1994, 153(1):270-6.

* cited by examiner

A.

mGIFT7

MWLQNLLFLGIVVYSLSAPTRSPITVTRPWKHVEAIK
EALNLLDDMPVTLNEEVEVVSNEFSFKKLTCVQTRLK
IFEQGLRGNFTKLKGALNMTASYYQTYCPPTPETDCE
TQVTTYADFIDSLKTFLT*SPVGGAN*MFHVSFRYIFGIP
PLILVLLPVTSSECHIKDKEGKAYESVLMISIDELDKM
TGTDSNCPNNEPNFFRKHVCDDTKEAAFLNRAARKL
KQFLKMNISEEFNVHLLTVSQGTQTLVNCTSKEEKNV
KEQKKNDACFLKRLLREIKTCWNKILKGSI hGIFT7

MWLQSLLLLGTVACSISAPARSPSPSTQPWEHVNAIQ
EARRLLNLSRDTAAEMNETVEVISEMFDLQEPTCLQT
RLELYKQGLRGSLTKLKGPLTMMASHYKQHCPPTPE
TSCATQIITFESFKENLKDFLLVIPFDCWEPVQE*SPVN*
MFHVSFRYIFGLPPLILVLLPVASSDCDIEGKDGKQYE
SVLMVSIDQLLDSMKEIGSNCLNNEFNFFKRHICDAN
KEGMFLFRAARKLRQFLKMNSTGDFDLHLLKVSEGT
TILLNCTGQVKGRKPAALGEAQPTKSLEENKSLKEQK
KLNDLCFLKRLLQEIKTCWNKILMGTKEH

B.

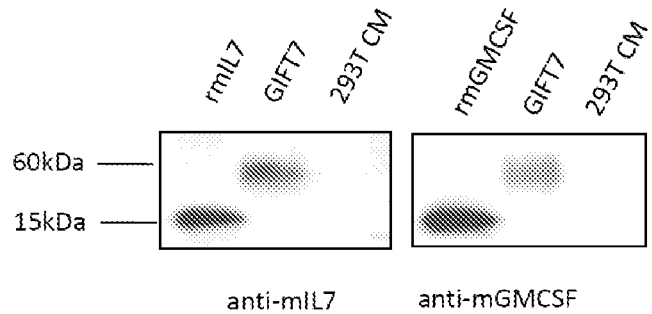

A.
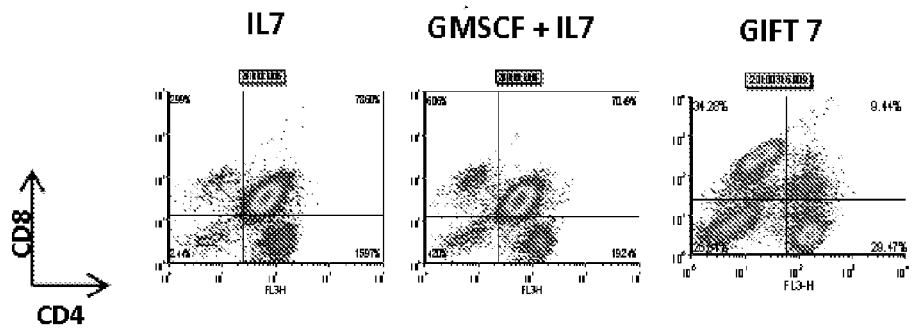
B.
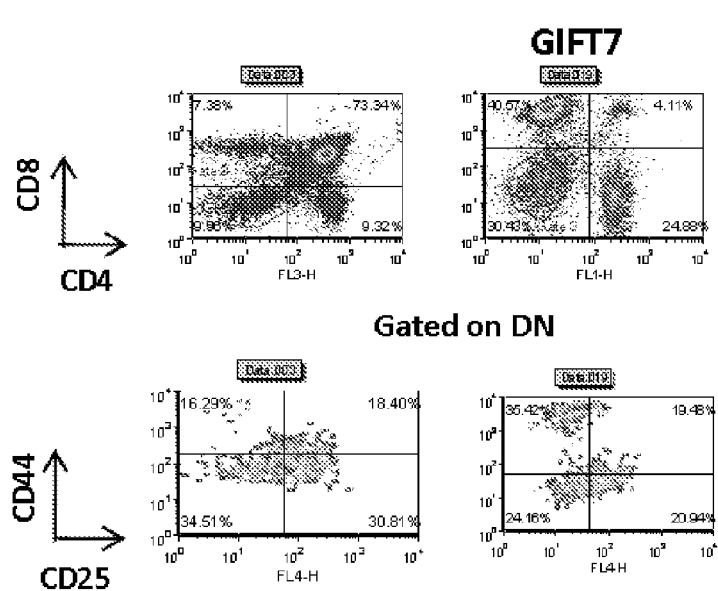
Gated on DN
C.
mice thymic DN
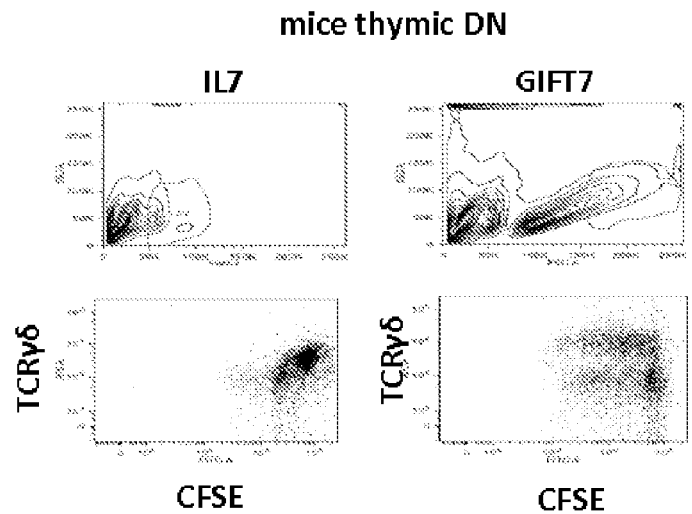
FIG 4-1

CONJUGATES OF GM-CSF AND IL-7, COMPOSITIONS AND METHODS RELATED THERETO

CROSS-REFERENCE TO RELATED APPLICATIONS

This application claims priority to U.S. Provisional Application No. 61/559,355 filed Nov. 14, 2011, hereby incorporated by reference in its entirety.

BACKGROUND

Although many viruses are cleared by the immune system, certain retroviruses, like HIV, evade the immune system, lie dormant, spread, and cause chronic infections. The World Health Organization estimates that AIDS has killed more than 25 million people since it was first recognized. In 2007, there were 2.7 million new HIV infections and 2 million HIV-related deaths. Anti-retroviral drugs are medications for the treatment of infection by retroviruses. When several antiviral agents are taken in combination with a retroviral drug, the approach is known as highly active antiretroviral therapy (HAART). Although HAART may improve symptoms associated with infection, there is currently no cure for HIV. HAART can also have serious side-effects. Regimens can be complicated, requiring patients to take several pills at various times during the day. If patients miss a dose, drug resistance can develop. Therefore, there remains a need for improved antiviral therapies. In particular, there remains a need for antiviral therapies with reduced toxicity and improved efficacy over existing treatments.

Analogous to virus, cancer is thought to occur as a result of an immune system that is not properly removing uncontrolled proliferating cancer cells. Stimulating the immune system to recognize and eliminate cancerous cells has become a promising strategy for therapeutic treatments. For example, Provenge™ is a FDA-approved autologous cellular immunotherapy treatment. Peripheral blood leukocytes of a subject are harvested via leukapheresis. These enriched monocytes are incubated prostatic acid phosphatase (PAP) conjugated to cytokine granulocyte macrophage colony stimulating factor (PAP-GM-CSF). GM-CSF is thought to direct the target antigen to receptors on DC precursors, which then present PAP on their cell surface in a context sufficient to activate T cells for the cells that express PAP. Activated, PAP presenting DCs are administered to the subject to elicit an immune response retarding cancer growth. This strategy requires isolation and expansion of cells of the subject, and typically treatment does not entirely clear the subject of cancer or tumors. Thus, there is a need to identify improved methods.

Li et al., Clinical Immunology (2007) 123, 155-165, reported that recombinant IL-7 enhances the potency of GM-CSF-secreting tumor cell immunotherapy. Pellegrini et al., Nature Medicine, 2009, 15, 528-536, reported that when combined with a GM-CSF-secreting tumor cell immunotherapy, IL-7 prolonged the survival of tumor-bearing mice. Schroten-Loef et al., Cancer Immunol Immunother, (2009), 58:373-381, disclose a prostate cancer vaccine comprising whole cells secreting IL-7.

Williams and Park, Cancer, 1991, 67(10 Suppl):2705-7, disclose a fusion protein of the granulocyte-macrophage colony-stimulating factor (GM-CSF) and interleukin-3 (IL-3). See also WO 2005/0053579, WO 2005/026820, WO 2008/0014612, and U.S. Pat. Nos. 7,323,549 and 7,217,421.

SUMMARY

In certain embodiments, this disclosure relates to conjugates comprising a polypeptide of GM-CSF and a polypeptide IL-7. Typically the GM-CSF and IL-7 are connected by a polymer linker, e.g., polypeptide. In certain embodiments, the disclosure relates to nucleic acids encoding these polypeptide conjugates, vectors comprising nucleic acid encoding polypeptide conjugates, and protein expression systems comprising these vectors such as infectious viral particles and host cells comprising such a nucleic acids.

In certain embodiments, the disclosure relates to pharmaceutical compositions comprising conjugates and vectors disclosed herein and a pharmaceutically acceptable excipient. In certain embodiments, the disclosure relates to vaccines comprising conjugates and vectors disclosed herein and an antigen and optionally an adjuvant. Typically, the antigen is live attenuated virus, killed virus, a virus-like particle, virosome, cancerous cell, lipid bilayer structure with a surface antigen, viral protein or glycoprotein, bacteria, or bacterial antigen, or tumor associated antigen. In certain embodiments, the antigen is conjugated to a dendritic cell marker.

In certain embodiments, the disclosure relates to methods of treating or preventing a viral, bacterial, or parasitic infection comprising administering an effective amount of a pharmaceutical composition comprising a conjugate or vector disclosed herein optionally in combination with an antigen and optionally an adjuvant. In certain embodiments, the subject is at risk or, exhibiting symptoms of, or diagnosed with a viral infection, such as a chronic viral infection.

In certain embodiments, the disclosure relates to methods of treating or preventing a viral infection comprising administering an effective amount of a vaccine comprising a conjugate disclosed herein to a subject in need thereof.

In certain embodiments, the subject is diagnosed with influenza A virus including subtype H1N1, influenza B virus, influenza C virus, rotavirus A, rotavirus B, rotavirus C, rotavirus D, rotavirus E, SARS coronavirus, human adenovirus types (HAdV-1 to 55), human papillomavirus (HPV) Types 16, 18, 31, 33, 35, 39, 45, 51, 52, 56, 58, and 59, parvovirus B19, molluscum contagiosum virus, JC virus (JCV), BK virus, Merkel cell polyomavirus, coxsackie A virus, norovirus, Rubella virus, lymphocytic choriomeningitis virus (LCMV), yellow fever virus, measles virus, mumps virus, respiratory syncytial virus, rinderpest virus, California encephalitis virus, hantavirus, rabies virus, ebola virus, marburg virus, herpes simplex virus-1 (HSV-1), herpes simplex virus-2 (HSV-2), varicella zoster virus (VZV), Epstein-Barr virus (EBV), cytomegalovirus (CMV), herpes lymphotropic virus, roseolovirus, or Kaposi's sarcoma-associated herpesvirus, hepatitis A, hepatitis B, hepatitis C, hepatitis D, hepatitis E or human immunodeficiency virus (HIV).

In certain embodiments, the disclosure relates to administering a conjugate or vector disclosed herein in combination with another antiviral agent such as abacavir, acyclovir, acyclovir, adefovir, amantadine, amprenavir, ampligen, arbidol, atazanavir, atripla, boceprevir, cidofovir, combivir, darunavir, delavirdine, didanosine, docosanol, edoxudine, efavirenz, emtricitabine, enfuvirtide, entecavir, famciclovir, fomivirsen, fosamprenavir, foscarnet, fosfonet, ganciclovir, ibacitabine, immunovir, idoxuridine, imiquimod, indinavir, inosine, interferon type III, interferon type II, interferon type I, lamivudine, lopinavir, loviride, maraviroc, moroxydine, methisazone, nelfinavir, nevirapine, nexavir, oseltamivir, peginterferon alfa-2a, penciclovir, peramivir, pleconaril, podophyllotoxin, raltegravir, ribavirin, rimantadine, ritonavir, pyramidine, saquinavir, stavudine, tenofovir, tenofovir disoproxil, tipranavir, trifluridine, trizivir, tromantadine, truvada, valaciclovir, valganciclovir, vicriviroc, vidarabine, viramidine zalcitabine, zanamivir, and/or zidovudine.

In certain embodiments, the disclosure relates to methods of treating or preventing cancer comprising administering a pharmaceutical composition comprising a conjugate or vector disclosed herein to a subject in need thereof.

In certain embodiments, the disclosure relates to methods of treating or preventing cancer comprising administering autologous blood cells activated with a cancer antigen conjugated to GM-CSF in combination with a conjugate disclosed herein to a subject in need thereof.

In certain embodiments, the disclosure relates to methods of activating peripheral blood cells comprising mixing peripheral blood cells with a conjugate disclosed herein comprising a tumor associated antigen/cancer marker under conditions such that increase expression of CD54 occurs. In certain embodiments, the disclosure relates to product produced by mixing peripheral blood cells and with a conjugate disclosed herein under conditions such that increase expression of CD54 occurs. In certain embodiments, the disclosure relates to methods of treating or preventing cancer comprising administering an effective amount of a product made by mixing peripheral blood cells with a conjugate disclosed herein to subject from whom the peripheral blood cells were obtained.

In some embodiments, the disclosure relates to a method of treating or preventing cancer comprising by administering a pharmaceutical composition comprising conjugates or vector disclosed herein to a subject diagnosed with, exhibiting symptoms of, or at risk of cancer wherein the cancer is a hematological malignancy such as a leukemia or lymphoma, acute lymphoblastic leukemia (ALL), acute myelogenous leukemia (AML), chronic lymphocytic leukemia (CLL), small lymphocytic lymphoma (SLL), chronic myelogenous leukemia, acute monocytic leukemia (AMOL), Hodgkin's lymphomas, and non-Hodgkin's lymphomas such as Burkitt lymphoma, B-cell lymphoma and multiple myeloma. Other contemplated cancers include cervical, ovarian, colon, breast, gastric, lung, skin, ovarian, pancreatic, prostate, head, neck, and renal cancer.

Within any of the cancer management methods disclosed herein, the conjugate or vector may be administered in combination with an anti-cancer agent such as gefitinib, erlotinib, docetaxel, cis-platin, 5-fluorouracil, gemcitabine, tegafur, raltitrexed, methotrexate, cytosine arabinoside, hydroxyurea, adriamycin, bleomycin, doxorubicin, daunomycin, epirubicin, idarubicin, mitomycin-C, dactinomycin and mithramycin, vincristine, vinblastine, vindesine, vinorelbine taxol, taxotere, etoposide, teniposide, amsacrine, topotecan, camptothecin, bortezomib, anagrelide, tamoxifen, toremifene, raloxifene, droloxifene, iodoxyfene, fulvestrant, bicalutamide, flutamide, nilutamide, cyproterone, goserelin, leuprorelin, buserelin, megestrol, anastrozole, letrozole, vorazole, exemestane, finasteride, marimastat, trastuzumab, cetuximab, dasatinib, imatinib, bevacizumab, combretastatin, thalidomide, and/or lenalidomide or combinations thereof.

In certain embodiments, the disclosure relates to gene therapies comprising administering vectors comprising nucleic acid encoding conjugates disclosed herein to a subject in need thereof.

In certain embodiments, the disclosure contemplates incorporating conjugates disclosed herein into the surfaces of particles, e.g., cells, liposomes, micelles, vesicles, bilayer structures, virosomes, and virus-like particles. The conjugates may be linked to lipophilic moieties, e.g., fatty acids and GPI. In one example, the disclosure contemplates a GPI anchored conjugate comprising GPI, GM-CSF, IL-7, and optionally an antigen, adjuvant, or other polypeptide. It is contemplated that these particles may contain other surface polypeptides, antigens and co-stimulatory molecules such as B7-1, B7-2, ICAM-1, and/or IL-2. It is contemplated that these particles may be used in all the applications conjugates disclosed herein are mentioned.

Within certain embodiments, any of the conjugates disclosed herein may be further conjugated to an adjuvant, cytokine, co-stimulatory molecule, antigen, protein, or glycoprotein. In certain embodiments, the antigen is a viral protein or a cancer marker.

In certain embodiments, the cancer marker is selected from PAP (prostatic acid phosphatase), prostate-specific antigen (PSA), (PSMA) prostate-specific membrane antigen, early prostate cancer antigen-2 (EPCA-2), AKAP-4 (A kinase [PRKA] anchor protein 4), NGEP (new gene expressed in prostate), PSCA (prostate stem cell antigen), STEAP (six-transmembrane epithelial antigen of the prostate), MUC 1 (mucin 1), HER-2, BCL-2, MAGE antigens such as CT7, MAGE-A3 and MAGE-A4, ERK5, G-protein coupled estrogen receptor 1, CA15-3, CA19-9, CA 72-4, CA-125, carcinoembryonic antigen, CD20, CD31, CD34, PTPRC(CD45), CD99, CD117, melanoma-associated antigen (TA-90), peripheral myelin protein 22 (PMP22), epithelial membrane proteins (EMP-1, -2, and -3), HMB-45 antigen, MART-1 (Melan-A), S100A1, and S100B or fragments or mutated forms thereof.

In certain embodiments, the viral antigen is selected from an influenza virus hemagglutinin and neuraminidase; cytomegalovirus glycoprotein gB, p28, p38, p50, p52, p65, and p150; *Borrelia* p41; HIV nef, integrase, gag, protease, tat, env, p31, p17, p24, p31, p55, p66, gp32, gp36, gp39, gp41, gp120, and gp160; SIV p55; HBV core, surface antigen, and australian antigen; HCV core nucleocapsid, NS3, NS4, and NS5; Dengue env and NS1; EBV early antigen, p18, p23, gp125, nuclear antigen (EBNA)-1, EBNA-2, EBNA-3A, EBNA-3B, EBNA-3C, EBNA-leader protein (EBNA-LP), latent membrane proteins (LMP)-1, LMP-2A and LMP-2B; and herpes simplex virus gD and gG or fragments or mutated forms thereof.

In certain embodiments, the adjuvant or cytokine is selected from IL-2, IL-12, IL-15, IL-18, IL-21, IL-27, IL-31, IFN-alpha, flagellin, unmethylated, CpG oligonucleotide, lipopolysaccharides, lipid A, and heat stable antigen (HSA).

DETAILED DESCRIPTION

GM-CSF-IL-7 Fusokine (GIFT7)

Figure 2A:
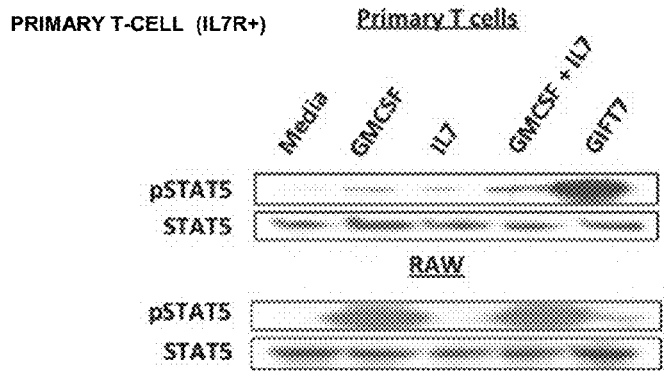
FIG. 2 shows GIFT7-mediated biochemical and cellular effects on lymphoid cells. (A) GIFT7-mediated STAT5 phosphorylation of primary T cells and RAW247.6 cells upon stimulation. (B) $1.25 \times 10^5$ per well of CD3/CD28 pre-activated T cells in 96 well plates were stimulated with GIFT7, GM-CSF, IL-7, GM-CSF+IL-7 or media alone for 6 days. Cell viability and proliferation were assessed by trypa blue exclusion and CFSE dilution, respectively. *$P<0.05$ (C) Percent apoptotic cells were assessed by PI/Annexin V co-staining.
Figure 2B:
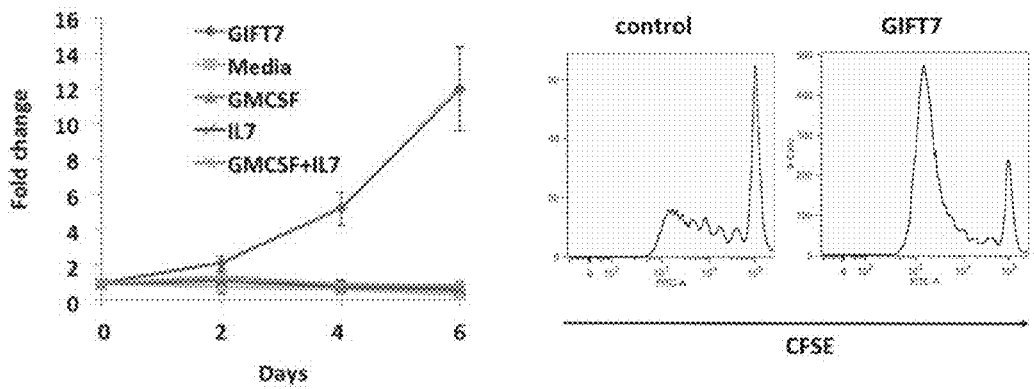
Figure 2C:
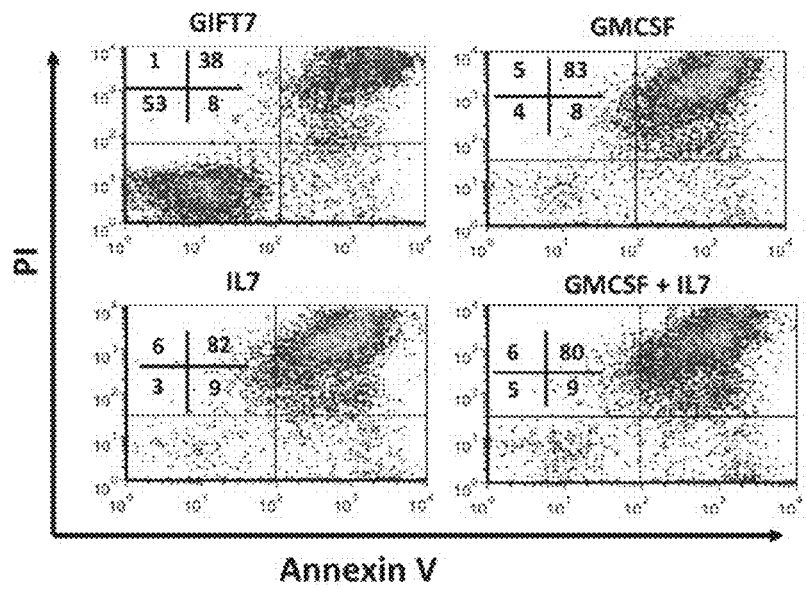
Figure 3:
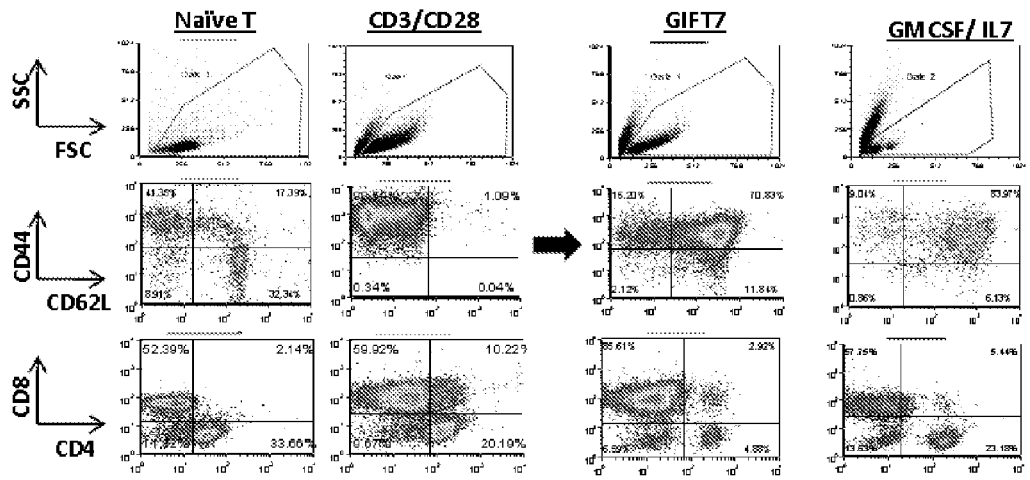
FIG. 3 shows GIFT7-mediated conversion of CD8 T cells. (A, B) Immunophenotype of GIFT7-treated pre-activated T cells. Ex vivo manipulated T cells were stained with the indicated antibodies and surface expression was analyzed by FCAS. (C) IFNγ production from responding GIFT7OT1-CD8 T cells, reactivated in vitro by OVA-pulsed macrophages in the presence or absence of TGF-β. Results represent the mean value of three independent experiments+/−SD; *P<0.05 (D) 5×10⁶ GIFT7OT1-CD8 T cells were administered into WT naïve pep-boy mice, which were subsequently injected with recombinant OVA after 21 days. 7 days later, splenic content was analyzed for the frequency of exogenous OT1 cells (E) Two doses of 10×10⁶ GIFT7OT1-CD8 T cells were given in vivo to mice with palpable EG7.
Figure 1:
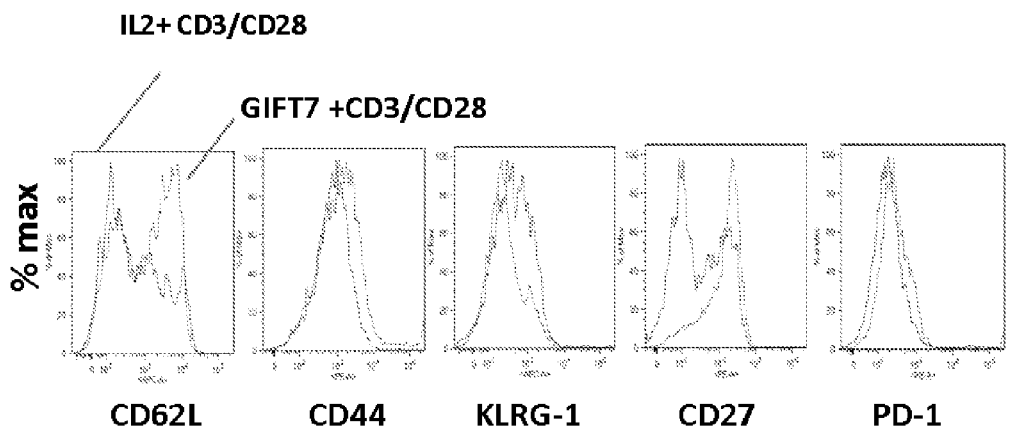
FIG. 1 shows the construction of a GM-CSF and IL-7 conjugate referred to as GIFT7—linker italicized. (A) Amino acid sequence of mGIFT7 (SEQ ID NO:2) and hGIFT7 (SEQ ID NO:1). Schematic representation of the fusion GIFT7 showing GM-CSF at the N-terminus linked to C-terminal domain IL-7 by peptide linker (B) Denatured immunoblotting using supernatant derived from GIFT7 or mock-transfected 293 cells. rGM-CSF or rIL-7 were used as controls. The blot was probed with polyclonal goat anti-IL-7 and anti-GM-CSF antibody to detect fusion protein secretion.

Interleukin-7 (IL-7) is a γ-chain cytokine that plays a role in T cell development and homeostasis by signaling through its cognate receptor, IL-7R or CD127, and inducing T cell survival and/or proliferation. Disclosed herein is a conjugate protein comprising GM-CSF linked to IL-7 by a peptide linker, and this fusion cytokine (fusokine) transgene can be expressed and secreted by mammalian cell lines in a manner that is recognized by both anti-GM-CSF and anti-IL-7 antisera (FIG. 1). This fusokine is very potent in mediating rejection of cancer by immune competent recipients. GIFT7 has effects on antigen experienced CD8 T-cells, converting them into Central Memory Phenotype, GIFT7 CD8 (FIG. 3). It is important to note that a GM-CSF/IL3 fusion does not display gain of function, i.e., a GM-CSF/interleukin fusion will not necessarily acquire this function. Also, the gain of function seen with GM-CSF/IL-2 fusion affected NK cells solely whilst GIFT7 specifically enhances the biology of memory T-cells, double negative thymocytes and expands CD4 t-cells as well.

Figures 2, 3:
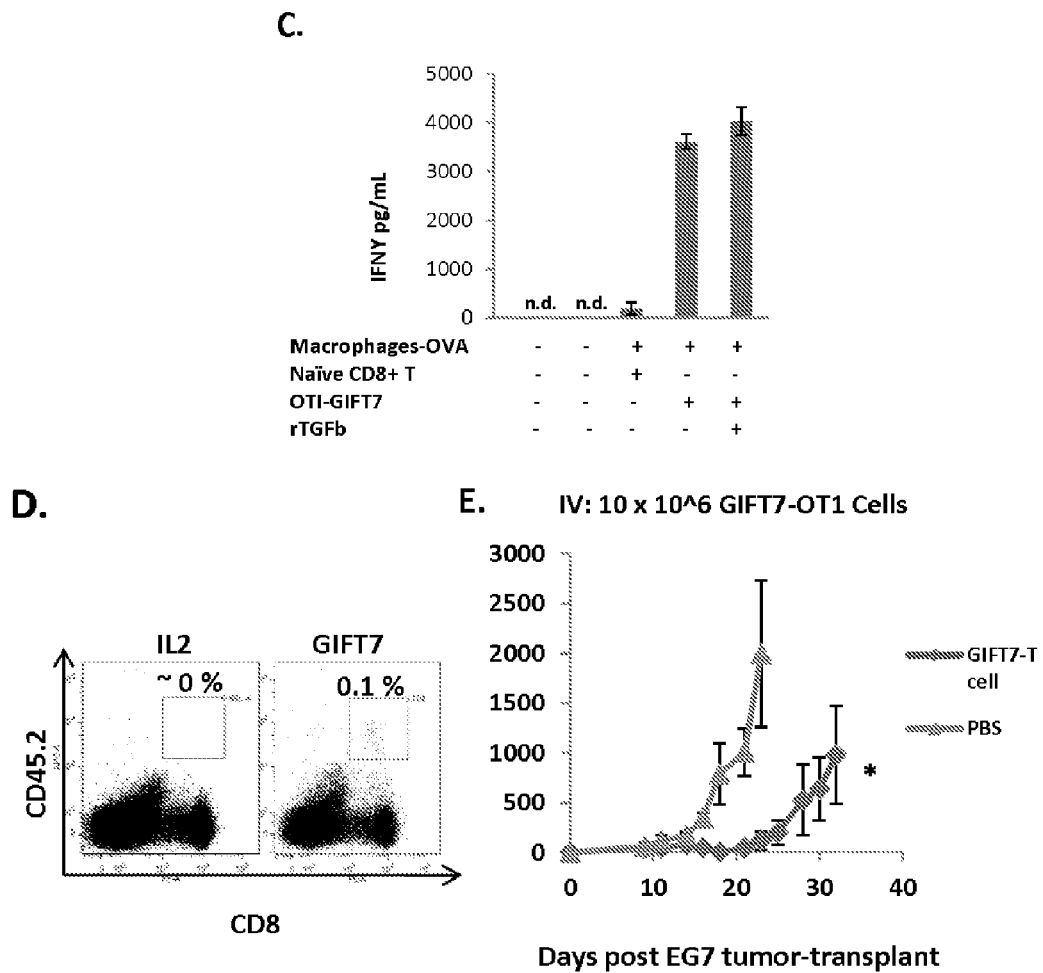
Figures 2, 4:
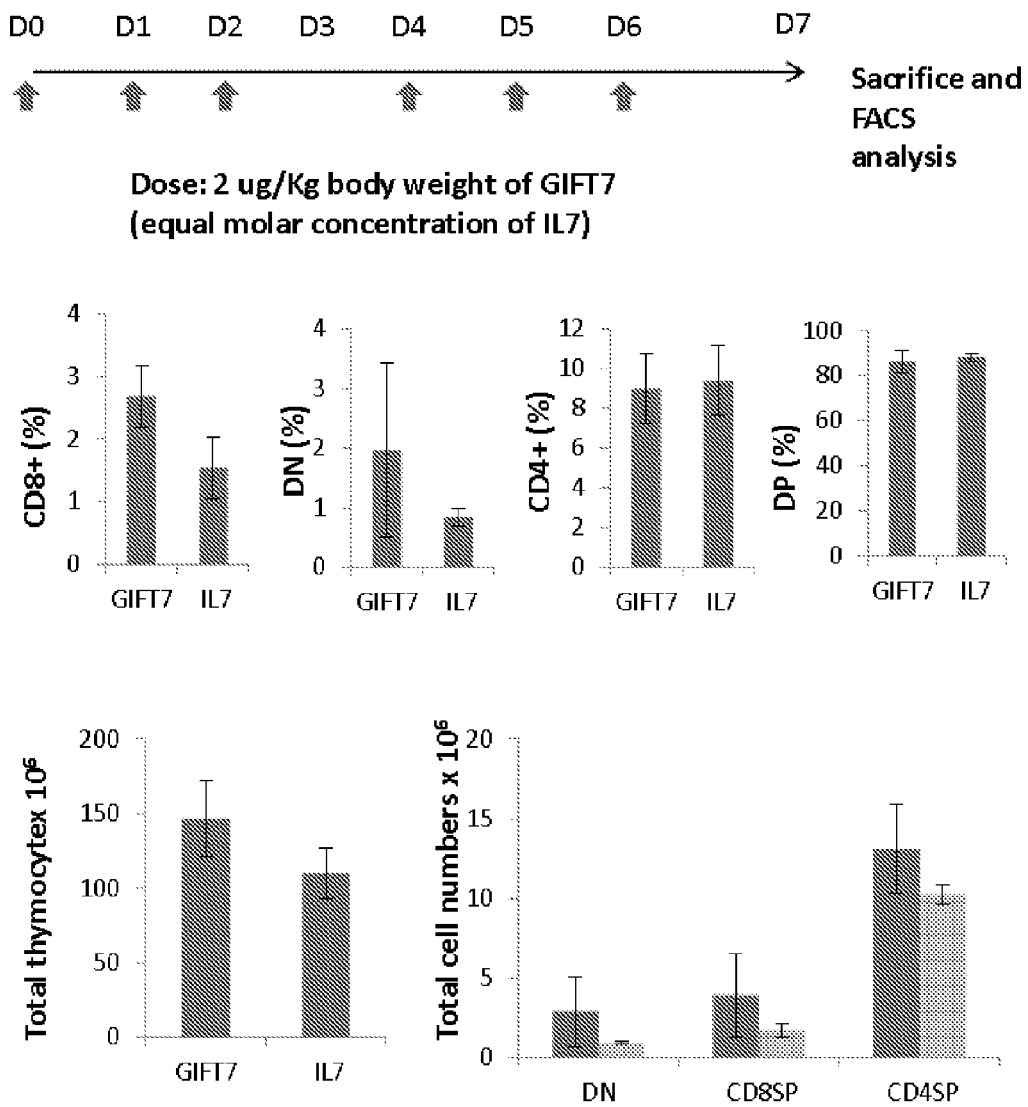
FIG. 4 shows the effect of GIFT7 on thymic output. (A,B) Thymoctes were treated with GIFT7 or cytokine control in vitro for 5 days. Ex vivo manipulated thymocytes were stained with the indicated antibodies and surface expression was analyzed by FCAS. (C) CFSE—labeled CD4/CD8 depeleted thymocytes were assessed by FCAS with co-staining of γδTCR after 5 days of in vitro GIFT7 treatment. (D) Whole thymic output of naïve mice administered with GIFT7 at the indicated doses was analyzed at day 7.
Figures 1, 5:
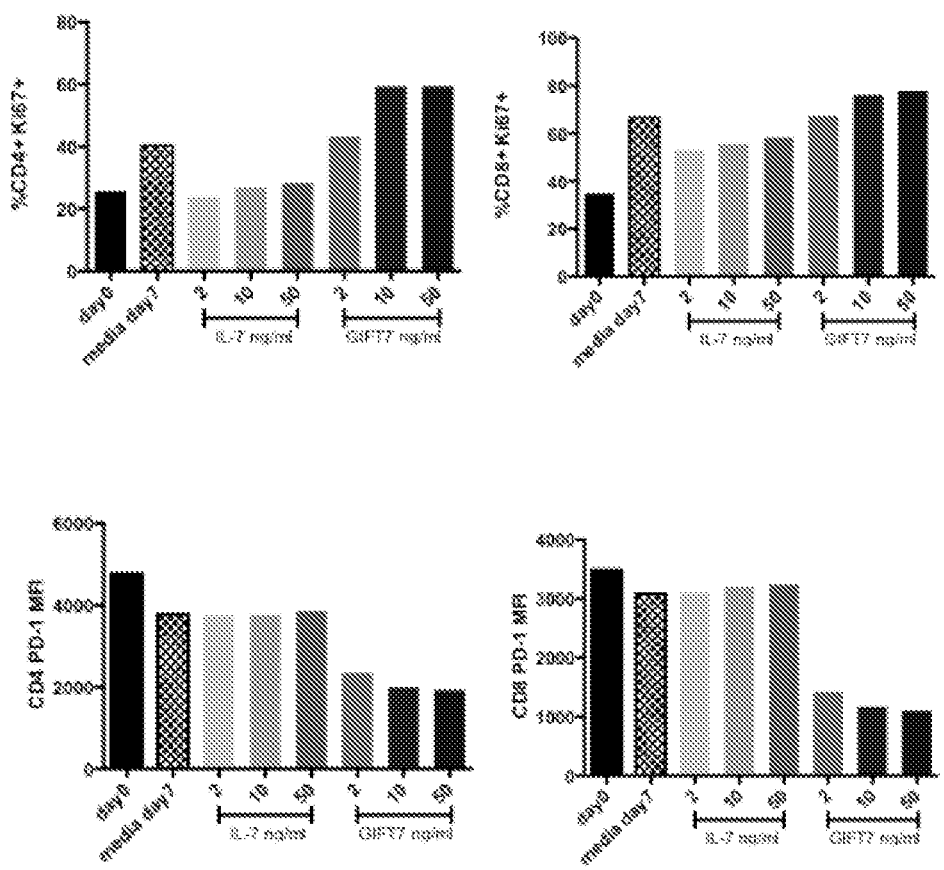
FIG. 5 shows the effect of GIFT7 on NHP and human PBMC. (A) PBMC was obtained from healthy primates and treated with GIFT7 after 48 hours of in vitro activation with conA. (B) PBMC was obtained from healthy volunteers and subsequently treated with GIFT7 after 48 hours of in vitro activation with CD3/CD28. Ki67 and PD1 expression was assessed by FACS.
Figures 2, 5:
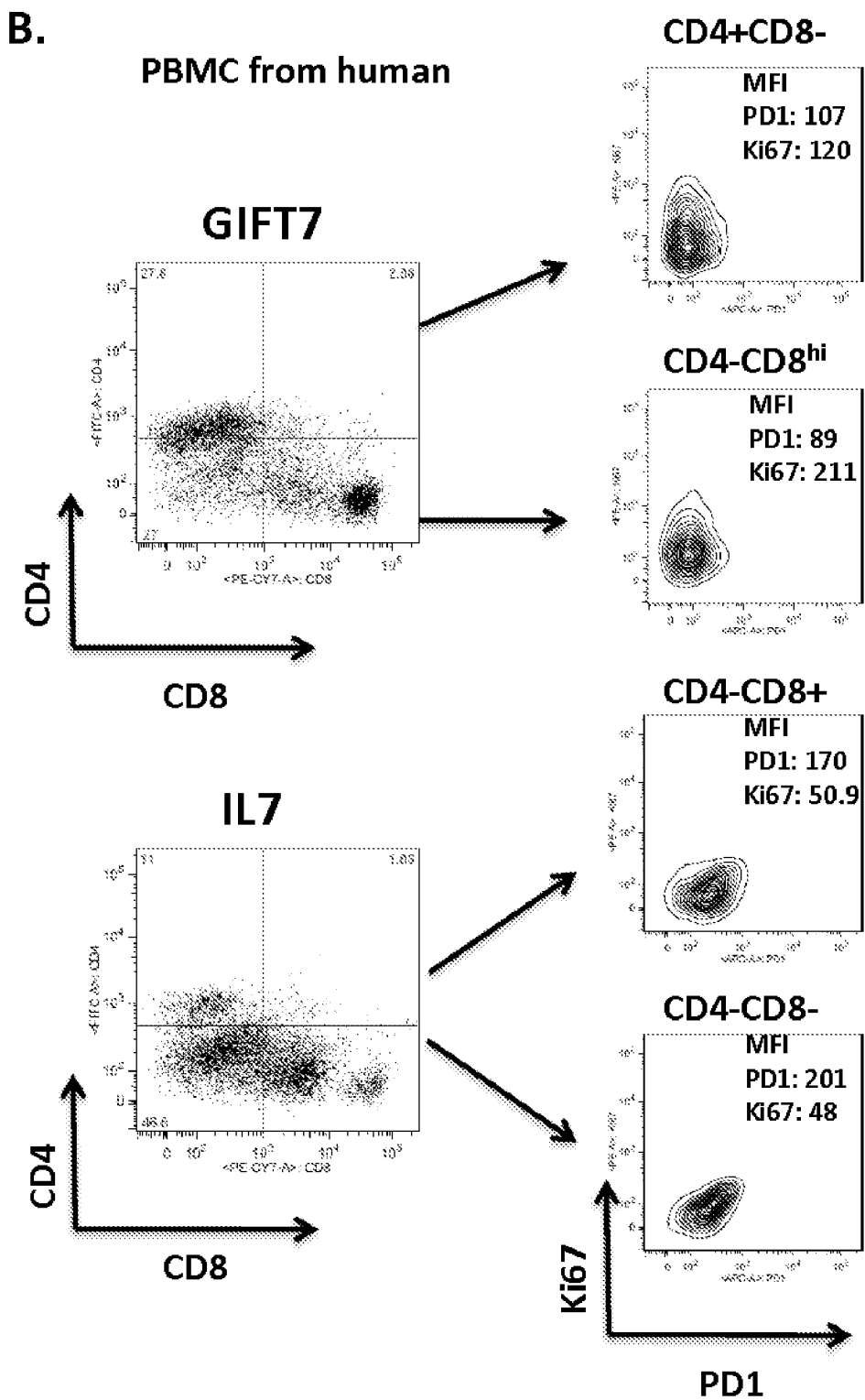

GIFT7 has novel pharmacological properties distinct from IL-7 alone. Specifically, (1) GIFT7 leads to a hyperagonistic response manifest by increase pSTAT5 in murine CD127⁺ lymphoid cells leading to a massive proliferative and pro-survival effect (FIG. 2); (2) The cell biological consequence on murine splenic T-cells is to selectively expand an antigen-experienced CD8⁺ subset with a Central Memory (CM) phenotype (FIG. 3A,B); (3) GIFT7 CD8 also demonstrate significant Th1-IFNγ-driven anti-tumor response in vitro and in vivo, and prolonged in vivo persistence following adoptive transfer in normal or tumor-bearing mice (FIG. 3C,D,E); (4) GIFT7 can expand CD4⁻CD8⁻CD44⁺CD25⁻ double negative 1 (DN1) T cell precursors in both αβ and γδ T cell lineage (FIG. 4A,B,C); The direct administration of GIFT7 protein to normal mice leads to the expansion of double negative (DN)

and CD8+ thymic subsets (FIG. 4D); and (5) the unique expansive effect of GIFT7 was also demonstrate on peripheral blood mononuclear cells (PBMC) derived from non-human primates (NHP) and human, in that GFIT7 stimulation of pre-activated PBMC typically leads to T cells proliferation without exhaustion ($Ki67^{hi}$ and $PD1^{low}$) compared to monomeric cytokine IL-7 (FIG. 5A, B).

Data collected on GIFT7 and GIFT7-CD8 suggests use in the treatment of human disorders where an enhanced of immune response is desirable, in particular chronic infectious ailments and cancer. Moreover, based on observations of GIFT7-mediated enhancement on thymic output (in particular in the DN1, γδ T cell precursor and SPCD8), GIFT7 or GIFT7-enhanced T cell precursors may be use of for the treatment of a non-exclusive listing of human immune deficient ailments such as congenital or HIV-mediated acquired immunodeficiency, after chemotherapy or after-hematopoietic stem cell transplant (HSCT) and for the ageing.

The present disclosure encompasses fusion proteins involving full-length pre-processed forms, as well as mature processed forms, fragments thereof and variants of each or both of the GM-CSF and IL-7 entities, including allelic as well as non-naturally occurring variants. In addition to naturally-occurring allelic variants of the GM-CSF and IL-7 entities that may exist in the population, the skilled artisan will further appreciate that changes (i.e. one or more deletions, additions and/or substitutions of one or more amino acid) can be introduced by mutation using classic or recombinant techniques to effect random or targeted mutagenesis. A suitable variant in use in the present disclosure typically has an amino acid sequence having a high degree of homology with the amino acid sequence of the corresponding native cytokine. In one embodiment, the amino acid sequence of the variant cytokine in use in the fusion protein of the disclosure is at least 70%, at least about 75%, at least about 80%, at least about 90%, typically at least about 95%, more typically at least about 97% and even more typically at least about 99% identical to the corresponding native sequence. In certain embodiments such native sequence is of human GM-CSF and/or human IL-7.

Percent identities between amino acid or nucleic acid sequences can be determined using standard methods known to those of skill in the art. For instance for determining the percentage of homology between two amino acid sequences, the sequences are aligned for optimal comparison purposes. The amino acid residues at corresponding amino acid positions are then compared. Gaps can be introduced in one or both amino acid sequence(s) for optimal alignment and non-homologous sequences can be disregarded for comparison purposes. When a position in the first sequence is occupied by the same amino acid residue as the corresponding position in the second sequence, then the sequences are identical at that position. The percent identity between the two sequences is a function of the number of identical positions shared by the sequences, taking into account the number of gaps which need to be introduced for optimal alignment and the length of each gap. The comparison of sequences and determination of percent identity and similarity between two sequences can be accomplished using a mathematical algorithm (e.g. Computational Molecular Biology, 1988, Ed Lesk A M, Oxford University Press, New York; Biocomputing: Informatics and Genome Projects, 1993, Ed Smith D. W., Academic Press, New York; Computer Analysis of Sequence Data, 1994, Eds Griffin A. M. and Griffin H. G., Human Press, New Jersey; Sequence Analysis Primer, 1991, Eds Griskov M. and Devereux J., Stockton Press, New York). Moreover, various computer programs are available to determine percentage identities between amino acid sequences and between nucleic acid sequences, such as GCG™ program (available from Genetics Computer Group, Madison, Wis.), DNAsis™ program (available from Hitachi Software, San Bruno, Calif.) or the MacVector™ program (available from the Eastman Kodak Company, New Haven, Conn.).

Suitable variants of GM-CSF and IL-7 entities for use in the present disclosure are biologically active and retain at least one of the activities described herein in connection with the corresponding polypeptide. Typically, the therapeutic effect (e.g. anti-tumor activity, by-pass of tumor-induced immune energy) is preserved, although a given function of the polypeptide(s) may be positively or negatively affected to some degree, e.g. with variants exhibiting reduced cytotoxicity or enhanced biological activity. Amino acids that are essential for a given function can be identified by methods known in the art, such as by site-directed mutagenesis. Amino acids that are critical for binding a partner/substrate (e.g. a receptor) can also be determined by structural analysis such as crystallization, nuclear magnetic resonance and/or photo-affinity labeling. The resulting variant can be tested for biological activity in assays such as those described above.

For example, in one class of functional variants, one or more amino acid residues are conservatively substituted. A "conservative amino acid substitution" is one in which the amino acid residue in the native polypeptide is replaced with an amino acid residue having a similar side chain. Families of amino acid residues having similar side chains have been defined in the art. Typically, substitutions are regarded as conservative when the replacement, one for another, is among the aliphatic amino acids Ala, Val, Leu, and Ile; the hydroxyl residues Ser and Thr; the acidic residues Asp and Glu; the amide residues Asn and Gln; the basic residues Lys and Arg; or the aromatic residues Phe and Tyr. Alternatively, in another embodiment, mutations can be introduced randomly along all or part of a cytokine coding sequence, such as by saturation mutagenesis, and the resultant mutant can be screened for its biological activity as described herein to identify mutants that retain at least therapeutic activity.

Although the GM-CSF and IL-7 entities can be directly fused in the fusion protein of the disclosure, it is however typical to use a linker peptide for joining GM-CSF and IL-7. The purpose of the linker is to allow the correct formation, folding and/or functioning of each of the GM-CSF and IL-7 entities. It should be sufficiently flexible and sufficiently long to achieve that purpose. Typically, the coding sequence of the linker may be chosen such that it encourages translational pausing and therefore independent folding of the GM-CSF and IL-7 entities. A person skilled in the art will be able to design suitable linkers in accordance with the disclosure. The present disclosure is, however, not limited by the form, size or number of linker sequences employed. Multiple copies of the linker sequence of choice may be inserted between GM-CSF and IL-7. The only requirement for the linker sequence is that it functionally does not adversely interfere with the folding and/or functioning of the individual entities of the fusion protein. For example, a suitable linker is 5 to 50 amino acid long and may comprise amino acids such as glycine, serine, threonine, asparagine, alanine and proline (see for example Wiederrecht et al., 1988, Cell 54, 841; Dekker et al., 1993, Nature 362, 852; Sturm et al., 1988, Genes and Dev. 2, 1582; Aumailly et al., 1990 FEBS Lett. 262, 82). Repeats comprising serine and glycine residues are typical in the context of the disclosure. Specific examples of suitable linkers consists of two or three or more (e.g. up to eight) copies of the sequence Gly-Gly-Gly-Gly-Ser (GGGGS). It will be evident that the disclosure is not limited to the use of these particular linkers.

The disclosure further includes fusion proteins which comprise, or alternatively consist essentially of, or alternatively consist of an amino acid sequence which is at least 70%, 75%, 80%, 90%, 95%, 97%, 99% homologous or even better 100% homologous (identical) to all or part of any of the amino acid sequences recited in SEQ ID NO: 1-2.

In the context of the present disclosure, a protein "consists of" an amino acid sequence when the protein does not contain any amino acids but the recited amino acid sequence. A protein "consists essentially of" an amino acid sequence when such an amino acid sequence is present together with only a few additional amino acid residues, typically from about 1 to about 50 or so additional residues. A protein "comprises" an amino acid sequence when the amino acid sequence is at least part of the final (i.e. mature) amino acid sequence of the protein. Such a protein can have a few up to several hundred additional amino acids residues. Such additional amino acid residues can be naturally associated with each or both entities contained in the fusion or heterologous amino acid/peptide sequences (heterologous with respect to the respective entities). Such additional amino acid residues may play a role in processing of the fusion protein from a precursor to a mature form, may facilitate protein trafficking, prolong or shorten protein half-life or facilitate manipulation of the fusion protein for assay or production, among other things. Typically, the fusion proteins of the disclosure comprise a signal peptide at the NH2-terminus in order to promote secretion in the host cell or organism. For example, the endogenous signal peptide (i.e. naturally present in the cytokine present at the NH2 terminus of said fusion) can be used or alternatively a suitable heterologous (with respect to the cytokine in question) signal peptide sequence can be added to the cytokine entity present at the NH2 terminus of the fusion or inserted in replacement of the endogenous one.

In the context of the disclosure, the fusion proteins of the disclosure can comprise cytokine entities of any origin, i.e. any human or animal source (including canine, avian, bovine, murine, ovine, feline, porcine, etc). Although "chimeric" fusion proteins are also encompassed by the disclosure (e.g. one cytokine entity of human origin and the other of an animal source), it is typical that each entity be of the same origin (e.g. both from humans).

The fusion proteins of the present disclosure can be produced by standard techniques. Polypeptide and DNA sequences for each of the cytokines involved in the fusion protein of the present disclosure are published in the art, as are methods for obtaining expression thereof through recombinant or chemical synthetic techniques. In another embodiment, a fusion-encoding DNA sequence can be synthesized by conventional techniques including automated DNA synthesizers. Then, the DNA sequence encoding the fusion protein may be constructed in a vector and operably linked to a regulatory region capable of controlling expression of the fusion protein in a host cell or organism. Techniques for cloning DNA sequences for instance in viral vectors or plasmids are known to those of skill in the art (Sambrook et al, 2001, "Molecular Cloning. A Laboratory Manual", Laboratory Press, Cold Spring Harbor N.Y.). The fusion protein of the disclosure can be purified from cells that have been transformed to express it.

The present disclosure also provides a nucleic acid molecule encoding the fusion protein of the disclosure. Within the context of the present disclosure, the term "nucleic acid" and "polynucleotide" are used interchangeably and define a polymer of nucleotides of any length, either deoxyribonucleotide (DNA) molecules (e.g., cDNA or genomic DNA) and ribonucleotide (RNA) molecules (e.g., mRNA) and analogs of the DNA or RNA generated using nucleotide analogs (see U.S. Pat. No. 5,525,711 and U.S. Pat. No. 4,711,955 as examples of nucleotide analogs). If present, modifications to the nucleotide structure may be imparted before or after assembly of the polymer. The sequence of nucleotides may also be interrupted by non-nucleotide elements. The nucleic acid molecule may be further modified after polymerization, such as by conjugation with a labeling component. The nucleic acid, especially DNA, can be double-stranded or single-stranded, but typically is double-stranded DNA. Single-stranded nucleic acids can be the coding strand (sense strand) or the non-coding strand (anti-sense strand).

The nucleic acid molecules of the disclosure include, but are not limited to, the sequence encoding the fusion protein alone, but may comprise additional non-coding sequences, for example introns and non-coding 5' and 3' sequences that play a role in transcription, mRNA processing (including splicing and polyadenylation signals), ribosome binding and mRNA stability. For example, the nucleic acid molecule of the disclosure can contain less than about 5 kb, 4 kb, 3 kb, 2 kb, 1 kb, 0.5 kb or 0.1 kb of nucleotide sequences which naturally flank (i.e. sequences located at the 5' and 3' ends) or are present within the genomic DNA encoding GM-CSF and IL-7 entities.

According to a typical embodiment, the present disclosure provides nucleic acid molecules which comprise, or alternatively consist essentially of, or alternatively consist of a nucleotide sequence encoding all or part of an amino acid sequence encoding a fusion protein which is at least about 70%, at least about 75%, at least about 80%, at least about 90%, at least about 95%, typically at least about 97%, more typically at least about 99% homologous or even more typically 100% homologous to any of the amino acid sequences shown in SEQ ID NO: 1-2.

In another embodiment, a nucleic acid molecule of the disclosure comprises a nucleic acid molecule which is a complement of all or part of a nucleotide sequence encoding the fusion protein shown in any of SEQ ID NO: 1-2. A nucleic acid molecule which is complementary to the nucleotide sequence of the present disclosure is one which is sufficiently complementary such that it can hybridize to the fusion-encoding nucleotide sequence under stringent conditions, thereby forming a stable duplex. Such stringent conditions are known to those skilled in the art. A typical, non-limiting example of stringent hybridization conditions are hybridization in 6 times sodium chloride/sodium citrate (SSC) at about 45 C, followed by one or more washes in 0.2 times SSC, 0.1% SDS at 50-65 C. In one embodiment, the disclosure pertains to antisense nucleic acid to the nucleic acid molecules of the disclosure. The antisense nucleic acid can be complementary to an entire coding strand, or to only a portion thereof.

In still another embodiment, the disclosure encompasses variants of the above-described nucleic acid molecules of the disclosure e.g., that encode variants of the fusion proteins that are described above. The variation(s) encompassed by the present disclosure can be created by introducing one or more nucleotide substitutions, additions and/or deletions into the nucleotide sequence by standard techniques, such as site-directed mutagenesis and PCR-mediated mutagenesis. Following mutagenesis, the variant nucleic acid molecule can be expressed recombinantly as described herein and the activity of the resulting protein can be determined using, for example, assays described herein. Alternatively, the nucleic acid molecule of the disclosure can be altered to provide preferential codon usage for a specific host cell (for example *E. coli*; Wada et al., 1992, Nucleic Acids Res. 20, 2111-2118). The disclosure further encompasses nucleic acid molecules that differ due to the degeneracy of the genetic code and thus encode for example the same fusion protein as any of those shown in SEQ ID NO: 1-2.

Another embodiment of the disclosure pertains to fragments of the nucleic acid molecule of the disclosure, e.g. restriction endonuclease and PCR-generated fragments. Such fragments can be used as probes, primers or fragments encoding an immunogenic portion of the fusion protein.

The nucleic acid molecules of the present disclosure can be generated using the sequence information provided herein. The nucleic acid encoding each of the GM-CSF and IL-7 entities can be cloned or amplified using cDNA or, alternatively, genomic DNA, as a template and appropriate probes or oligonucleotide primers according to standard molecular biology techniques (e.g., as described in Sambrook, et al. "Molecular Cloning: A Laboratory Manual", Cold Spring Harbor Laboratory Press, Cold Spring Harbor, N.Y., 2001) or standard PCR amplification techniques based on sequence data accessible in the art (such as those provided above in connection with the fusion proteins of the disclosure or those provided in the Examples part). Fusing of the GM-CSF sequence to the IL-7 sequence may be accomplished as described in the Experimental below or by conventional techniques. For example, the GM-CSF and IL-7 encoding sequences can be ligated together in-frame either directly or through a sequence encoding a peptide linker. The GM-CSF-encoding sequence can also be inserted directly into a vector which contains the IL-7-encoding sequence, or vice versa. Alternatively, PCR amplification of the GM-CSF and IL-7-encoding sequences can be carried out using primers which give rise to complementary overhangs which can subsequently be annealed and re-amplified to generate a fusion gene sequence.

GIFT7 Overcomes T Cell Exhaustion Leading to the Expansion of Peripheral T Cell in a PD1$^{low}$ State T-cell based immunotherapy represents a promising strategy for chronic viral infections or malignancies. However, its efficacy depends on the infused T cell fitness in vivo. Indeed, T cell exhaustion via the upregulation of PD-1 reflects the maladaptive immune response as a cause of effector cell failure. To address this issue, data herein indicates that GIFT7 leads to a hyperagonistic response manifest by increased pSTAT5 and proliferation in CD3$^+$/CD127$^+$ cells. GIFT7 also selectively expand a CD8$^+$ subset from pre-activated T cells with a Central Memory phenotype defined as CD8$^+$CD44$^+$ CD62L$^+$CCR7$^+$KLRG$^-$CD27$^+$PD-1$^-$, hereafter $T_{GIFT7}$. Adoptive transfer of OT1-derived CD8 $T_{GIFT7}$ into OVA-EG7-bearing mice leads to a significant anti-tumor effect. Furthermore, $T_{GIFT7}$ persist long-term whilst IL2-activated CD8 T-cells are undetected. The unique expansive effect of the human ortholog of GIFT7 on peripheral blood mononuclear cells (PBMC) derived from non-human primates (NHP) and humans, in that GIFT7 stimulation of pre-activated PBMC leads to T cell prolifetaion without exhaustion (KI67$^{hi}$ and PD-1$^{low}$) in CD4$^+$, CD8$^+$, and CD4$^-$ CD8$^-$ compartments. This observation supports the use of GIFT7 primed T cells for chronic viral infections or malignancies where an inadequate T cell response is a common feature.

GIFT7 Reverses Age-Related Thymic Atrophy by Expanding CD44$^{int}$ Double-Negative Resident Thymic Progenitors Via IL7Rα/γ$_c$ Hypersignalling Immune insufficiency secondary to ageing predisposes the host to detrimental infections.

Immune senescence manifested by thymic involution correlates to the progressive decline in T cell receptor (TCR) repertoire and numerous defects in cellular immunity with severe clinical complications such as chronic inflammation, autoimmune diseases, and low vaccination efficacy. Normal thymopoiesis arises from marrow-derived CD4$^-$CD8$^-$ double-negative T cell progenitors (DN). Thereafter, DN develop into mature single-positive (SP) CD4 or CD8 T cells after expressing both CD4 and CD8 (double-positive-DP) transiently, leading to de novo T cell production. Age-related progressive decline in thymic activity starts as early as the first year of postnatal life and is due to a combination of reduced thymic stroma and intrathymic proliferation of lymphoid precursors.

Interleukin-7 (IL-7) plays a role in T cell development and homeostasis by signalling through its cognate receptor complex IL7Rα/γ$_c$. The correlation between age-related hypotonic thymic activity and IL7 availability in the stromal niche is not clearly defined. IL7 is detectable in aged thymus. The use of exogenous IL7 for therapeutic lymphogenesis has been attempted. However, peripheral T cell compartmentalization—preferential expansion of naïve and central memory CD4$^+$ T cell—is a much more pronounced effect secondary to exogenous IL7 administration; thymic function remains largely unaltered. See Chu et al., Blood, 2004, 104(4):1110-1119. The intrathymic implantation of genetically engineered IL7-producing stromal cells show no benefits in overcoming age-associated atrophy and the maintenance of peripheral T cell pool despite a transient increase in intrathymic proliferation. See Phillips et al., J Immunol, 2004, 173(8):4867-4874.

Part of the reason for its modest therapeutic effect is believed to be related to the homeostatic nature of IL7/IL7Rα interaction. The expression of IL7Rα is tightly regulated: it is upregulated on hematolymphoid cells destined to persist; it is downregulated on quiescent or exhausted cells, and it is internalized upon ligand binding. Thus, the in vivo use of IL7 for regenerative immunotherapy is limited by the requirement to achieve supraphysiological concentration in order to overcome immune checkpoints to its activating effects.

Studies herein indicate that engineered fusion GIFT7 delivers hyperagonistic signalling to IL7Rα/γ$_c$, hyperphosphorylating signal transducer and activator of transcription (STAT) 5. The biological consequence of STAT5 hyperactivation is the induction of SPCD8 and CD44$^+$CD25$^-$DN1 expansion in thymocyte culture. Systemic administration of GIFT7 in young immune competent mice leads to an immediate increase in the number of DN1, which subsequently progress to an increase in the total number of thymocytes and DP. GIFT7-mediated hypertrophic effect is significantly more pronounced in aged thymi; it precipitates the expansion of a subset of early thymic precursors CD44int DN1, which is capable of participating in normal T cell development, leading to a significant enhancement of thymic cellularity, cortical hyperplasia, and peripheral viral-specific CD8$^+$ response. Overall, by using GIFT7-derived hypersignalling to IL7Rα/γ$_c$ under conditions of age-associated thymic insufficiency, the properties of a unique population of resident thymic precursors capable of repopulating T lineage cells are exploited.

Sustained postnatal T cell development depends on the continuous supply of bone marrow derived hematopoietic stem cells as resident thymocytes are deemed to possess limited self-renewing capacity. This is evident in that mature T cells are rapidly replaced by BM sources after transient detection of thymic output in the periphery after thymic transplants. However, this theory has been questioned recently. Allman et al shows that early thymic progenitors (ETPs) and BM common lymphoid progenitors (CLPs) are phenotypically diverse—postulating that thymic T lineage precursors represent a different route than BM CLPs. See Allman et al., Nat Immunol, 2003, 4(2):168-174. Matins et al describes thymic-autonomous T cell development with normal intrathymic differentiation and TCR diversification in the events of defective receptor tyrosine kinase Kit and $\gamma_c$ signalling localized at the BM compartment. See Martins et al., entitled "Thymus-autonomous T cell development in the absence of progenitor import." J Exp Med. 2012. By eliminating BM-derived competition for thymic survival niche, resident thymocytes exhibit full self-renewing capacities. Peaudecerf et al describes a population of thymic precursors with the capacity to persist in the complete absence of functional bone marrow supply and defined them phenotypically as $CD3^-CD4^-CD8^-CD44^+CD25^{low}IL-7R^{low}$ TN1-TN2 cells. See Peaudecerf et al., entitled "Thymocytes may persist and differentiate without any input from bone marrow progenitors." J Exp Med. 2012. Interestingly, both studies point to the importance of bone marrow-specific IL7-IL7R$\alpha$/$\gamma_c$ axis disruption in restoring intrathymic self-renewal when contrasting their current findings to the long-standing dogma of marrow-dependent thymopoiesis. Thus, the continuous replacement of thymic progenitors by the bone marrow represents the competition for survival signals (i.e. IL7) in the thymic niche instead of an intrinsic hierarchy of differentiation potential between bone marrow derived and resident thymic T-lineage precursors.

Figure 10A:
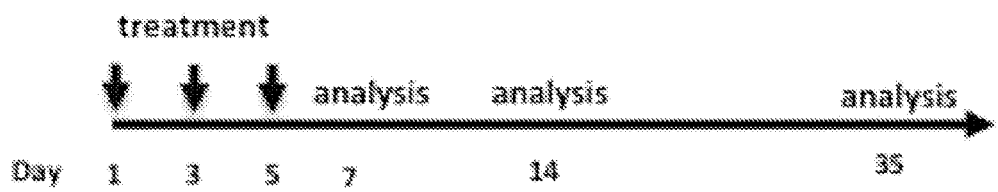
FIGS. 10A-D show data indicating GIFT7 leads to transient thymic hyperplasia in young mice (A) 2-month-old C57Bl/6 were injected with three doses of GIFT7 or IL7 i.v. (5 ug/Kg) at 1-day interval. Thymi collected on day 7, 14, or 35 were analyzed for total and subset cellularity. (B) Total thymic cellularity in GIFT7 or IL7-treated groups at each time point. Results represent the mean cell number+/−SD (n=3-5); *P<0.05 (C, D) Dissociated thymi were analyzed for CD3-5, CD4, CD8, CD25, and CD44 expression. Dot plots from one representative animal indicate the frequency of each thymic subset on day 7 in (C) and day 14 in (D). The histograms represent the number of cells associated with each phenotype. Data represent mean+/−SD (n=5)*p<0.05.
Figure 10C:
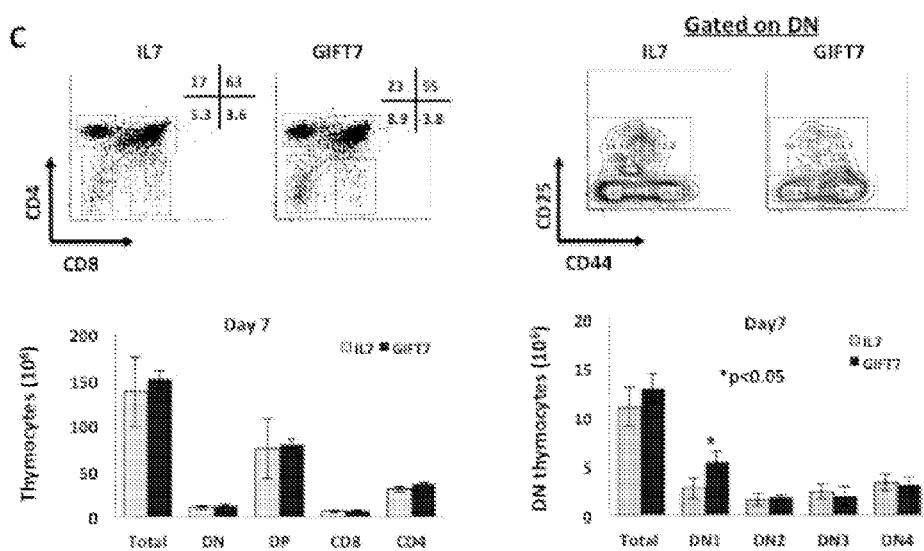
Figure 10D:
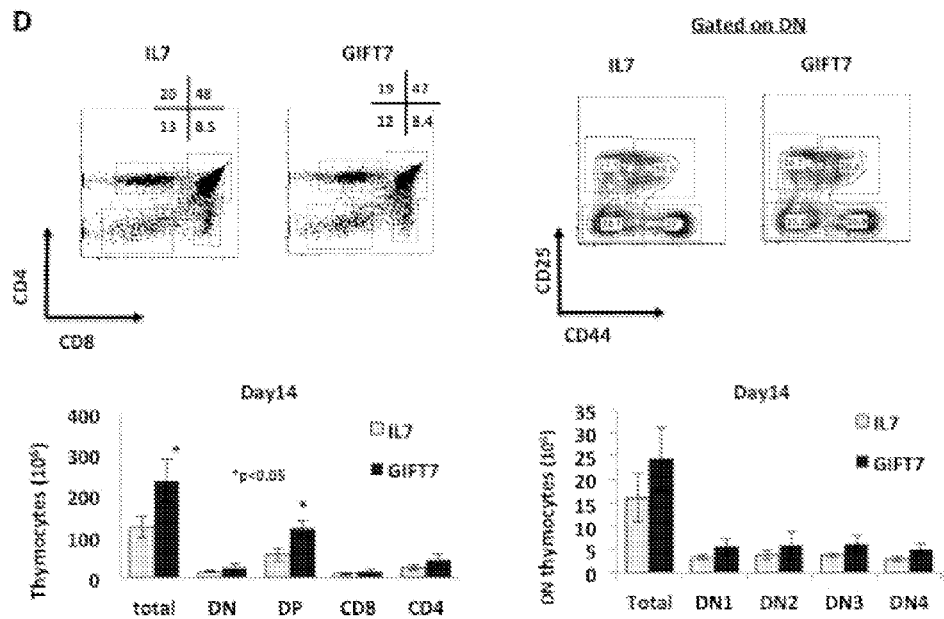
Figure 11A:
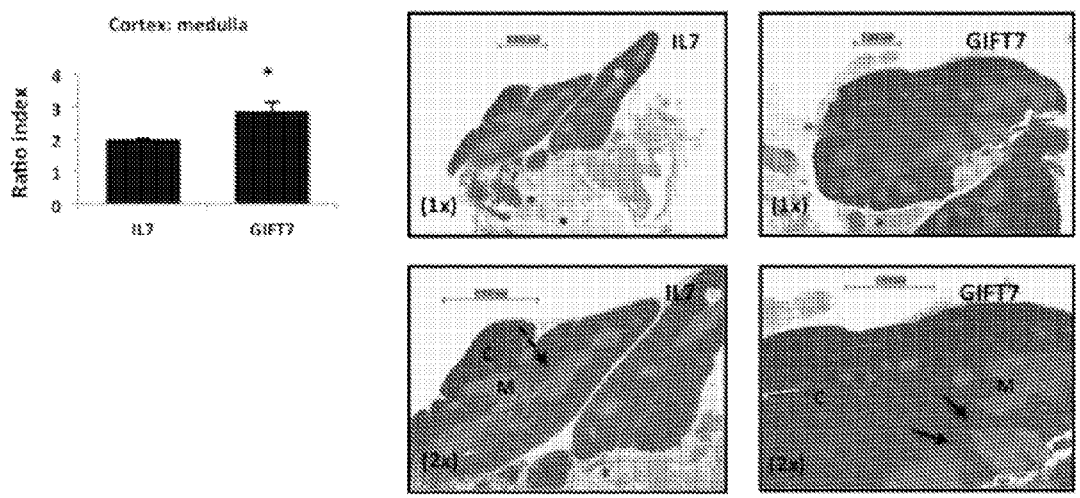
FIGS. 11A-C show data indicates that GIFT7 corrects age-related thymic atrophy (A) Hematoxylin- and eosin-stained paraffin sections of thymus from one representative GIFT7- or IL7-treated aged mice. Higher magnification show cortical hyperplasia infiltrating the lining of cortical medullary junction (solid arrow) compared to the smooth lining in IL7-treated group (interrupted arrow). Asterisk, adipose tissue deposit; C, cortex; M, medulla. The histogram indicates the ratio of cortical/medullary thickness. Data represent the mean value+/−SD (n=6); *p<0.05 (B) Increase in the number of total, DN, DP, SPCD4, and SPCD8 thymocytes of the GIFT7-treated aged mice. Thymi were dissociated and analyzed by flow cytometry. Histogram represent mean number of cells+/−SD (n=6). (C) GIFT7 administration leads to increased thymic output. mRNA expression of single-joint (sj) TREC to TCRα ratio of splenocytes from aged mice were measured by RT-PCR. Histogram represents fold difference of the relative mRNA expression (2-ΔCT of sjTREC to TCRα) from each treated mice normalized to the mean relative mRNA expression from the untreated group. RT-PCR was performed in triplicates.
Figure 11B:
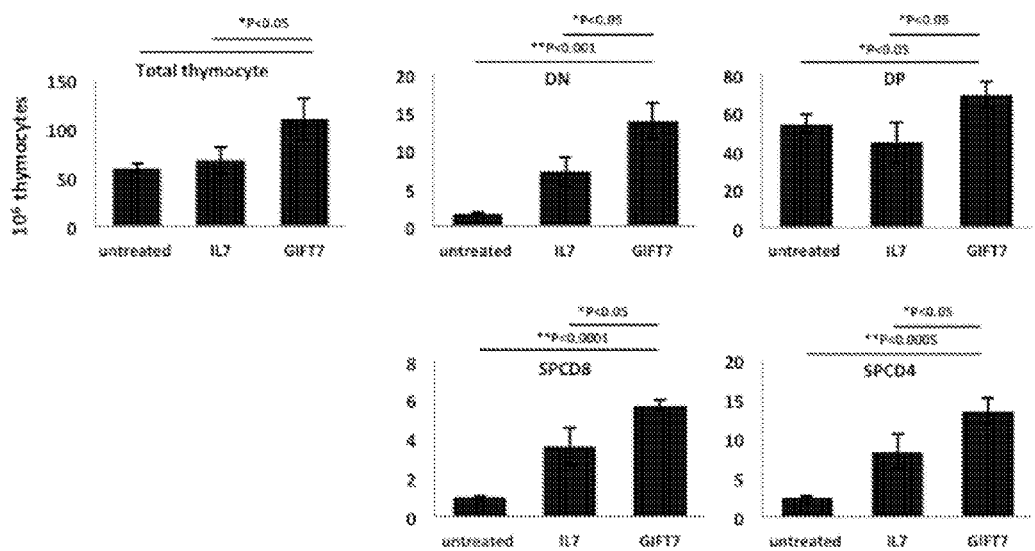
Figure 11C:
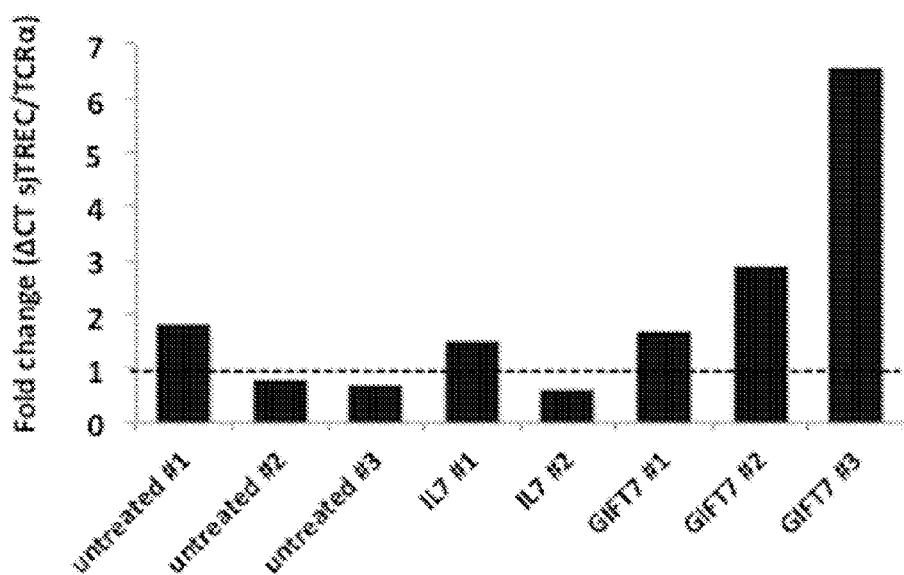
Figure 12B:
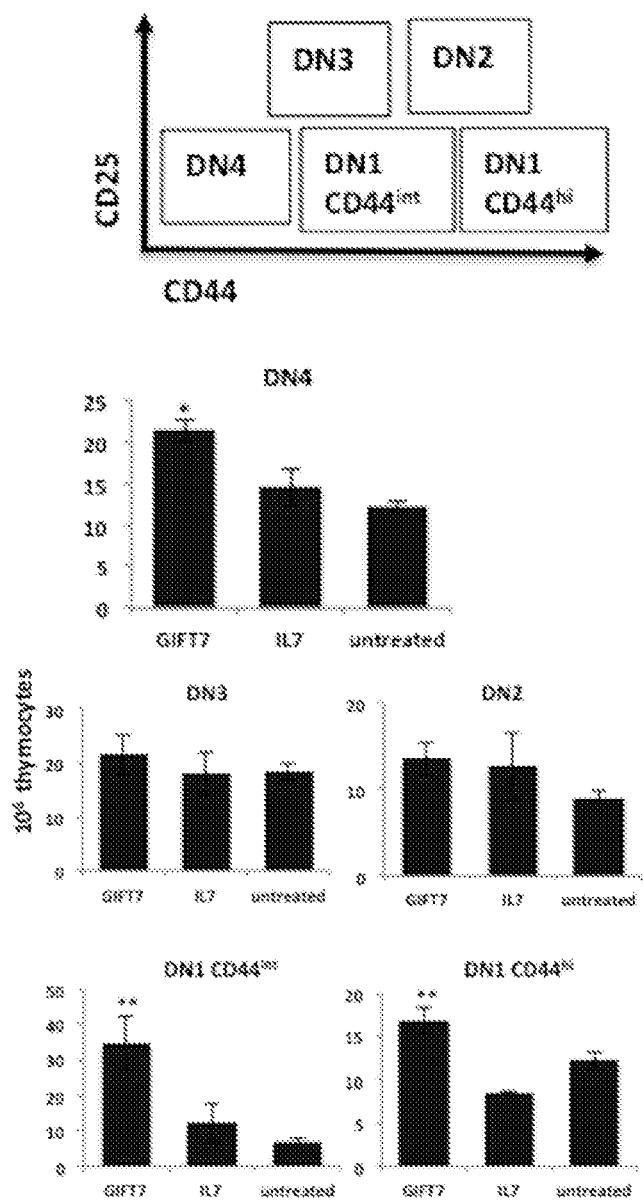
Figure 12C:
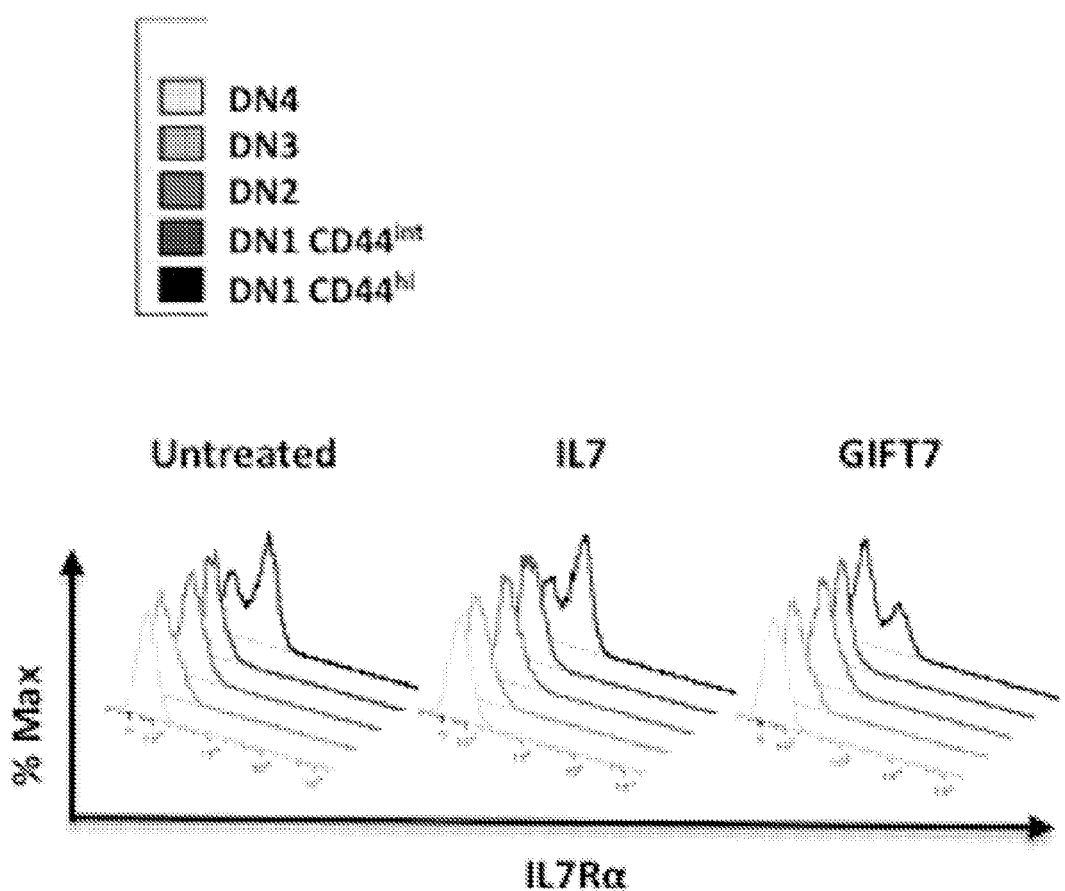
Figure 13A:
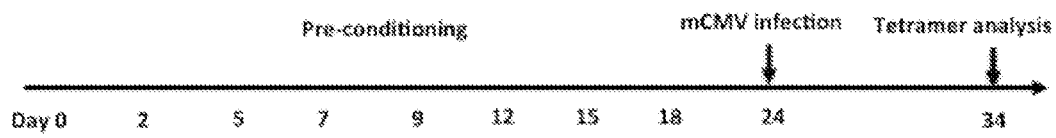
FIGS. 13A-D show data indicating GIFT7 treatment enhances anti-CMV CD8 response in aged mice (A) Schematic representation indicates 7 i.p. injections of GIFT7 or cytokine controls at 5 ug/kg (arrowhead) in aged mice. 2.5× 10⁴ PFU of MCMV were injected 6 days after the treatment. Spleens were analyzed for total or viral-specific cellularity 10 days post-infection. (B) Representative flow dot plots show the CMV-specific CTL response in young or aged mice treated with different treatment. Numbers indicate the percentage of CMV+ CTL. (C) Histogram represents the mean percentage or (D) number of cells in each group+/−SD (n=4).
Figure 13B:
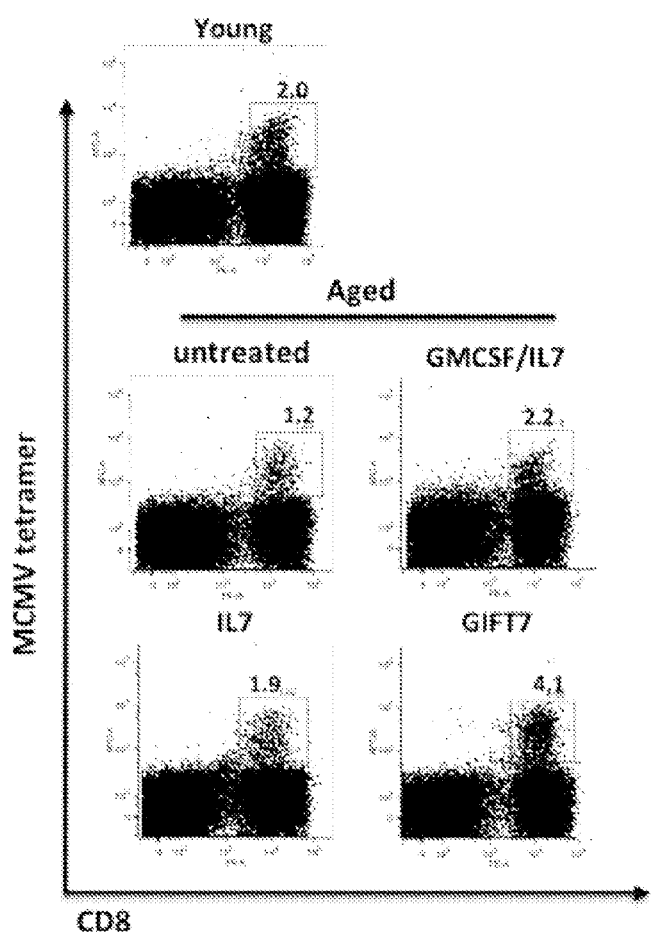
Figure 13C:
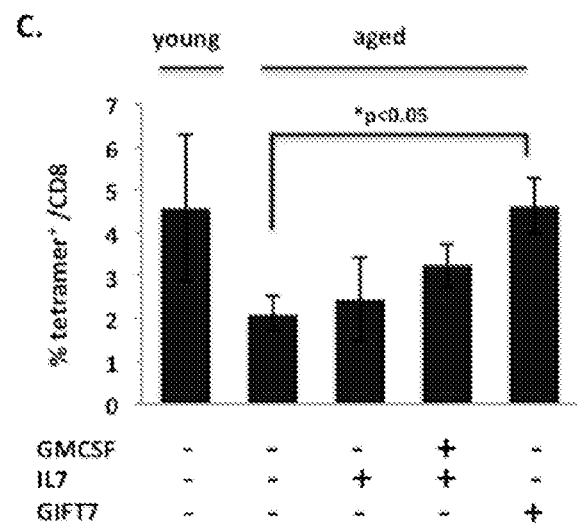
Figure 13D:
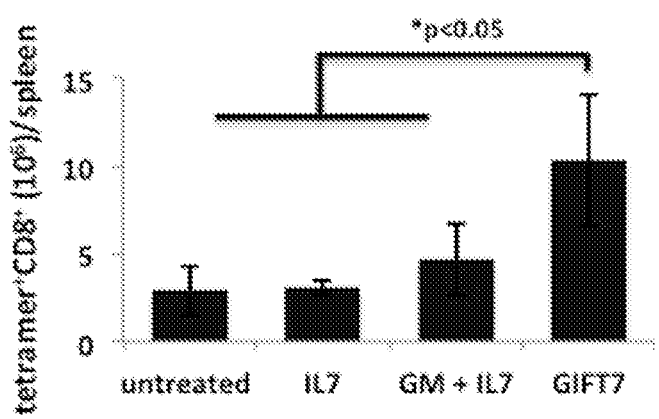

Studies herein demonstrate that other than eliminating IL7-responsiveness in the bone marrow, providing an exogenous suprapysiological level of IL7 signalling (i.e. GIFT7) also reveals the autonomy of thymic T cell development under both immune replete and insufficient states. Systemic administration of GIFT7 drives DN1 expansion (FIG. 10C), which subsequently leads to an increase in total number of thymocytes as well as DP in two weeks (FIG. 10D). This implicates that the immediate effect of hypertonic IL7 signalling on thymic composition is the preferential expansion of early T cell precursors destined to persist and differentiate along the fate of T lymphopoiesis. This is not achievable via physiological signalling of IL7R$\alpha$/$\gamma_c$ as previous studies have demonstrated the limited impact of IL7 supplementation on thymic ratio under immune competent conditions. See Chu et al., Blood, 2004, 104(4):1110-1119 and Phillips et al., J Immunol, 2004, 173(8):4867-4874. The ontogeny of resident thymic precursors was further investigated by superimposing suprapysiological signalling of IL7 on age-related thymic insufficiency. The reduction of survival niche in the thymus responded to GIFT7 in a dramatic fashion: hypertrophy of cortical tissue (FIG. 11A), disruption of cortical-medullary junction (FIG. 11A), and a 4-fold increase in the specific subset of $CD44^{int}$ DN1 (FIG. 12B). The increase in the RNA level of sjTREC per splenic TCR$\alpha^+$ T cells suggests that GIFT7-regenerated $CD44^{int}$ DN1 undergoes normal T cell development (i.e. a rearrangement) thus contributing to peripheral T lymphoid compartmentalization (FIG. 11C). This is especially significant in light of the diminishment of repertoire diversity as a cause of weakened host defense during ageing. Indeed, the repopulation of resident thymic precursors via GIFT7 leads to enhanced CTL response against MCMV, presumably by expanding TCR diversity at the periphery, rendering mature lymphocytes more readily available in responding to newly-encountered antigens (FIG. 13D). In vivo data indicates that $CD44^{int}$ DN1 subset is most responsive to GIFT7-mediated IL7R$\alpha$/$\gamma_c$ hypersignalling, and its expansion in frequency and absolute numbers restores thymopoiesis and reverses aged-related atrophy. However, $CD44^{int}$ DN1 express lower levels of IL7R$\alpha$ compared to the CD44hi subset (FIG. 12C). This seemingly paradoxical finding can be explained by the unique binding of fusokines to its heterodimeric receptors. GIFT fusion induces receptor clustering and trans-activates both the $\alpha$ and $\gamma_c$ chains of the heterodimeric receptor complex, which enables signaling activation even on cells with low level of receptor expression.

There is considerable heterogeneity and discrepancy of the ontogeny of intrathymic T cell progenitors. Here, the existence of a subset of resident thymocytes capable of T cell neogenesis is proposed, and its expansion and repopulation in aged thymi is triggered by pharmacologic IL7R$\alpha$/$\gamma_c$ hypersignalling. Their phenotype ($CD4-CD8-CD44^{int}CD25-IL7R\alpha^{low}$) resembles the TN1-TN2 cells capable of marrow-independent thymic renewal described by Peaudecerf et al. Keratinocyte growth factor (KGF), growth hormone or ghrelin reorganize thymic architecture by acting on thymic epithelial cells (TECs) with only modest effect on lymphoid progenitors. $\Gamma c$ cytokine replacement therapy seems to have more impact on peripheral T cell pool than de novo T cell production. Here, a novel thymic trophic approach is described by providing direct mitogenic signals to T cell precursors via IL7R$\alpha$/$\gamma_c$ axis. Based on our phosphorylation STATS data, it is proposed that GIFT7 enables a hypertonic, suprapysiological IL7R$\alpha$/$\gamma_c$ dependent signaling even on IL7R$\alpha^{low}$ cells. Hence, the use of GIFT7 or GIFT7-enhanced T cell precursors for the treatment of a non-exclusive listing of human thymic hypoimmune ailments with unmet clinical needs such as congenital or HIV-mediated acquired immunodeficiency, post-ablative cytotoxic chemotherapy and ageing.

Pharmaceutical Compositions

As used herein the language "pharmaceutically acceptable excipient" is intended to include any and all carriers, solvents, diluents, excipients, adjuvants, dispersion media, coatings, antibacterial and antifungal agents, and absorption delaying agents, and the like, compatible with pharmaceutical administration.

Suitably, the pharmaceutical composition of the disclosure comprises a carrier and/or diluent appropriate for its delivering by injection to a human or animal organism. Such carrier and/or diluent is non-toxic at the dosage and concentration employed. It is selected from those usually employed to formulate compositions for parental administration in either unit dosage or multi-dose form or for direct infusion by continuous or periodic infusion. It is typically isotonic, hypotonic or weakly hypertonic and has a relatively low ionic strength, such as provided by sugars, polyalcohols and isotonic saline solutions. Representative examples include sterile water, physiological saline (e.g. sodium chloride), bacteriostatic water, Ringer's solution, glucose or saccharose solutions, Hank's solution, and other aqueous physiologically balanced salt solutions (see for example the most current edition of Remington: The Science and Practice of Pharmacy, A. Gennaro, Lippincott, Williams & Wilkins). The pH of the composition of the disclosure is suitably adjusted and buffered in order to be appropriate for use in humans or animals, typically at a physiological or slightly basic pH (between about pH 8 to about pH 9, with a special preference for pH 8.5). Suitable buffers include phosphate buffer (e.g. PBS), bicarbonate buffer and/or Tris buffer. A typical composition is formulated in 1M saccharose, 150 mM NaCl, 1 mM MgCl2, 54 mg/l Tween 80, 10 mM Tris pH 8.5. Another typical composition is formulated in 10 mg/ml mannitol, 1 mg/ml HSA, 20 mM Tris, pH 7.2, and 150 mM NaCl.

The composition of the disclosure can be in various forms, e.g. in solid (e.g. powder, lyophilized form), or liquid (e.g. aqueous). In the case of solid compositions, the typical methods of preparation are vacuum drying and freeze-drying which yields a powder of the active agent plus any additional desired ingredient from a previously sterile-filtered solution thereof. Such solutions can, if desired, be stored in a sterile ampoule ready for reconstitution by the addition of sterile water for ready injection.

Nebulized or aerosolized formulations also form part of this disclosure. Methods of intranasal administration are well known in the art, including the administration of a droplet, spray, or dry powdered form of the composition into the nasopharynx of the individual to be treated from a pressured container or dispenser which contains a suitable propellant, e.g., a gas such as carbon dioxide, or a nebulizer (see for example WO 95/11664). Enteric formulations such as gastroresistant capsules and granules for oral administration, suppositories for rectal or vaginal administration also form part of this disclosure. For non-parental administration, the compositions can also include absorption enhancers which increase the pore size of the mucosal membrane. Such absorption enhancers include sodium deoxycholate, sodium glycocholate, dimethyl-beta-cyclodextrin, lauroyl-1-lysophosphatidylcholine and other substances having structural similarities to the phospholipid domains of the mucosal membrane.

The composition can also contain other pharmaceutically acceptable excipients for providing desirable pharmaceutical or pharmacodynamic properties, including for example modifying or maintaining the pH, osmolarity, viscosity, clarity, color, sterility, stability, rate of dissolution of the formulation, modifying or maintaining release or absorption into an the human or animal organism. For example, polymers such as polyethylene glycol may be used to obtain desirable properties of solubility, stability, half-life and other pharmaceutically advantageous properties (Davis et al., 1978, Enzyme Eng. 4, 169-173; Burnham et al., 1994, Am. J. Hosp. Pharm. 51, 210-218). Representative examples of stabilizing components include polysorbate 80, L-arginine, polyvinylpyrrolidone, trehalose, and combinations thereof. Other stabilizing components especially suitable in plasmid-based compositions include hyaluronidase (which is thought to destabilize the extra cellular matrix of the host cells as described in WO 98/53853), chloroquine, protic compounds such as propylene glycol, polyethylene glycol, glycerol, ethanol, 1-methyl L-2-pyrrolidone or derivatives thereof, aprotic compounds such as dimethylsulfoxide (DMSO), diethylsulfoxide, di-n-propylsulfoxide, dimethylsulfone, sulfolane, dimethyl-formamide, dimethylacetamide, tetramethylurea, acetonitrile (see EP 890 362), nuclease inhibitors such as actin G (WO 99/56784) and cationic salts such as magnesium ($Mg^2$) (EP 998 945) and lithium ($Li^+$) (WO 01/47563) and any of their derivatives. The amount of cationic salt in the composition of the disclosure typically ranges from about 0.1 mM to about 100 mM, and still more typically from about 0.1 mM to about 10 mM. Viscosity enhancing agents include sodium carboxymethylcellulose, sorbitol, and dextran. The composition can also contain substances known in the art to promote penetration or transport across the blood barrier or membrane of a particular organ (e.g. antibody to transferrin receptor; Friden et al., 1993, Science 259, 373-377). A gel complex of poly-lysine and lactose (Midoux et al., 1993, Nucleic Acid Res. 21, 871-878) or poloxamer 407 (Pastore, 1994, Circulation 90, 1-517) can be used to facilitate administration in arterial cells.

The composition of the disclosure may also comprise one or more adjuvant(s) suitable for systemic or mucosal application in humans. Representative examples of useful adjuvants include without limitation alum, mineral oil emulsion such as Freunds complete and incomplete, lipopolysaccharide or a derivative thereof (Ribi et al., 1986, Immunology and Immunopharmacology of Bacterial Endotoxins, Plenum Publ. Corp., NY, p407-419), saponins such as QS21 (Sumino et al., 1998, J. Virol. 72, 4931-4939; WO 98/56415), Escin, Digitonin, Gypsophila or *Chenopodium quinoa* saponins. Alternatively the composition of the disclosure may be formulated with conventional vaccine vehicles composed of chitosan or other polycationic polymers, polylactide and polylactide-co-glycolide particles, poly-N-acetyl glucosamine-based polymer matrix, particles composed of polysaccharides or chemically modified polysaccharides, and lipid-based particles, etc. The composition may also be formulated in the presence of cholesterol to form particulate structures such as liposomes.

The composition may be administered to patients in an amount effective, especially to enhance an immune response in an animal or human organism. As used herein, the term "effective amount" refers to an amount sufficient to realize a desired biological effect. For example, an effective amount for enhancing an immune response could be that amount necessary to cause activation of the immune system, for instance resulting in the development of an anti-tumor response in a cancerous patient (e.g. size reduction or regression of the tumor into which the composition has been injected and/or distant tumors). The appropriate dosage may vary depending upon known factors such as the pharmacodynamic characteristics of the particular active agent, age, health, and weight of the host organism; the condition(s) to be treated, nature and extent of symptoms, kind of concurrent treatment, frequency of treatment, the need for prevention or therapy and/or the effect desired. The dosage will also be calculated dependent upon the particular route of administration selected. Further refinement of the calculations necessary to determine the appropriate dosage for treatment is routinely made by a practitioner, in the light of the relevant circumstances. The titer may be determined by conventional techniques. A composition based on vector plasmids may be formulated in the form of doses of between 1 µg to 100 mg, advantageously between 10 µg and 10 mg and typically between 100 µg and 1 mg. A composition based on proteins may be formulated in the form of doses of between 10 ng to 100 mg. A typical dose is from about 1 µg to about 10 mg of the therapeutic protein per kg body weight. The administration may take place in a single dose or a dose repeated one or several times after a certain time interval. In one typical embodiment, the composition of the present disclosure is administered by injection using conventional syringes and needles, or devices designed for ballistic delivery of solid compositions (WO 99/27961), or needleless pressure liquid jet device (U.S. Pat. No. 4,596,556; U.S. Pat. No. 5,993,412).

The composition of the disclosure can be enclosed in ampoules, disposable syringes or multiple dose vials made of glass or plastic. In all cases, the composition must be sterile and should be fluid to the extent that easy syringability exists. It must be stable under the conditions of manufacture and storage and must be preserved against the contaminating action of microorganisms such as bacteria and fungi. Sterile injectable solutions can be prepared by incorporating the active agent (e.g., a fusion protein or infectious particles) in the required amount with one or a combination of ingredients enumerated above, followed by filtered sterilization.

Methods of Use

The pharmaceutical composition of the disclosure may be employed in methods for treating or preventing a variety of diseases and pathologic conditions, including genetic diseases, congenital diseases and acquired diseases such as infectious diseases (e.g. viral and/or bacterial infections), cancer, immune deficiency diseases, and autoimmune diseases. Accordingly, the present disclosure also encompasses the use of the fusion protein, vector, infectious viral particle, host cell or composition of the disclosure for the preparation of a drug intended for treating or preventing such diseases, and especially cancer or an infectious disease.

The composition of the present disclosure is particularly intended for the preventive or curative treatment of disorders, conditions or diseases associated with cancer. The term "cancer" encompasses any cancerous conditions including diffuse or localized tumors, metastasis, cancerous polyps and preneoplastic lesions (e.g. dysplasies) as well as diseases which result from unwanted cell proliferation. A variety of tumors may be selected for treatment in accordance with the methods described herein. In general, solid tumors are typical. Cancers which are contemplated in the context of the disclosure include without limitation glioblastoma, sarcoma, melanomas, mastocytoma, carcinomas as well as breast cancer, prostate cancer, testicular cancer, ovarian cancer, endometrial cancer, cervical cancer (in particular, those induced by a papilloma virus), lung cancer (e.g. lung carcinomas including large cell, small cell, squamous and adeno-carcinomas), renal cancer, bladder cancer, liver cancer, colon cancer, anal cancer, pancreatic cancer, stomach cancer, gastrointestinal cancer, cancer of the oral cavity, larynx cancer, brain and CNS cancer, skin cancer (e.g. melanoma and non-melanoma), blood cancer (lymphomas, leukemia, especially if they have developed in solid mass), bone cancer, retinoblastoma and thyroid cancer. In one typical embodiment of the use of the disclosure, the composition is administered into or in close proximity to a solid tumor.

In certain embodiments, the disclosure contemplates uses of conjugates disclosed herein in autologous immune enhancement therapy (AIET). AIET is a treatment method in which immune or cancer cells, e.g., lymphokine-activated killer (LAK) cells, natural killer (NK) cells, cytotoxic T lymphocytes (CTLs), dendritic cells (DCs), are taken out from the body of a subject which are cultured and processed to activate them until their resistance to cancer is strengthened and then the cells are put back in the body. The cells, antibodies, and organs of the immune system work to protect and defend the body against the tumor cells. In certain embodiments, the disclosure contemplates mixing harvested cells with conjugates of GM-CSF and IL-7 to activate them. In certain embodiments, the disclosure contemplates administering conjugates of GM-CSF and IL-7 when the cells are administered back to the subject.

In certain embodiments, the disclosure contemplates the administration of sipuleucel-T (PROVENGE) in combination with a conjugate of GM-CSF and IL-7. PROVENGE consists of autologous peripheral blood mononuclear cells, including antigen presenting cells (APCs), that have been activated during a culture period with a recombinant human protein, PAP-GM-CSF, consisting of prostatic acid phosphatase (PAP), an antigen expressed in prostate cancer tissue, linked to GM-CSF. In certain embodiments, the disclosure relates to a conjugate comprising PAP, GM-CSF, and IL-7, and uses in activating antigen presenting cells in peripheral blood mononuclear cells. The peripheral blood mononuclear cells of the subject may be obtained via a standard leukapheresis procedure prior to infusion. During culture, the recombinant antigen can bind to and be processed by antigen presenting cells (APCs). The recombinant antigen is believed to direct the immune response to PAP. The infused product is believed to contain antigen presenting cells, dendritic cells, T cells, B cells, natural killer (NK) cells, and other cells. Typically each dose contains more than 50 million autologous CD54$^+$ cells activated with PAP-GM-CSF or PAP-GM-CSF-IL-7. The potency is typically evaluated by measuring the increased expression of the CD54 molecule, also known as ICAM-1, on the surface of APCs after culture with PAP-GM-CSF or PAP-CM-CSF-IL-7. CD54 is a cell surface molecule that plays a role in the immunologic interactions between APCs and T cells, and is considered a marker of immune cell activation.

In certain embodiments, the disclosure contemplates methods for treating cancer comprising administering any GM-CSF and IL-7 conjugate disclosed herein as an immune adjuvant in combination with a vector that encodes a tumor associated antigen/cancer marker, such as PSA, PAP, and optionally encoding other co-stimulatory molecules selected from, B7-1, B7-2, ICAM-1, GM-CSF, leukocyte function-associated antigen-3 (LFA-3). Other embodiments contemplated for the treatment of cancer include administering an effective amount of a vector that encodes a GM-CSF and IL-7 conjugate disclosed herein and optionally further encodes a tumor associated antigen/cancer marker and optionally encodes other co-stimulatory molecules to a subject. PROSTVAC is a recombinant vector encoding costimulatory molecules, as well as PSA as a vaccine target. Plasmid DNA is incorporated into either vaccinia or fowlpox viruses by means of a packing cell line. Patients are treated with a vaccinia prime followed by a series of fowlpox-based boosts.

In certain embodiments, the disclosure relates to methods of treating cancer comprising administering a GM-CSF and IL-7 conjugate in combination with an anti-CTLA-4 antibody. Anti-CTLA-4 antibody is contemplated to be administered in combination with any of the methods disclosed herein. It is believed that it binds to CTLA-4 surface glycoprotein on T-cell surface, minimizing immune autoregulation and potentially enhancing antitumor activity. Interactions between B7 molecules on antigen-presenting cells and CTLA-4 on tumor-specific T cells are inhibitory. Thus, CTLA-4 engagement negatively regulates the proliferation and function of such T cells. Under certain conditions, blocking CTLA-4 with a monoclonal antibody (ipilimumab or tremilimumab) restores T-cell function.

Other embodiments contemplated for the treatment of cancer include methods that utilize the extraction of cancer cells from a subject and incorporate glycosyl-phosphatidylinositol (GPI)-anchored co-stimulatory molecules such as B7-1 and B7-2 into tumor cell membranes optionally with a conjugate GM-CSF and IL-7 anchored GPI, and administering the modified cells to the subject in combination with a conjugate of GM-CSF and IL-7 to elicit an immune response. See e.g., McHugh et al., Cancer Res., 1999, 59(10):2433-7; Poloso et al., Mol. Immunol., 2002, 38(11):803-16; and Nagarajan & Selvaraj, Cancer Res., 2002, 62(10):2869-74.

Other pathologic diseases and conditions are also contemplated in the context of the disclosure, especially infectious diseases associated with an infection by a pathogen such as fungi, bacteria, protozoa and viruses. Representative examples of viral pathogens include without limitation human immunodeficiency virus (e.g. HIV-1 or HIV-2), human herpes viruses (e.g. HSV1 or HSV2), cytomegalovirus, Rotavirus, Epstein Barr virus (EBV), hepatitis virus (e.g. hepatitis B virus, hepatitis A virus, hepatitis C virus and hepatitis E virus), varicella-zoster virus (VZV), paramyxoviruses, coronaviruses; respiratory syncytial virus, parainfluenza virus, measles virus, mumps virus, flaviviruses (e.g. Yellow Fever Virus, Dengue Virus, Tick-borne encephalitis virus, Japanese Encephalitis Virus), influenza virus, and typically human papilloma viruses (e.g. HPV-6, 11, 16, 18, 31. 33). Representative examples of bacterial pathogens include *Neisseria* (e.g. *N. gonorrhea* and *N. meningitidis*); *Bordetella* (e.g. *B. pertussis, B. parapertussis* and *B. bronchiseptica*), *Mycobacteria* (e.g. *M. tuberculosis, M. bovis, M. leprae, M.*

*avium, M. paratuberculosis, M. smegmatis*); *Legionella* (e.g. *L. pneumophila*); *Escherichia* (e.g. enterotoxic *E. coli*, enterohemorragic *E. coli*, enteropathogenic *E. coli*); *Vibrio* (e.g. *V. cholera*); *Shigella* (e.g. *S. sonnei, S. dysenteriae, S. flexnerii*); *Salmonella* (e.g. *S. typhi, S. paratyphi, S. choleraesuis, S. enteritidis*); *Listeria* (e.g. *L. monocytogenes*); *Helicobacter* (e.g. *H. pylori*); *Pseudomonas* (e.g. *P. aeruginosa*); *Staphylococcus* (e.g. *S. aureus, S. epidermidis*); *Enterococcus* (e.g. *E. faecalis, E. faecium*), *Clostridium* (e.g. *C. tetani, C. botulinum, C. difficile*); *Bacillus* (e.g. *B. anthracis*); *Corynebacterium* (e.g. *C. diphtheriae*), and *Chlamydia* (e.g. *C. trachomatis, C. pneumoniae, C. psittaci*). Representative examples of parasite pathogens include *Plasmodium* (e.g. *P. falciparum*), *Toxoplasma* (e.g. *T. gondii*) *Leshmania* (e.g. *L. major*), *Pneumocystis* (e.g. *P. carinii*), *Trichomonas* (e.g. *T. vaginalis*), *Schisostoma* (e.g. *S. mansoni*). Representative examples of fungi include *Candida* (e.g. *C. albicans*) and *Aspergillus*.

Examples of autoimmune diseases include, but are not limited to, multiple sclerosis (MS), scleroderma, rheumatoid arthritis, autoimmune hepatitis, diabetes mellitus, ulcerative colitis, Myasthenia gravis, systemic lupus erythematosus, Graves' disease, idiopathic thrombocytopenia purpura, hemolytic anemia, multiple myositis/dermatomyositis, Hashimoto's disease, autoimmune hypocytosis, Sjogren's syndrome, angitis syndrome and drug-induced autoimmune diseases (e.g., drug-induced lupus).

Moreover, as mentioned above, the fusion protein, nucleic acid molecule, vector, infectious particle, host cell and/or composition of the present disclosure can be used as an adjuvant to enhance the immune response of an animal or human organism to a particular antigen. This particular use of the present disclosure may be made in combination with one or more transgenes or transgene products as defined above, e.g. for purposes of immunotherapy. Typically, the active agent (e.g. fusion protein, infectious particle or pharmaceutical composition of the disclosure) is administered in combination with one or more transgenes or transgene products. Accordingly, there is typically also provided a composition comprising in combination a transgene product (e.g. a viral antigen or a suicide gene product) and a fusion protein as well as a composition comprising vector(s) or viral particles encoding a transgene product and a fusion protein. The transgene and the fusion-encoding nucleic acid sequences may be expressed from the same vector or from separate vectors which may have the same origin (e.g. adenoviral vectors) or a different origin (e.g. a MVA vector encoding the particular antigen and an adenoviral vector encoding the fusion protein). The fusion protein and the transgene product (or their respective encoding vectors) can be introduced into the host cell or organism either concomitantly or sequentially either via the mucosal and/or systemic route.

Combination Therapies

The cancer treatments disclosed herein can be applied as a sole therapy or can involve, conventional surgery or radiotherapy, hormonal therapy, or chemotherapy. Such chemotherapy can include one or more of the following categories of anti-tumour agents:

(i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulfan and nitrosoureas); antimetabolites (for example antifolates such as fluoropyrimidines like 5-fluorouracil and gemcitabine, tegafur, raltitrexed, methotrexate, cytosine arabinoside and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin); and proteosome inhibitors (for example bortezomib [Velcade®]); and the agent anegrilide [Agrylin®]; and the agent alpha-interferon (ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) agents which inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-Her2 antibody trastuzumab and the anti-epidermal growth factor receptor (EGFR) antibody, cetuximab), farnesyl transferase inhibitors, tyrosine kinase inhibitors and serine/threonine kinase inhibitors, for example inhibitors of the epidermal growth factor family for example EGFR family tyrosine kinase inhibitors such as: N-(3-chloro-4-fluorophenyl)-7-methoxy-6-(3-morpholinopropoxy)quinazolin-4-amine (gefitinib), N-(3-ethynylphenyl)-6,7-bis(2-methoxyethoxy)quinazolin-4-amine (erlotinib), and 6-acrylamido-N-(3-chloro-4-fluorophenyl)-7-(3-morpholinopropoxy)quinazolin-4-amine (CI-1033), for example inhibitors of the platelet-derived growth factor family and for example inhibitors of the hepatocyte growth factor family, for example inhibitors of phosphotidylinositol 3-kinase (PI3K) and for example inhibitors of mitogen activated protein kinase kinase (MEK1/2) and for example inhibitors of protein kinase B (PKB/Akt), for example inhibitors of Src tyrosine kinase family and/or Abelson (Abl) tyrosine kinase family such as dasatinib (BMS-354825) and imatinib mesylate (Gleevec™); and any agents that modify STAT signalling;

(v) antiangiogenic agents such as those which inhibit the effects of vascular endothelial growth factor, (for example the anti-vascular endothelial cell growth factor antibody bevacizumab [Avastin™]) and compounds that work by other mechanisms (for example linomide, inhibitors of integrin ocvβ3 function and angiostatin);

(vi) vascular damaging agents such as Combretastatin A4;

(vii) antisense therapies, for example those which are directed to the targets listed above, such as an anti-RAS antisense; and (viii) immunotherapy approaches, including for example ex-vivo and in-vivo approaches to increase the immunogenicity of subject tumour cells, such as transfection with cytokines such as interleukin 2, interleukin 4 or granulocyte-macrophage colony stimulating factor, approaches to decrease T-cell energy, approaches using transfected immune cells such as cytokine-transfected dendritic cells, approaches using cytokine-transfected tumour cell lines and approaches using anti-idiotypic antibodies, and approaches using the immunomodulatory drugs thalidomide and lenalidomide [Revlimid®].

The combination therapy also contemplates use of the disclosed pharmaceutical compositions with radiation therapy or surgery, as an alternative, or a supplement, to a second therapeutic or chemotherapeutic agent.

A typical chronic lymphocytic leukemia (CLL) chemotherapeutic plan includes combination chemotherapy with chlorambucil or cyclophosphamide, plus a corticosteroid such as prednisone or prednisolone. The use of a corticosteroid has the additional benefit of suppressing some related autoimmune diseases, such as immunohemolytic anemia or immune-mediated thrombocytopenia. In resistant cases, single-agent treatments with nucleoside drugs such as fludarabine, pentostatin, or cladribine may be successful. Patients may consider allogeneic or autologous bone marrow transplantation. In certain embodiments, the disclosure contemplates combination treatments using conjugates disclosed herein in combination with chloroambucil, cyclophosphamide, prednisone, prednisolone, fludarabine, pentostatin, and/or cladribine or combinations thereof.

Treatment of acute lymphoblastic leukemia typically includes chemotherapy to bring about bone marrow remission. Typical regiments include prednisone, vincristine, and an anthracycline drug, L-asparaginase or cyclophosphamide. Other options include tprednisone, L-asparaginase, and vincristine. Consolidation therapy or intensification therapy to eliminate any remaining leukemia may include antimetabolite drugs such as methotrexate and 6-mercaptopurine (6-MP). In certain embodiments, the disclosure contemplates combination treatments using conjugates disclosed herein in combination with COP, CHOP, R-CHOP, imatinib, alemtuzumab, vincristine, L-asparaginase or cyclophosphamide, methotrexate and/or 6-mercaptopurine (6-MP). COP refers to a chemotherapy regimen used in the treatment of lymphoma of cyclophosphamide, vincristine, and prednisone or prednisolone and optionally hydroxydaunorubicin (CHOP) and optionally rituximab (R-CHOP).

In some embodiments, the disclosure relates to treating a viral infection by administering a GM-CSF and IL-7 conjugate in combination with a second antiviral agent. In further embodiments, a GM-CSF and IL-7 conjugate is administered in combination with one or more of the following agents: abacavir, acyclovir, acyclovir, adefovir, amantadine, amprenavir, ampligen, arbidol, atazanavir, atripla, boceprevir, cidofovir, combivir, darunavir, delavirdine, didanosine, docosanol, edoxudine, efavirenz, emtricitabine, enfuvirtide, entecavir, famciclovir, fomivirsen, fosamprenavir, foscarnet, fosfonet, ganciclovir, ibacitabine, immunovir, idoxuridine, imiquimod, indinavir, inosine, interferon type III, interferon type II, interferon type I, lamivudine, lopinavir, loviride, maraviroc, moroxydine, methisazone, nelfinavir, nevirapine, nexavir, oseltamivir (Tamiflu), peginterferon alfa-2a, penciclovir, peramivir, pleconaril, podophyllotoxin, raltegravir, ribavirin, rimantadine, ritonavir, pyramidine, saquinavir, stavudine, tenofovir, tenofovir disoproxil, tipranavir, trifluridine, trizivir, tromantadine, truvada, valaciclovir (Valtrex), valganciclovir, vicriviroc, vidarabine, viramidine zalcitabine, zanamivir (Relenza), and/or zidovudine (AZT).

Antiviral agents include, but are not limited to, protease inhibitors (PIs), integrase inhibitors, entry inhibitors (fusion inhibitors), maturation inhibitors, and reverse transcriptase inhibitors (anti-retrovirals). Combinations of antiviral agents create multiple obstacles to viral replication, i.e., to keep the number of offspring low and reduce the possibility of a superior mutation. If a mutation that conveys resistance to one of the agents being taken arises, the other agents continue to suppress reproduction of that mutation. For example, a single anti-retroviral agent has not been demonstrated to suppress an HIV infection for long. These agents are typically taken in combinations in order to have a lasting effect. As a result, the standard of care is to use combinations of anti-retrovirals.

Reverse transcribing viruses replicate using reverse transcription, i.e., the formation of DNA from an RNA template. Retroviruses often integrate the DNA produced by reverse transcription into the host genome. They are susceptible to antiviral drugs that inhibit the reverse transcriptase enzyme. In certain embodiments the disclosure relates to methods of treating viral infections by administering a GM-CSF and IL-7 conjugate, and a retroviral agent such as nucleoside and nucleotide reverse transcriptase inhibitors (NRTI) and/or a non-nucleoside reverse transcriptase inhibitors (NNRTI). Examples of nucleoside reverse transcriptase inhibitors include zidovudine, didanosine, zalcitabine, stavudine, lamivudine, abacavir, emtricitabine, entecavir, apricitabine. Examples of nucleotide reverse transcriptase inhibitors include tenofovir and adefovir. Examples of non-nucleoside reverse transcriptase inhibitors include efavirenz, nevirapine, delavirdine, and etravirine.

In certain embodiments, the disclosure relates to methods of treating a viral infection by administering a GM-CSF and IL-7 conjugate in combination with an antiviral drug, e.g., 2',3'-dideoxyinosine and a cytostatic agent, e.g., hydroxyurea.

Human immunoglobulin G (IgG) antibodies are believed to have opsonizing and neutralizing effects against certain viruses. IgG is sometimes administered to a subject diagnosed with immune thrombocytopenic purpura (ITP) secondary to a viral infection since certain viruses such as, HIV and hepatitis, cause ITP. In certain embodiments, the disclosure relates to methods of treating or preventing viral infections comprising administering a GM-CSF and IL-7 conjugate in combination with an immunoglobulin to a subject. IgG is typically manufactured from large pools of human plasma that are screened to reduce the risk of undesired virus transmission. The Fc and Fab functions of the IgG molecule are usually retained. Therapeutic IgGs include Privigen, Hizentra, and WinRho. WinRho is an immunoglobulin (IgG) fraction containing antibodies to the Rho(D) antigen (D antigen). The antibodies have been shown to increase platelet counts in Rho(D) positive subjects with ITP. The mechanism is thought to be due to the formation of anti-Rho(D) (anti-D)-coated RBC complexes resulting in Fc receptor blockade, thus sparing antibody-coated platelets.

In some embodiments, the disclosure relates to treating a bacterial infection by administering a GM-CSF and IL-7 conjugate in combination with an antibiotic drug. In further embodiments, the subject is co-administered with an antibiotic selected from the group comprising of Sulfonamides, Diaminopyrimidines, Quinolones, Beta-lactam antibiotics, Cephalosporins, Tetracyclines, Notribenzene derivatives, Aminoglycosides, Macrolide antibiotics, Polypeptide antibiotics, Nitrofuran derivatives, Nitroimidazoles, Nicotinin acid derivatives, Polyene antibiotics, Imidazole derivatives or Glycopeptide, Cyclic lipopeptides, Glycylcyclines and Oxazolidinones. In further embodiments, these antibiotics include but are not limited to Sulphadiazine, Sulfones—[Dapsone (DDS) and Paraminosalicyclic (PAS)], Sulfanilamide, Sulfamethizole, Sulfamethoxazole, Sulfapyridine, Trimethoprim, Pyrimethamine, Nalidixic acids, Norfloxacin, Ciproflaxin, Cinoxacin, Enoxacin, Gatifloxacin, Gemifloxacin, Grepafloxacin, Levofloxacin, Lomefloxacin, Moxifloxacin, Ofloxacin, Pefloxacin, Sparfloxacin, Trovafloxacin, Penicillins (Amoxicillin, Ampicillin, Azlocillin, Carbenicillin, Cloxacillin, Dicloxacillin, Flucloxacillin, Hetacillin, Oxacillin, Mezlocillin, Penicillin G, Penicillin V, Piperacillin), Cephalosporins (Cefacetrile, Cefadroxil, Cefalexin, Cefaloglycin, Cefalonium, Cefaloridin, Cefalotin, Cefapirin, Cefatrizine, Cefazaflur, Cefazedone, Cefazolin, Cefradine, Cefroxadine, Ceftezole, Cefaclor, Cefonicid, Ceforanide, Cefprozil, Cefuroxime, Cefuzonam, Cefmetazole, Cefoteta, Cefoxitin, Cefcapene, Cefdaloxime, Cefdinir, Cefditoren, Cefetamet, Cefixime, Cefinenoxime, Cefodizime, Cefoperazone, Cefotaxime, Cefotiam, Cefpimizole, Cefpiramide, Cefpodoxime, Cefteram, Ceftibuten, Ceftiofur, Ceftiolen, Ceftizoxime, Ceftriaxone, Cefoperazone, Ceftazidime, Cefepime), Moxolactam, Carbapenems (Imipenem, Ertapenem, Meropenem) Monobactams (Aztreonam) Oxytetracycline, Chlortetracycline, Clomocycline, Demeclocycline, Tetracycline, Doxycycline, Lymecycline, Meclocycline, Methacycline, Minocycline, Rolitetracycline, Chloramphenicol, Amikacin, Gentamicin, Framycetin, Kanamycin, Neomicin, Neomycin, Netilmicin, Streptomycin, Tobramycin, Azithromycin, Clarithromycin, Dirithromycin, Erythromycin, Roxithromycin, Telithromycin, Polymyxin-B, Colistin, Bacitracin, Tyrothricin Notrifurantoin, Furazolidone, Metronidazole, Timidazole, Isoniazid, Pyrazinamide, Ethionamide, Nystatin, Amphotericin-B, Hamycin, Miconazole, Clotrimazole, Ketoconazole, Fluconazole, Rifampacin, Lincomycin, Clindamycin, Spectinomycin, Chloramphenicol, Clindamycin, Colistin, Fosfomycin, Loracarbef, Metronidazole, Nitrofurantoin, Polymyxin B, Polymyxin B Sulfate, Procain, Spectinomycin, Timidazole, Trimethoprim, Ramoplanin, Teicoplanin, Vancomycin, Trimethoprim, Sulfamethoxazole, and/or Nitrofurantoin.

Vectors

The term "vector" as used herein refers to both expression and non-expression vectors and includes viral as well as non-viral vectors, including autonomous self-replicating circular plasmids. Where a recombinant microorganism or cell culture is described as hosting an "expression vector," this includes both extra-chromosomal circular DNA and DNA that has been incorporated into the host chromosome(s). Typical vectors of the disclosure are expression vectors. An expression vector contains multiple genetic elements positionally and sequentially oriented, i.e., operatively linked with other necessary elements such that nucleic acid molecule in the vector encoding the fusion proteins of the disclosure can be transcribed, and when necessary, translated in the host cells.

Any type of vector can be used in the context of the present disclosure, whether of plasmid or viral origin, whether it is an integrating or non-integrating vector. Such vectors are commercially available or described in the literature. Contemplated in the context of the disclosure are vectors for use in gene therapy (i.e. which are capable of delivering the nucleic acid molecule to a target cell) as well as expression vectors for use in recombinant techniques (i.e. which are capable for example of expressing the nucleic acid molecule of the disclosure in cultured host cells).

The vectors of the disclosure can function in prokaryotic or eukaryotic cells or in both (shuttle vectors). Suitable vectors include without limitation vectors derived from bacterial plasmids, bacteriophages, yeast episomes, artificial chromosomes, such as BAC, PAC, YAC, or MAC, and vectors derived from viruses such as baculoviruses, papovaviruses (e.g. SV40), herpes viruses, adenoviruses, adenovirus-associated viruses (AAV), poxviruses, foamy viruses, and retroviruses. Vectors may also be derived from combinations of these sources such as those derived from plasmid and bacteriophage genetic elements, e.g. cosmids and phagemids. Viral vectors can be replication-competent, conditionally replicative or replication-defective. In the case in which viral replication is defective, replication will occur in host cells providing functions that complement the defects.

Examples of suitable plasmids include but are not limited to those derived from pBR322 (Gibco BRL), pUC (Gibco BRL), pBluescript (Stratagene), p Poly (Lathe et al., 1987, Gene 57, 193-201), pTrc (Amann et al., 1988, Gene 69, 301-315) and pET 11d (Studier et al., 1990, Gene Expression Technology: Methods in Enzymology 185, 60-89). It is well known that the four of the plasmid can affect the expression efficiency, and it is typical that a large fraction of the vector be in supercoiled form. Examples of vectors for expression in yeast (e.g. *S. cerevisiae*) include pYepSec1 (Baldari et al., 1987, EMBO J. 6, 229-234), pMFa (Kujan et al., 1982, Cell 30, 933-943), pJRY88 (Schultz et al., 1987, Gene 54, 113-123), and pYES2 (Invitrogen Corporation, San Diego, Calif.). The vectors of the disclosure can also be derived from baculoviruses to be expressed in cultured insect cells (e.g. Sf 9 cells).

According to a typical embodiment of the disclosure, the nucleic acid molecules described herein are expressed by using mammalian expression vectors. Examples of mammalian expression vectors include pREP4, pCEP4 (Invitrogene), pCI (Promega), pCDM8 (Seed, 1987, Nature 329, 840) and pMT2PC (Kaufman et al., 1987, EMBO J. 6, 187-195). The expression vectors listed herein are provided by way of example only of some well-known vectors available to those of ordinary skill in the art. The person of ordinary skill in the art would be aware of other vectors suitable for maintenance, propagation or expression of the nucleic acid molecules described herein.

Moreover, the vector of the present disclosure may also comprise a marker gene in order to select or to identify the transfected cells (e.g. by complementation of a cell auxotrophy or by antibiotic resistance), stabilizing elements (e.g. cer sequence; Summers and Sherrat, 1984, Cell 36, 1097-1103), integrative elements (e.g. LTR viral sequences and transposons) as well as elements providing a self-replicating function and enabling the vector to be stably maintained in cells, independently of the copy number of the vector in the cell. Markers include tetracycline or ampicillin-resistance genes for prokaryotic host cells and dihydrofolate reductase or neomycin resistance for eukaryotic host cells. However, any marker that provides selection for a phenotypic trait will be effective. The self-replicating function may be provided by using a viral origin of replication and providing one or more viral replication factors that are required for replication mediated by that particular viral origin (WO 95/32299). Origins of replication and any replication factors may be obtained from a variety of viruses, including Epstein-Barr virus (EBV), human and bovine papilloma viruses and papovavirus BK.

Typical vectors of the present disclosure are viral vectors and especially adenoviral vectors, which have a number of well-documented advantages as vectors for gene therapy. The adenoviral genome consists of a linear double-stranded DNA molecule of approximately 36 kb carrying more than about thirty genes necessary to complete the viral cycle. The early genes are divided into 4 regions (E1 to E4) that are essential for viral replication (Pettersson and Roberts, 1986, In Cancer Cells (Vol 4): DNA Tumor Viruses, Botchan and Glodzicker Sharp Eds pp 37-47, Cold Spring Harbor Laboratory, Cold Spring Harbor, N.Y.; Halbert et al., 1985, J. Virol. 56, 250-257) with the exception of the E3 region, which is believed dispensable for viral replication based on the observation that naturally-occurring mutants or hybrid viruses deleted within the E3 region still replicate like wild-type viruses in cultured cells (Kelly and Lewis, 1973, J. Virol. 12, 643-652). The E1 gene products encode proteins responsible for the regulation of transcription of the viral genome. The E2 gene products are required for initiation and chain elongation in viral DNA synthesis. The proteins encoded by the E3 prevent cytolysis by cytotoxic T cells and tumor necrosis factor (Wold and Gooding, 1991, Virology 184, 1-8). The proteins encoded by the E4 region are involved in DNA replication, late gene expression and splicing and host cell shut off (Halbert et al., 1985, J. Virol. 56, 250-257). The late genes (L1 to L5) encode in their majority the structural proteins constituting the viral capsid. They overlap at least in part with the early transcription units and are transcribed from a unique promoter (MLP for Major Late Promoter). In addition, the adenoviral genome carries at both extremities cis-acting 5' and 3' ITRs (Inverted Terminal Repeat) and the encapsidation region, both essential for DNA replication. The ITRs harbor origins of DNA replication whereas the encapsidation region is required for the packaging of adenoviral DNA into infectious particles.

The adenoviral vectors for use in accordance with the present disclosure, typically infects mammalian cells. It can be derived from any human or animal source, in particular canine (e.g. CAV-1 or CAV-2; Genbank ref CAV1GENOM and CAV77082 respectively), avian (Genbank ref AAVEDS-DNA), bovine (such as BAV3; Seshidhar Reddy et al., 1998, J. Virol. 72, 1394-1402), murine (Genbank ref ADRMUS-MAV1), ovine, feline, porcine or simian adenovirus or alternatively from a hybrid thereof. Any serotype can be employed from the adenovirus serotypes 1 through 51. For instance, an adenovirus can be of subgroup A (e.g. serotypes 12, 18, and 31), subgroup B (e.g. serotypes 3, 7, 11, 14, 16, 21, 34, and 35), subgroup C (e.g. serotypes 1, 2, 5, and 6), subgroup D (e.g. serotypes 8, 9, 10, 13, 15, 17, 19, 20, 22-30, 32, 33, 36-39, and 42-47), subgroup E (serotype 4), subgroup F (serotypes 40 and 41), or any other adenoviral serotype. However, the human adenoviruses of the B or C sub-group are typical and especially adenoviruses 2 (Ad2), 5 (Ad5) and 35 (Ad35). Generally speaking, adenoviral stocks that can be employed as a source of the cited adenovirus are currently available from the American Type Culture Collection (ATCC, Rockville, Md.), or from any other source. Moreover, such adenoviruses have been the subject of numerous publications describing their sequence, organization and biology, allowing the artisan to apply them. Adenoviral vectors, methods of producing adenoviral vectors, and methods of using adenoviral vectors are disclosed, for example in U.S. Pat. No. 6,133,028, U.S. Pat. No. 6,040,174, U.S. Pat. No. 6,110,735, U.S. Pat. No. 6,399,587, WO 00/50573 and EP 1016711 for group C adenoviral vectors and for example in U.S. Pat. No. 6,492,169 and WO 02/40665 for non-group C adenoviral vectors.

In certain embodiments, the adenoviral vector of the present disclosure is replication-competent. The term "replication-competent" as used herein refers to an adenoviral vector capable of replicating in a host cell in the absence of any trans-complementation. In the context of the present disclosure, this term also encompasses replication-selective or conditionally-replicative adenoviral vectors which are engineered to replicate better or selectively in cancer or hyperproliferative host cells. Examples of such replication-competent adenoviral vectors are well known in the art and readily available to those skill in the art (see, for example, Hernandez-Alcoceba et al., 2000, Human Gene Ther. 11, 2009-2024; Nemunaitis et al., 2001, Gene Ther. 8, 746-759; Alemany et al., 2000, Nature Biotechnology 18, 723-727).

Replication-competent adenoviral vectors according to the disclosure can be a wild-type adenovirus genome or can be derived therefrom by introducing modifications into the viral genome, e.g., for the purpose of generating a conditionally-replicative adenoviral vector. Such modification(s) include the deletion, insertion and/or mutation of one or more nucleotide(s) in the coding sequences and/or the regulatory sequences. Typical modifications are those that render said replication-competent adenoviral vector dependent on cellular activities specifically present in a tumor or cancerous cell. In this regard, viral gene(s) that become dispensable in tumor cells, such as the genes responsible for activating the cell cycle through p53 or Rb binding, can be completely or partially deleted or mutated. By way of illustration, such conditionally-replicative adenoviral vectors can be engineered by the complete deletion of the adenoviral MB gene encoding the 55 kDa protein or the complete deletion of the MB region to abrogate p53 binding (see for example U.S. Pat. No. 5,801,029 and U.S. Pat. No. 5,846,945). This prevents the virus from inactivating tumor suppression in normal cells, which means that the virus cannot replicate. However, the virus will replicate and lyse cells that have shut off p53 or Rb expression through oncogenic transformation. As another example, the complete deletion of the E1A region makes the adenoviral vector dependent on intrinsic or IL-6-induced E1A-like activities. Optionally, an inactivating mutation may also be introduced in the E1A region to abrogate binding to the Rb. Rb defective mutation/deletion is typically introduced within the E1A CR1 and/or CR2 domain (see for example WO00/24408). In a second strategy optionally or in combination to the first approach, native viral promoters controlling transcription of the viral genes can be replaced with tissue or tumor-specific promoters. By way of illustration, regulation of the E1A and/or the E1B genes can be placed under the control of a tumor-specific promoter such as the PSA, the kallikrein, the probasin, the AFP, the α-fetoprotein or the telomerase reverse transcriptase (TERT) promoter (see for example U.S. Pat. No. 5,998,205, WO 99/25860, U.S. Pat. No. 5,698,443 and WO 00/46355) or a cell-cycle specific promoter such as E2F-1 promoter (WO00/15820 and WO01/36650). Typical in this context is the exemplary vector designated ONYX-411 which combines a Rb defective deletion of 8 amino acid residues within the MA CR2 domain and the use of E2F-1 promoter to control expression of both the E1A and E4 viral genes.

In certain embodiments, the adenoviral vector of the disclosure is replication-defective. Replication-defective adenoviral vectors are known in the art and can be defined as being deficient in one or more regions of the adenoviral genome that are essential to the viral replication (e.g., E1, E2 or E4 or combination thereof), and thus unable to propagate in the absence of trans-complementation (e.g., provided by either complementing cells or a helper virus). The replication-defective phenotype is obtained by introducing modifications in the viral genome to abrogate the function of one or more viral gene(s) essential to the viral replication. Typical replication-defective vectors are E1-deleted, and thus defective in E1 function. Such E1-deleted adenoviral vectors include those described in U.S. Pat. No. 6,063,622; U.S. Pat. No. 6,093,567; WO 94/28152; WO 98/55639 and EP 974 668 (the disclosures of all of these publications are hereby incorporated herein by reference). A typical E1 deletion covers approximately the nucleotides (nt) 459 to 3328 or 459 to 3510, by reference to the sequence of the human adenovirus type 5 (disclosed in the Genbank under the accession number M 73260 and in Chroboczek et al., 1992, Virol. 186, 280-285).

Furthermore, the adenoviral backbone of the vector may comprise modifications (e.g. deletions, insertions or mutations) in additional viral region(s), to abolish the residual synthesis of the viral antigens and/or to improve long-term expression of the nucleic acid molecules in the transduced cells (see for example WO 94/28152; Lusky et al., 1998, J. Virol 72, 2022-2032; Yeh et al., 1997, FASEB J. 11, 615-623). In this context, the present disclosure contemplates the use of adenoviral vectors lacking E1, or E1 and E2, or E1 and E3, or E1 and E4, or E1 and E2 and E3, or E1 and E2 and E4, or E1 and E3 and E4, or E1 and E2 and E3 and E4 functions. An adenoviral vector defective for E2 function may be deleted of all or part of the E2 region (typically within the E2A or alternatively within the E2B or within both the E2A and the E2B regions) or comprises one or more mutations, such as the thermosensitive mutation of the DBP (DNA Binding Protein) encoding gene (Ensinger et al., J. Virol. 10 (1972), 328-339). The adenoviral vector may also be deleted of all or part of the E4 region (see, for example, EP 974 668 and WO 00/12741). An exemplary E4 deletion covers approximately the nucleotides from position 32994 to position 34998, by reference to the sequence of the human adenovirus type 5. In addition, deletions within the non-essential E3 region (e.g. from Ad5 position 28597 to position 30469) may increase the cloning capacity, but it may be advantageous to retain the E3 sequences coding for gp19k, 14.7K and/or RID allowing to escape the host immune system (Gooding et al., 1990, Critical Review of Immunology 10, 53-71) and inflammatory reactions (EP 00 440 267.3). It is also conceivable to employ a minimal (or gutless) adenoviral vector which lacks all functional genes including early (E1, E2, E3 and E4) and late genes (L1, L2, L3, L4 and L5) with the exception of cis-acting sequences (see for example Kovesdi et al., 1997, Current Opinion in Biotechnology 8, 583-589; Yeh and Perricaudet, 1997, FASEB 11, 615-623; WO 94/12649; and WO 94/28152). The replication-deficient adenoviral vector may be readily engineered by one skilled in the art, taking into consideration the required minimum sequences, and is not limited to these exemplary embodiments.

The nucleic acid molecule of the present disclosure can be inserted in any location of the adenoviral genome, with the exception of the cis-acting sequences. Typically, it is inserted in replacement of a deleted region (E1, E3 and/or E4), with a special preference for the deleted E1 region. In addition, the expression cassette may be positioned in sense or antisense orientation relative to the natural transcriptional direction of the region in question.

A retroviral vector is also suitable in the context of the present disclosure. Retroviruses are a class of integrative viruses which replicate using a virus-encoded reverse transcriptase, to replicate the viral RNA genome into double stranded DNA which is integrated into chromosomal DNA of the infected cells. The numerous vectors described in the literature may be used within the framework of the present disclosure and especially those derived from murine leukemia viruses, especially Moloney (Gilboa et al., 1988, Adv. Exp. Med. Biol. 241, 29) or Friend's FB29 strains (WO 95/01447). Generally, a retroviral vector is deleted of all or part of the viral genes gag, pol and env and retains 5' and 3' LTRs and an encapsidation sequence. These elements may be modified to increase expression level or stability of the retroviral vector. Such modifications include the replacement of the retroviral encapsidation sequence by one of a retrotransposon such as VL30 (U.S. Pat. No. 5,747,323). The nucleic acid molecule of the disclosure can be inserted downstream of the encapsidation sequence, typically in opposite direction relative to the retroviral genome.

A poxyiral vector is also suitable in the context of the present disclosure. Poxviruses are a group of complex enveloped viruses that distinguish from the above-mentioned viruses by their large DNA genome and their cytoplasmic site of replication. The genome of several members of poxyiridae has been mapped and sequenced. It is a double-stranded DNA of approximately 200 kb coding for about 200 proteins of which approximately 100 are involved in virus assembly. In the context of the present disclosure, a poxyiral vector may be obtained from any member of the poxyiridae, in particular canarypox, fowlpox and vaccinia virus, the latter being typical. Suitable vaccinia viruses include without limitation the Copenhagen strain (Goebel et al., 1990, Virol. 179, 247-266 and 517-563; Johnson et al., 1993, Virol. 196, 381-401), the Wyeth strain and the modified Ankara (MVA) strain (Antoine et al., 1998, Virol. 244, 365-396). The general conditions for constructing poxvirus comprising a nucleic acid molecule are well known in the art (see for example EP 83 286; EP 206 920 for Copenhagen vaccinia viruses and Mayr et al., 1975, Infection 3, 6-14; Sutter and Moss, 1992, Proc. Natl. Acad. Sci. USA 89, 10847-10851, U.S. Pat. No. 6,440,422 for MVA viruses). The nucleic acid molecule of the present disclosure is typically inserted within the poxyiral genome in a non-essential locus, such as non-coding intergenic regions or any gene for which inactivation or deletion does not significantly impair viral growth and replication. Thymidine kinase gene is particularly appropriate for insertion in Copenhagen vaccinia viruses (Hruby et al., 1983, Proc. Natl. Acad. Sci. USA 80, 3411-3415; Weir et al., 1983, J. Virol. 46, 530-537). As far as MVA is concerned, insertion of the nucleic acid molecule can be performed in any of the excisions I to VII, and typically in excision II or III (Meyer et al., 1991, J. Gen. Virol. 72, 1031-1038; Sutter et al., 1994, Vaccine 12, 1032-1040) or in D4R locus. For fowlpox virus, although insertion within the thymidine kinase gene may be considered, the nucleic acid molecule is typically introduced into a non-coding intergenic region (see for example EP 314 569 and U.S. Pat. No. 5,180, 675). One may also envisage insertion in an essential viral locus provided that the defective function be supplied in trans, via a helper virus or by expression in the producer cell line. Suitable poxyiral vectors can be readily generated from wild type poxviruses available in recognized collections such as ATCC (fowlpox ATCC VR-251, monkey pox ATCC VR-267, swine pox ATCC VR-363, canarypox ATCC VR-111, cowpox ATCC VR-302) or ICTV (Can berra, Australia) (Copenhagen virus code 58.1.1.0.001; GenBank accession number M35027).

In certain embodiments, the vectors of the disclosure comprise the nucleic acid molecule of the disclosure in a form suitable for its expression in a host cell or organism, which means that the nucleic acid molecule is placed under the control of one or more regulatory sequences, selected on the basis of the vector type and/or host cell, which is operatively linked to the nucleic acid molecule to be expressed. As used herein, the term "regulatory sequence" refers to any sequence that allows, contributes or modulates the functional regulation of the nucleic acid molecule, including replication, duplication, transcription, splicing, translation, stability and/or transport of the nucleic acid or one of its derivative (i.e. mRNA) into the host cell or organism. In the context of the disclosure, this term encompasses promoters, enhancers and other expression control elements (e.g., polyadenylation signals and elements that affect mRNA stability). "Operably linked" is intended to mean that the nucleic acid molecule of interest is linked to the regulatory sequence(s) in a manner which allows for expression of the nucleic acid molecule (e.g., in a host cell or organism). It will be appreciated by those skilled in the art that the design of the expression vector can depend on such factors as the choice of the host cell to be transformed, the level of expression of protein desired, etc.

Regulatory sequences include promoters which direct constitutive expression of a nucleic acid molecule in many types of host cell and those which direct expression of the nucleotide sequence only in certain host cells (e.g., tissue-specific regulatory sequences) or in response to specific events or exogenous factors (e.g. by temperature, nutrient additive, hormone or other ligand).

Suitable regulatory sequences useful in the context of the present disclosure include, but are not limited to, the left promoter from bacteriophage lambda, the lac, TRP, and TAC promoters from *E. coli*, the early and late promoters from SV40, the cytomegalovirus (CMV) immediate early promoter or enhancer (Boshart et al., 1985, Cell 41, 521-530), the adenovirus early and late promoters, the phosphoglycero kinase (PGK) promoter (Hitzeman et al., 1983, Science 219, 620-625; Adra et al., 1987, Gene 60, 65-74), the thymidine kinase (TK) promoter of herpes simplex virus (HSV)-1 and retroviral long-terminal repeats (e.g. MoMuLV and Rous sarcoma virus (RSV) LTRs). Suitable promoters useful to drive expression of the nucleic acid molecule of the disclosure in a poxyiral vector include the 7.5K, H5R, TK, p28, p11 or K1L promoters of vaccinia virus. Alternatively, one may use a synthetic promoter such as those described in Chakrabarti et al. (1997, Biotechniques 23, 1094-1097), Hammond et al. (1997, J. Virological Methods 66, 135-138) and Kumar and Boyle (1990, Virology 179, 151-158) as well as chimeric promoters between early and late poxyiral promoters.

Inducible promoters are regulated by exogenously supplied compounds, and include, without limitation, the zinc-inducible metallothionein (MT) promoter (Mc Ivor et al., 1987, Mol. Cell. Biol. 7, 838-848), the dexamethasone (Dex)-inducible mouse mammary tumor virus (MMTV) promoter, the T7 polymerase promoter system (WO 98/10088), the ecdysone insect promoter (No et al., 1996, Proc. Natl. Acad. Sci. USA 93, 3346-3351), the tetracycline-repressible promoter (Gossen et al., 1992, Proc. Natl. Acad. Sci. USA 89, 5547-5551), the tetracycline-inducible promoter (Kim et al., 1995, J. Virol. 69, 2565-2573), the RU486-inducible promoter (Wang et al., 1997, Nat. Biotech. 15, 239-243 and Wang et al., 1997, Gene Ther. 4, 432-441) and the rapamycin-inducible promoter (Magari et al., 1997, J. Clin. Invest. 100, 2865-2872).

The regulatory sequences in use in the context of the present disclosure can also be tissue-specific to drive expression of the nucleic acid molecule in the tissues where therapeutic benefit is desired. Exemplary liver-specific regulatory sequences include but are not limited to those of HMG-CoA reductase (Luskey, 1987, Mol. Cell. Biol. 7, 1881-1893); sterol regulatory element 1 (SRE-1; Smith et al., 1990, J. Biol. Chem. 265, 2306-2310); albumin (Pinkert et al., 1987, Genes Dev. 1, 268-277); phosphoenol pyruvate carboxy kinase (PEPCK) (Eisenberger et al., 1992, Mol. Cell. Biol. 12, 1396-1403); human C-reactive protein (CRP) (Li et al., 1990, J. Biol. Chem. 265, 4136-4142); human glucokinase (Tanizawa et al., 1992, Mol. Endocrinology. 6, 1070-1081); cholesterol 7-alpha hydroylase (CYP-7) (Lee et al., 1994, J. Biol. Chem. 269, 14681-14689); alpha-1 antitrypsin (Ciliberto et al., 1985, Cell 41, 531-540); insulin-like growth factor binding protein (IGFBP-1) (Babajko et al., 1993, Biochem Biophys. Res. Comm. 196, 480-486); human transferrin (Mendelzon et al., 1990, Nucl. Acids Res. 18, 5717-5721); collagen type I (Houglum et al., 1994, J. Clin. Invest. 94, 808-814) and FIX (U.S. Pat. No. 5,814,716) genes. Exemplary prostate-specific regulatory sequences include but are not limited to those of the prostatic acid phosphatase (PAP) (Balms et al., 1994, Biochim. Biophys. Acta. 1217, 188-194); prostatic secretory protein 94 (PSP 94) (Nolet et al., 1991, Biochim. Biophys. Acta 1089, 247-249); prostate specific antigen complex (Kasper et al., 1993, J. Steroid Biochem. Mol. Biol. 47, 127-135); human glandular kallikrein (hgt-1) (Lilja et al., 1993, World J. Urology 11, 188-191) genes. Exemplary pancreas-specific regulatory sequences include but are not limited to those of pancreatitis associated protein promoter (Dusetti et al., 1993, J. Biol. Chem. 268, 14470-14475); elastase 1 transcriptional enhancer (Kruse et al., 1993, Genes and Development 7, 774-786); pancreas specific amylase and elastase enhancer/promoter (Wu et al., 1991, Mol. Cell. Biol. 11, 4423-4430; Keller et al., 1990, Genes & Dev. 4, 1316-1321); pancreatic cholesterol esterase gene promoter (Fontaine et al., 1991, Biochemistry 30, 7008-7014) and the insulin gene promoter (Edlund et al., 1985, Science 230, 912-916). Exemplary neuron-specific regulatory sequences include but are not limited to neuron-specific enolase (NSE) (Forss-Petter et al., 1990, Neuron 5, 187-197) and the neurofilament (Byrne and Ruddle, 1989, Proc. Natl. Acad. Sci. USA 86, 5473-5477) gene promoters. Exemplary regulatory sequences for expression in the brain include but are not limited to the neurofilament heavy chain (NF—H) promoter (Schwartz et al., 1994, J. Biol. Chem. 269, 13444-13450). Exemplary lymphoid-specific regulatory sequences include but are not limited to the human CGL1/granzyme B promoter (Hanson et al., 1991, J. Biol. Chem. 266, 24433-24438); terminal deoxy transferase (TdT), lymphocyte specific tyrosine protein kinase (p56lck) promoters (Lo et al., 1991, Mol. Cell. Biol. 11, 5229-5243); the human CD2 promoter/enhancer (Lake et al., 1990, EMBO J. 9, 3129-3136), the human NK and T cell specific activation (NKG5) (Houchins et al., 1993, Immunogenetics 37, 102-107), T cell receptor (Winoto and Baltimore, 1989, EMBO J. 8, 729-733) and immunoglobulin (Banerji et al., 1983, Cell 33, 729-740; Queen and Baltimore, 1983, Cell 33, 741-748) promoters. Exemplary colon-specific regulatory sequences include but are not limited to pp 60c-src tyrosine kinase (Talamonti et al., 1993, J. Clin. Invest 91, 53-60); organ-specific neoantigens (OSNs), mw 40 kDa (p40) (Ilantzis et al., 1993, Microbiol. Immunol. 37, 119-128); and colon specific antigen-P promoter (Sharkey et al., 1994, Cancer 73, 864-877) promoters. Exemplary regulatory sequences for expression in mammary gland and breast cells include but are not limited to the human alpha-lactalbumin (Thean et al., 1990, British J. Cancer. 61, 773-775) and milk whey (U.S. Pat. No. 4,873,316) promoters. Exemplary muscle-specific regulatory sequences include but are not limited to SM22 (WO 98/15575; WO 97/35974), the desmin (WO 96/26284), mitochondrial creatine kinase (MCK) promoters, and the chimeric promoter disclosed in EP 1310561. Exemplary lung-specific regulatory sequences include but are not limited to the CFTR and surfactant promoters.

Additional promoters suitable for use in this disclosure can be taken from genes that are preferentially expressed in proliferative tumor cells. Such genes can be identified for example by display and comparative genomic hybridization (see for example U.S. Pat. Nos. 5,759,776 and 5,776,683). Exemplary tumor specific promoters include but are not limited to the promoters of the MUC-1 gene overexpressed in breast and prostate cancers (Chen et al., 1995, J. Clin. Invest. 96, 2775-2782), of the Carcinoma Embryonic Antigen (CEA)-encoding gene overexpressed in colon cancers (Schrewe et al., 1990, Mol. Cell. Biol. 10, 2738-2748), of the ERB-2 encoding gene overexpressed in breast and pancreas cancers (Harris et al., 1994, Gene Therapy 1, 170-175), of the alpha-foetoprotein gene overexpressed in liver cancers (Kanai et al., 1997, Cancer Res. 57, 461-465), of the telomerase reverse transcriptase (TERT) (WO99/27113, WO 02/053760 and Horikawa et al., 1999, Cancer Res. 59, 826), hypoxia-responsive element (HRE), autocrine motility factor receptor, L plasmin and hexokinase II.

Those skilled in the art will appreciate that the regulatory elements controlling the expression of the nucleic acid molecule of the disclosure may further comprise additional elements for proper initiation, regulation and/or termination of transcription and translation into the host cell or organism. Such additional elements include but are not limited to non-coding exon/intron sequences, transport sequences, secretion signal sequences, nuclear localization signal sequences, IRES, polyA transcription termination sequences, tripartite leader sequences, sequences involved in replication or integration. Illustrative examples of introns suitable in the context of the disclosure include those isolated from the genes encoding alpha or beta globin (i.e. the second intron of the rabbit beta globin gene; Green et al., 1988, Nucleic Acids Res. 16, 369; Karasuyama et al., 1988, Eur. J. Immunol. 18, 97-104), ovalbumin, apolipoprotein, immunoglobulin, factor IX, and factor VIII, the SV40 16S/19S intron (Okayma and Berg, 1983, Mol. Cell. Biol. 3, 280-289) as well as synthetic introns such as the intron present in the pCI vector (Promega Corp, pCI mammalian expression vector E1731) made of the human beta globin donor fused to the mouse immunoglobin. Where secretion of the fusion protein is desired, appropriate secretion signals are incorporated into the vector. The signal sequence can be endogenous to the fusion protein or heterologous to both entities involved in the fusion protein. The person of ordinary skill in the art would be aware of the numerous regulatory sequences that are useful in expression vectors.

In addition, the vector of the disclosure can further comprise one or more transgenes (i.e. a gene of interest to be expressed together with the nucleic acid molecule of the disclosure in a host cell or organism). Desirably, the expression of the transgene has a therapeutic or protective activity to the disease or illness condition for which the vector of the present disclosure is being given. Suitable transgenes include without limitation genes encoding (i) tumor proliferation inhibitors and/or (ii) at least one specific antigen against which an immune response is desired. In a typical form of the present disclosure, the transgene product and the fusion protein act synergistically in the induction of immune responses or in providing a therapeutic (e.g. antitumoral) benefit. Accordingly, such combinations are not only suitable for immunoprophylaxis of diseases, but surprisingly also for immunotherapy of diseases such as viral, bacterial or parasitic infections, and also chronic disorders such as cancers.

Tumor proliferation inhibitors act by directly inhibiting cell growth, or killing the tumor cells. Representative examples of tumor proliferation inhibitors include toxins and suicide genes. Representative examples of toxins include without limitation ricin (Lamb et al., 1985, Eur. J. Biochem. 148, 265-270), diphtheria toxin (Tweten et al., 1985, J. Biol. Chem. 260, 10392-10394), cholera toxin (Mekalanos et al., 1983, Nature 306, 551-557; Sanchez and Holmgren, 1989, Proc. Natl. Acad. Sci. USA 86, 481-485), gelonin (Stirpe et al., 1980, J. Biol. Chem. 255, 6947-6953), antiviral protein (Barbieri et al., 1982, Biochem. J. 203, 55-59; Irvin et al., 1980, Arch. Biochem. Biophys. 200, 418-425), tritin, *Shigella* toxin (Calderwood et al., 1987, Proc. Natl. Acad. Sci. USA 84, 4364-4368; Jackson et al., 1987, Microb. Path. 2, 147-153) and *Pseudomonas* exotoxin A (Carroll and Collier, 1987, J. Biol. Chem. 262, 8707-8711).

Specific antigens are typically those susceptible to confer an immune response, specific and/or nonspecific, antibody and/or cell-mediated, against a given pathogen (virus, bacterium, fungus or parasite) or against a non-self antigen (e.g. a tumor-associated antigen). Typically, the selected antigen comprises an epitope that binds to, and is presented onto the cell surface by MHC class I proteins. Representative examples of specific antigens include without limitation: antigen(s) of the Hepatitis B surface antigen are well known in the art and include, inter alia, those PreS1, Pars2 S antigens set forth described in European Patent applications EP 414 374; EP 304 578, and EP 198 474. Antigens of the Hepatitis C virus including any immunogenic antigen or fragment thereof selected from the group consisting of the Core (C), the envelope glycoprotein E1, E2, the non-structural polypeptide NS2, NS3, NS4 (NS4a and/or NS4b), NS5 (NS5a and/or NS5b) or any combination thereof (e.g. NS3 and NS4, NS3 and NS4 and NS5b) Antigen(s) of the HIV-1 virus, especially gp120 and gp160 (as described WO 87/06260). Antigen(s) derived from the Human Papilloma Virus (HPV) considered to be associated with genital warts (HPV 6 or HPV 11 and others), and cervical cancer (HPV16, HPV18, HPV 31, HPV-33 and others). Contemplated HPV antigens are selected among the group consisting of E5, E6, E7, L1, and L2 either individually or in combination (see for example WO 94/00152, WO 94/20137, WO 93/02184, WO 90/10459, and WO 92/16636). Contemplated in the context of the disclosure are membrane anchored forms of non-oncogenic variants of the early HPV-16 E6 and/or E7 antigens (as described in WO 99/03885) that are particularly suitable to achieve an antitumoral effect against an HPV-associated cancer. Antigens from parasites that cause malaria. For example, typical antigens from Plasmodia falciparum include RTS (WO 93/10152), and TRAP (WO 90/01496). Other plasmodia antigens that are likely candidates are *P. falciparum*. MSP1, AMA1, MSP3, EBA, GLURP, RAPT, RAP2, Sequestrin, PfEMP1, Pf332, LSA1, LSA3, STARP, SALSA, PfEXP1, Pfs25, Pfs28, PFS27125, Pfs16, Pfs48/45, Pfs230 and their analogues in other *Plasmodium* species.

Other suitable antigens include tumour-associated antigens such as those associated with prostate, breast, colorectal, lung, pancreatic, renal, liver, bladder, sarcoma or melanoma cancers. Exemplary antigens include MAGE 1, 3 and MAGE 4 or other MAGE antigens (WO 99/40188), PRAME, BAGE, Lage (also known as NY Eos 1) SAGE and HAGE (WO 99/53061) or GAGE (Robbins and Kawakami, 1996. Current Opinions in Immunol. 8, pps 628-636). Other suitable tumor-associated antigens include those known as prostase, including Prostate specific antigen (PSA), PAP, PSCA, PSMA. Prostase nucleotide sequence and deduced polypeptide sequence and homologs are disclosed in Ferguson, et al. (1999, Proc. Natl. Acad. Sci. USA. 96, 3114-3119) and WO 98/12302 WO 98/20117 and WO 00/04149. Other suitable tumour-associated antigens include those associated with breast cancer, such as BRCA-1, BRCA-2 and MUC-1 (see for example WO 92/07000).

The transgene in use in the present disclosure is placed under the control of appropriate regulatory elements to permit its expression in the selected host cell or organism in either a constitutive or inducible fashion. The choice of such regulatory elements is within the reach of the skilled artisan. It is typically selected from the group consisting of constitutive, inducible, tumor-specific and tissue-specific promoters as described above in connection with the expression of the fusion protein of the present disclosure. In one example, the transgene is placed under control of the CMV promoter to ensure high level expression.

The transgene in use in the present disclosure can be inserted in any location of the vector. According to one alternative, it is placed typically not in close proximity of the nucleic acid molecule of the disclosure. According to another alternative it can be placed in antisense orientation with respect to the nucleic acid molecule, in order to avoid transcriptional interference between the two expression cassettes. For example, in an adenoviral genome, the transgene can be inserted in a different deleted region with respect to the nucleic acid molecule of the disclosure (E1, E3 and/or E4) or in the same deleted region as said nucleic acid molecule but in antisense orientation to one another.

Introducing the nucleic acid molecule of the disclosure into a vector backbone can proceed by any genetic engineering strategy appropriate in the art for any kind of vectors such as by methods described in Sambrook et al. (2001, Molecular Cloning—A Laboratory Manual, Cold Spring Harbor Laboratory). Typically, for the introduction of the nucleic acid molecule into an adenoviral vector, a bacterial plasmid comprising the fusion-encoding nucleic acid molecule is engineered to replace an adenoviral gene required for replication or assembly (e.g. E1) with the substitute nucleic acid molecule. The plasmid is then used as a shuttle vector, and combined with a second plasmid containing the complementary portion of the adenovirus genome, permitting homologous recombination to occur by virtue of overlapping adenovirus sequences in the two plasmids. The recombination can be done directly in a suitable mammalian host (such as 293 as described in Graham and Prevect, 1991, Methods in Molecular Biology, Vol 7 "Gene Transfer and Expression Protocols"; Ed E. J. Murray, The Human Press Inc, Clinton, N.J.), or else in yeast YAC clones or *E. coli* (as described in WO 96/17070). The completed adenovirus genome is subsequently transfected into mammalian host cells for replication and viral encapsidation.

The present disclosure also encompasses vectors of the disclosure or particles thereof that have been modified to allow preferential targeting of a particular target cell. A characteristic feature of targeted vectors/particles of the disclosure (of both viral and non-viral origins, such as polymer- and lipid-complexed vectors) is the presence at their surface of a targeting moiety capable of recognizing and binding to a cellular and surface-exposed component. Such targeting moieties include without limitation chemical conjugates, lipids, glycolipids, hormones, sugars, polymers (e.g. PEG, polylysine, PEI and the like), peptides, polypeptides (for example JTS1 as described in WO 94/40958), oligonucleotides, vitamins, antigens, lectins, antibodies and fragments thereof. They are typically capable of recognizing and binding to cell-specific markers, tissue-specific markers, cellular receptors, viral antigens, antigenic epitopes or tumor-associated markers. In this regard, cell targeting of adenoviruses can be carried out by genetic modification of the viral gene encoding the capsid polypeptide present on the surface of the virus (e.g. fiber, penton and/or pIX). Examples of such modifications are described in literature (for example in Wickam et al., 1997, J. Viral. 71, 8221-8229; Amberg et al., 1997, Virol. 227, 239-244; Michael et al., 1995, Gene Therapy 2, 660-668; WO 94/10323, EP 02 360204 and WO 02/96939). To illustrate, inserting a sequence coding for EGF within the sequence encoding the adenoviral fiber will allow to target EGF receptor expressing cells. The modification of poxyiral tropism can also be achieved as described in EP 1 146 125. Other methods for cell specific targeting can be achieved by the chemical conjugation of targeting moieties at the surface of a viral particle.

In certain embodiments, the present disclosure relates to infectious viral particles comprising the above-described nucleic acid molecules or vectors of the present disclosure.

The disclosure also relates to a process for producing an infectious viral particle, comprising the steps of: (a) introducing the viral vector of the disclosure into a suitable cell line, (b) culturing said cell line under suitable conditions so as to allow the production of said infectious viral particle, and (c) recovering the produced infectious viral particle from the culture of said cell line, and (d) optionally purifying said recovered infectious viral particle.

The vector containing the nucleic acid molecule of the disclosure can be introduced into an appropriate cell line for propagation or expression using well-known techniques readily available to the person of ordinary skill in the art. These include, but are not limited to, microinjection of minute amounts of DNA into the nucleus of a cell (Capechi et al., 1980, Cell 22, 479-488), $CaPO_4$-mediated transfection (Chen and Okayama, 1987, Mol. Cell. Biol. 7, 2745-2752), DEAE-dextran-mediated transfection, electroporation (Chu et al., 1987, Nucleic Acid Res. 15, 1311-1326), lipofection/liposome fusion (Feigner et al., 1987, Proc. Natl. Acad. Sci. USA 84, 7413-7417), particle bombardment (Yang et al., 1990, Proc. Natl. Acad. Sci. USA 87, 9568-9572), gene guns, transduction, infection (e.g. with an infective viral particle), and other techniques such as those found in Sambrook, et al. (Molecular Cloning: A Laboratory Manual, Cold Spring Harbor Laboratory, Cold Spring Harbor Laboratory Press, Cold Spring Harbor, N.Y., 2001).

When the vector of the disclosure is defective, the infectious particles are usually produced in a complementation cell line or via the use of a helper virus, which supplies in trans the non-functional viral genes. For example, suitable cell lines for complementing adenoviral vectors include the 293 cells (Graham et al., 1997, J. Gen. Virol. 36, 59-72) as well as the PER-C6 cells (Fallaux et al., 1998, Human Gene Ther. 9, 1909-1917) commonly used to complement the E1 function. Other cell lines have been engineered to complement doubly defective adenoviral vectors (Yeh et al., 1996, J. Virol. 70, 559-565; Krougliak and Graham, 1995, Human Gene Ther. 6, 1575-1586; Wang et al., 1995, Gene Ther. 2, 775-783; Lusky et al., 1998, J. Virol. 72, 2022-2033; WO94/28152 and WO97/04119). The infectious viral particles may be recovered from the culture supernatant but also from the cells after lysis and optionally are further purified according to standard techniques (chromatography, ultracentrifugation in a cesium chloride gradient as described for example in WO 96/27677, WO 98/00524, WO 98/22588, WO 98/26048, WO 00/40702, EP 1016700 and WO 00/50573).

The disclosure also relates to host cells which comprise the nucleic acid molecules, vectors or infectious viral particles of the disclosure described herein. For the purpose of the disclosure, the term "host cell" should be understood broadly without any limitation concerning particular organization in tissue, organ, or isolated cells. Such cells may be of a unique type of cells or a group of different types of cells and encompass cultured cell lines, primary cells and proliferative cells.

Host cells therefore include prokaryotic cells, lower eukaryotic cells such as yeast, and other eukaryotic cells such as insect cells, plant and higher eukaryotic cells, such as vertebrate cells and, with a special preference, mammalian (e.g. human or non-human) cells. Suitable mammalian cells include but are not limited to hematopoietic cells (totipotent, stem cells, leukocytes, lymphocytes, monocytes, macrophages, APC, dendritic cells, non-human cells and the like), pulmonary cells, tracheal cells, hepatic cells, epithelial cells, endothelial cells, muscle cells (e.g. skeletal muscle, cardiac muscle or smooth muscle) or fibroblasts. Typical host cells include *Escherichia coli, Bacillus, Listeria, Saccharomyces*, BHK (baby hamster kidney) cells, MDCK cells (Madin-Darby canine kidney cell line), CRFK cells (Crandell feline kidney cell line), CV-1 cells (African monkey kidney cell line), COS (e.g., COS-7) cells, chinese hamster ovary (CHO) cells, mouse NIH/3T3 cells, HeLa cells and Vero cells. Host cells also encompass complementing cells capable of complementing at least one defective function of a replication-defective vector of the disclosure (e.g. adenoviral vector) such as those cited above.

The host cell of the disclosure can contain more than one nucleic acid molecule, vector or infectious viral particle of the disclosure. Further it can additionally comprise a vector encoding a transgene, e.g. a transgene as described above. When more than one nucleic acid molecule, vector or infectious viral particle is introduced into a cell, the nucleic acid molecules, vectors or infectious viral particles can be introduced independently or co-introduced.

Moreover, according to a specific embodiment, the host cell of the disclosure can be further encapsulated. Cell encapsulation technology has been previously described (Tresco et al., 1992, ASAJO J. 38, 17-23; Aebischer et al., 1996, Human Gene Ther. 7, 851-860). According to said specific embodiment, transfected or infected eukaryotic host cells are encapsulated with compounds which form a microporous membrane and said encapsulated cells can further be implanted in vivo. Capsules containing the cells of interest may be prepared employing hollow microporous membranes (e.g. Akzo Nobel Faser A G, Wuppertal, Germany; Deglon et al. 1996, Human Gene Ther. 7, 2135-2146) having a molecular weight cutoff appropriate to permit the free passage of proteins and nutrients between the capsule interior and exterior, while preventing the contact of transplanted cells with host cells.

Still a further aspect of the present disclosure is a method for recombinantly producing the fusion protein, employing the vectors, infectious viral particles and/or host cells of the disclosure. The method for producing the fusion protein comprises introducing a vector or an infectious viral particle of the disclosure into a suitable host cell to produce a transfected or infected host cell, culturing in-vitro said transfected or infected host cell under conditions suitable for growth of the host cell, and thereafter recovering said fusion protein from said culture, and optionally, purifying said recovered fusion protein. It is expected that those skilled in the art are knowledgeable in the numerous expression systems available for expression of the fusion proteins of the disclosure in appropriate host cells.

The host cell of the disclosure is typically produced by transfecting/infecting a host cell with one or more recombinant molecules, (e.g. a vector of the disclosure) comprising one or more nucleic acid molecules of the present disclosure. Recombinant DNA technologies can be used to improve expression of the nucleic acid molecule in the host cell by manipulating, for example, the number of copies of the nucleic acid molecule within a host cell, the efficiency with which the nucleic acid molecule is transcribed, the efficiency with which the resultant transcripts are translated, the efficiency of post-translational modifications and the use of appropriate selection. Recombinant techniques useful for increasing the expression of nucleic acid molecules of the present disclosure include, but are not limited to, the use of high-copy number vectors, addition of vector stability sequences, substitution or modification of one or more transcriptional regulatory sequences (e.g., promoters, operators, enhancers), substitution or modification of translational regulatory sequences (e.g., ribosome binding sites, Shine-Dalgarno sequences), modification of nucleic acid molecule of the present disclosure to correspond to the codon usage of the host cell, and deletion of sequences that destabilize transcripts.

Host cells of the present disclosure can be cultured in conventional fermentation bioreactors, flasks, and petri plates. Culturing can be carried out at a temperature, pH and oxygen content appropriate for a given host cell. No attempts to describe in detail the various methods known for the expression of proteins in prokaryote and eukaryote cells will be made here. In one embodiment, the vector is a plasmid carrying the fusion-encoding nucleic acid molecule in operative association with appropriate regulatory elements. Typical host cells in use in the method of the disclosure are mammalian cell lines, yeast cells and bacterial cells.

Where the fusion protein is not secreted outside the producing cell or where it is not secreted completely, it can be recovered from the cell by standard disruption procedures, including freeze thaw, sonication, mechanical disruption, use of lysing agents and the like. If secreted, it can be recovered directly from the culture medium. The fusion protein can then be recovered and purified by well-known purification methods including ammonium sulfate precipitation, acid extraction, gel electrophoresis, reverse phase chromatography, size exclusion chromatography, ion exchange chromatography, affinity chromatography, phosphocellulose chromatography, hydrophobic-interaction chromatography, hydroxylapatite chromatography, lectin chromatography, or high performance liquid chromatography. The conditions and technology used to purify a particular fusion protein of the disclosure will depend on the synthesis method and on factors such as net charge, molecular weight, hydrophobicity, hydrophilicity and will be apparent to those having skill in the art. It is also understood that depending upon the host cell used for the recombinant production of the fusion proteins described herein, the fusion proteins can have various glycosylation patterns, or may be non-glycosylated (e.g. when produced in bacteria). In addition, the fusion protein may include an initial methionine in some cases as a result of a host-mediated process.

The fusion protein of the disclosure can be "purified" to the extent that it is substantially free of cellular material. The level of purification will be based on the intended use. The critical feature is that the preparation allows for the desired function of the fusion protein, even if in the presence of considerable amounts of other components. In some uses, "substantially free of cellular material" includes preparations of the fusion protein having less than about 30% (by dry weight) other proteins (i.e., contaminating proteins), typically less than about 20% other proteins, more typically less than about 10% other proteins, or even more typically less than about 5% other proteins. When the fusion protein is recombinantly produced, it can also be substantially free of culture medium, i.e., culture medium represents less than about 20% of the volume of the protein preparation.

Terms

As used herein, the term "conjugate" refers to molecular entities joined by covalent bonds or other arrangement that provides substantially irreversible binding under physiological conditions. For example, two proteins may be conjugated together by a linker polymer, e.g., polypeptide sequence, ethylene glycol polymer. Two proteins may be conjugated together by linking one protein to a ligand and linking the second protein to a receptor, e.g., streptavidin and biotin or an antibody and an epitope.

As used herein, the term "combination with" when used to describe administration with an additional treatment means that the agent may be administered prior to, together with, or after the additional treatment, or a combination thereof.

As used herein, "subject" refers to any animal, typically a human patient, livestock, or domestic pet.

As used herein, the terms "prevent" and "preventing" include the prevention of the recurrence, spread or onset. It is not intended that the present disclosure be limited to complete prevention. In some embodiments, the onset is delayed, or the severity is reduced.

As used herein, the terms "treat" and "treating" are not limited to the case where the subject (e.g. patient) is cured and the disease is eradicated. Rather, embodiments of the present disclosure also contemplate treatment that merely reduces symptoms, and/or delays disease progression.

As used herein, "amino acid sequence" refers to an amino acid sequence of a protein molecule. An "amino acid sequence" can be deduced from the nucleic acid sequence encoding the protein. However, terms such as "polypeptide" or "protein" are not meant to limit the amino acid sequence to the deduced amino acid sequence, but include non-naturally occurring amino acids, post-translational modifications of the deduced amino acid sequences, such as amino acid deletions, additions, and modifications such as glycolsylations and addition of lipid moieties.

The term "a nucleic acid sequence encoding" a specified polypeptide refers to a nucleic acid sequence comprising the coding region of a gene or in other words the nucleic acid sequence which encodes a gene product. The coding region may be present in a cDNA, genomic DNA or RNA form. When present in a DNA form, the oligonucleotide, polynucleotide, or nucleic acid may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present disclosure may contain endogenous enhancers/promoters, splice junctions, intervening sequences, polyadenylation signals, etc. or a combination of both endogenous and exogenous control elements.

The term "recombinant" when made in reference to a nucleic acid molecule refers to a nucleic acid molecule which is comprised of segments of nucleic acid joined together by means of molecular biological techniques. The term "recombinant" when made in reference to a protein or a polypeptide refers to a protein molecule which is expressed using a recombinant nucleic acid molecule.

A "virus-like particle" refers to a particle comprising virion proteins but is substantially free of viral genetic material, e.g., viral RNA. Virus-like particles may contain viral proteins from different viruses. See e.g., Guo et al., Enhancement of mucosal immune responses by chimeric influenza HA/SHIV virus-like particles, Virology, 2003, 313(2):502-13. Virus-like particles may contain lipid membranes and may be constructed to express a variety of antigens on their particle surface ether by expression in viral vectors use to create the particles or by mixing the virus-like particle with an antigen or other polypeptide conjugated to a glycosylphosphatidyl-inositol anchor. See e.g. Skountzou et al., J. Virol. 81(3):1083-94; Derdak et al., PNAS, 2006, 103(35) 13144-13149; Poloso et al., Molecular Immunology, 2001, 38:803-816.

As used herein, the article "a" or "an" is intended to refer to one or more unless the context suggests otherwise.

EXPERIMENTAL

Animals and Reagents

Wild-type female C57/BL6 (B6) mice, C57BL/6-Tg (TcraTcrb)1100Mjb/J (OT-I), C57BL/6-Tg(TcraTcrb) 425Cbn/J (OT-II) used experimentally were between the age of 6-8 weeks, purchased from The Jackson Laboratory (Bar Harbor Me.). Recombinant rIL-7, rGM-CSF, and their antibodies were purchased from R&D systems (Minneapolis Minn.). Dulbecco's Modified Eagle's Medium (DMEM), RPMI-1640, fetal bovine serum and Penicillin/Streptomycin were purchased from Wisent Technologies (Rocklin, Calif.). Cell separations were performed using EasySep kits according to the manufacturer's instruction (StemCell Technologies, Vancouver BC Canada).

Fusokine Generation and Protein Modeling

The fusokine is composed of 2 entities. GM-CSF was amplified by PCR in order to generate and subsequently cloned in frame at the N-terminus with the cDNA encoding IL-7 into the expression vector pORF. As such, the chimeric transgene was expressed as a single open reading frame. HEK293 cells were seeded at 65-80% confluency and transiently transfected using Polyfect (Qiagen, Mississauga, ON, Canada) and supernatant was tested by western-blot. Three days later, the supernatant was collected, concentrated using AMICONS (Millipore (Cambridge, Ontario, Canada) and tested by western-blot. GIFT7 expression levels were subsequently assessed using anti-IL-7 and anti-GM-CSF ELISA kit.

Human GIFT7 was constructed from the following nucleic acid sequence (SEQ ID NO: 3)

ATGTGGCTGCAGAGCCTGCTGCTCTTGGGCACTGTGGCCTGCAGCA

TCTCTGCACCCGCCCGCTCGCCCAGCCCCAGCACGCAGCCCTGGGA

GCATGTGAATGCCATCCAGGAGGCCCGGCGTCTCCTGAACCTGAGT

AGAGACACTGCTGCTGAGATGAATGAAACAGTAGAAGTCATCTCAG

AAATGTTTGACCTCCAGGAGCCGACCTGCCTACAGACCCGCCTGGA

GCTGTACAAGCAGGGCCTGCGGGGCAGCCTCACCAAGCTCAAGGGC

CCCTTGACCATGATGGCCAGCCACTACAAGCAGCACTGCCCTCCAA

CCCCGGAAACTTCCTGTGCAACCCAGATTATCACCTTTGAAAGTTT

CAAAGAGAACCTGAAGGACTTTCTGCTTGTCATCCCCTTTGACTGC

TGGGAGCCAGTCCAGGAGTCACCGGTCAACATGTTCCATGTTTCTT

TTAGGTATATCTTTGGACTTCCTCCCCTGATCCTTGTTCTGTTGCC

AGTAGCATCATCTGATTGTGATATTGAAGGTAAAGATGGCAAACAA

TATGAGAGTGTTCTAATGGTCAGCATCGATCAATTATTGGACAGCA

TGAAAGAAATTGGTAGCAATTGCCTGAATAATGAATTTAACTTTTT

TAAAAGACATATCTGTGATGCTAATAAGGAAGGTATGTTTTTATTC

CGTGCTGCTCGCAAGTTGAGGCAATTTCTTAAAATGAATAGCACTG

GTGATTTTGATCTCCACTTATTAAAAGTTTCAGAAGGCACAACAAT

ACTGTTGAACTGCACTGGCCAGGTTAAAGGAAGAAAACCAGCTGCC

CTGGGTGAAGCCCAACCAACAAAGAGTTTGGAAGAAAATAAATCTT

TAAAGGAACAGAAAAAACTGAATGACTTGTGTTTCCTAAAGAGACT

ATTACAAGAGATAAAAACTTGTTGGAATAAAATTTTGATGGGCACT

AAAGAACACTGA.

-continued

Murine GIFT7 was constructed from the following nucleic acid sequence (SEQ ID NO: 4)
ATGTGGCTGCAGAATTTACTTTTCCTGGGCATTGTGGTCTACAGCC

TCTCAGCACCCACCCGCTCACCCATCACTGTCACCCGGCCTTGGAA

GCATGTAGAGGCCATCAAAGAAGCCCTGAACCTCCTGGATGACATG

CCTGTCACGTTGAATGAAGAGGTAGAAGTCGTCTCTAACGAGTTCT

CCTTCAAGAAGCTAACATGTGTGCAGACCCGCCTGAAGATATTCGA

GCAGGGTCTACGGGGCAATTTCACCAAACTCAAGGGCGCCTTGAAC

ATGACAGCCAGCTACTACCAGACATACTGCCCCCCAACTCCGGAAA

CGGACTGTGAAACACAAGTTACCACCTATGCGGATTTCATAGACAG

CCTTAAAACCTTTCTGACTTCACCGGTAGGAGGGGCCAACATGTTC

CATGTTTCTTTTAGATATATCTTTGGAATTCCTCCACTGATCCTTG

TTCTGCTGCCTGTCACATCATCTGAGTGCCACATTAAAGACAAAGA

AGGTAAAGCATATGAGAGTGTACTGATGATCAGCATCGATGAATTG

GACAAAATGACAGGAACTGATAGTAATTGCCCGAATAATGAACCAA

ACTTTTTTAGAAAACATGTATGTGATGATACAAAGGAAGCTGCTTT

TCTAAATCGTGCTGCTCGCAAGTTGAAGCAATTTCTTAAAATGAAT

ATCAGTGAAGAATTCAATGTCCACTTACTAACAGTATCACAAGGCA

CACAAACACTGGTGAACTGCACAAGTAAGGAAGAAAAAAACGTAAA

GGAACAGAAAAAGAATGATGCATGTTTCCTAAAGAGACTACTGAGA

GAAATAAAAACTTGTTGGAATAAAATTTTGAAGGGCAGTATATAA.

MSC-GIFT7 Implantation and C1498FFDsR Challenge

Whole bone marrow from femurs and tibias of $CCL2^{-/-}$ C57BL/6 mice was harvested and placed in culture in complete medium until the appearance of a homogeneous MSC polyclonal population. The mGIFT7 cDNA was cloned in the AP2 retroviral plasmid and retroparticles generated. Concentrated retroparticles were then used to gene modify $CCL2^{-/-}$ C57BL/6 MSCs. Secretion and expression levels of GIFT7 by gene enhanced MSCs were analyzed by GMCSF and IL7 ELISA.

Cell Culture

Human embryonic kidney (HEK)293 cell line was cultured in DMEM (Wisent Technologies) supplemented with 10% FBS (Wisent Technologies) and 100 U/ml of Penicillin/Streptomycin (Wisent Technologies). RAW 264.7 cell line was purchased from ATCC and cultured in DMEM with 10% FBS and 100 U/mL of penicillin/streptomycin. Primary mouse splenocytes and human peripheral blood mononuclear cells (hPBMC) were cultured in RPMI supplemented with 2 mM L-glutamine, 1 mM HEPES, 1 mM sodium pyruvate, 0.05 mMβ-mercaptoethanol with 10% FBS. Spleen-derived T cells were cultured in complete splenocyte medium.

Apoptosis Analysis

For apoptosis assays, 106 CD8 T cells cultured for 48-72 hrs with equimolar concentrations of rGM-CSF, rIL-7, rGM-CSF/mL-7, or GIFT7 were analyzed by PI and annexin-V staining to access percent apoptotic cells.

Western Blotting

For the detection of GIFT7, concentrated conditioned media from mock (PolyFect alone) or GMME3-transfected HEK 293 cells were denatured at 90° C. for 5 minutes and separated on 4-20% SDS PAGE gel (Thermo scientific, Pittsburgh, Pa.). Immuno-blotting was performed with anti-IL-7 antibody and anti-GM-CSF antibody according to manufacturer's guideline. For the study of the GMME3 biochemical response, 1-2×106RAW264.7 cells or mouse spleen-derived primary T cells were stimulated with GIFT7, or cytokine controls in RPMI media for 20 minutes. Cell lysates were prepared by using cell lytic M supplemented with protease inhibitor and phosphatase inhibitor according to manufacturer's instruction. Anti-phosphorylated or total STATS antibody (Cell Signaling Technology, Danvers, Mass.) was used in immuno-blotting.

Flow Cytometry and Intracellular Staining

Cells to be analyzed by fluorescence-activated cell sorter (FACS) were harvested and resuspended in $10 \times 10^6$ cells/ml. Samples were blocked with anti-FcRmAb 2.4G2 for 30 minutes and subsequently stained with fluorochrome-conjugated monoclonal antibody in $Ca^{2+}Mg^{2+}$ free phosphate-buffered saline (PBS) with 2% fetal bovine serum for 30 minutes. Cells were washed twice with staining buffer and resuspended in 1% PFA prior to analysis. Intracellular staining was performed with Cytofix/Cytoperm Kit (BD) according to manufacturer's instruction. FACS antibodies were purchased from BD Pharmingen.

In Vitro Antigen Presentation Assay

Peritoneal macrophages were collected from lavage of the C57B/6 RB peritoneal cavity with 12 ml RPMI. Cells were cultured in 24-well plates and washed after 16 hours. Plastic adherent-macrophages were cultured in RPMI supplemented with 1 mg/ml of MOG 35-55 peptide (Sheldon Biotech Center, McGill University) or chicken ovalbumin (Sigma) overnight. $CD4^+$ T cells were purified from the spleens of EAE mice with active disease or OT-II transgenic mice. $CD8^+$ T cells were purified from the spleen of OT-I transgenic mice. 5×105 purified T cells were cultured with antigen-pulsed, 1% paraformaldehyde-fixed macrophages in complete splenocyte medium. Alternatively, peritoneal-macrophages were pre-treated with 105 GMME3-activated B cells (BGMME3) for 48 hours. OTII-$CD4^+$ or OT-1-$CD8^+$ T cells were subsequently added to pre-treated antigen-pulsed macrophages. Culture supernatant was collected after 72 hours and inflammatory cytokine IFN-γ or IL17 were measured by ELISA when appropriate.

Human Ortholog of GIFT7 Leads to Enhanced T Cell Proliferation

Figure 6:
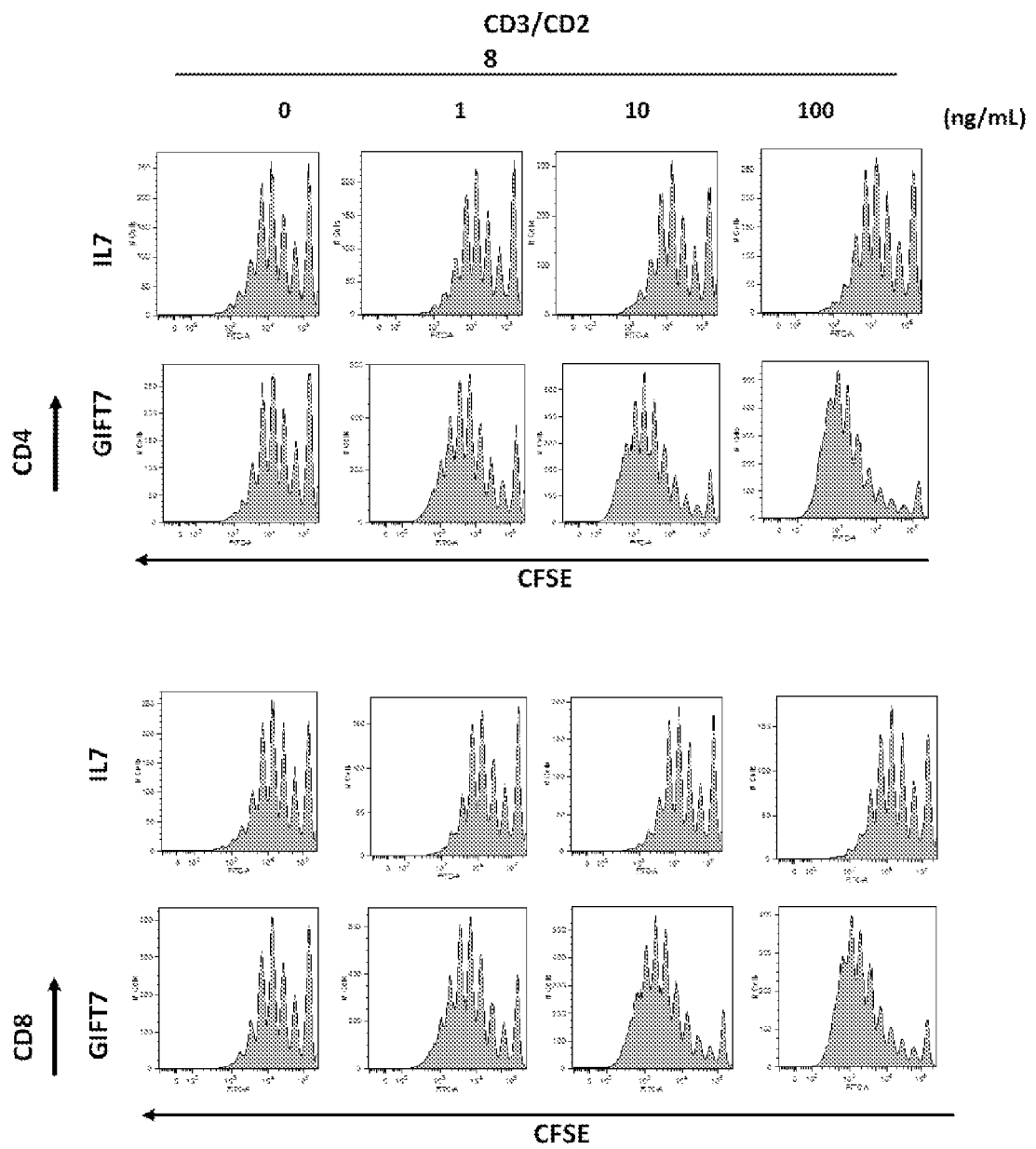
FIG. 6 shows data indicating GIFT7 leads to enhanced T cell proliferation.

Concentrated media conditioned by 293T cells transfected with pORF-hGIFT7 was used to measure the expression and activity of hGIFT7 immuno-blotting of conditioned media derived from hGIFT7-tranfectant probed with α-hGMCSF or α-hIL7 antibody detected a bi-cistronic fusion protein at roughly 60 kDa (FIG. 1). To test the bioactivity of GIFT7, pre-activated human PBMC were cultured with recombinant hIL7 or GIFT7. hGIFT7 induced a superior proliferative response compared to IL7 at a concentration as low as 0.1 ug/mL in both $CD4^+$ and $CD8^+$ T cells. This superior mitogenic effect was enhanced with increasing concentration (FIG. 6). The secreted hGIFT7 properly folded and leads to significant proliferative in T cells derived from PBMC.

Simian PBMC (sPBMC) Treated with hGIFT7 are $Ki67^{hi}$ and $PD1^{Low}$

Figure 7A:
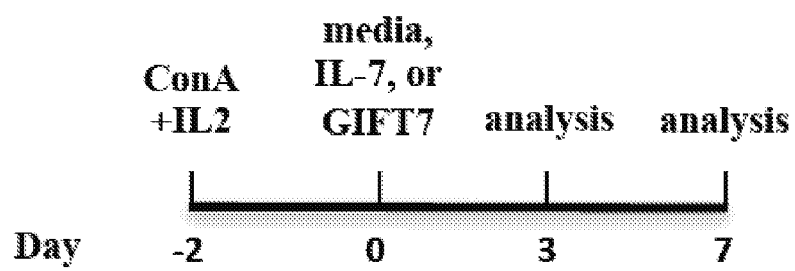
FIG. 7A-C shows data indicating Simian PBMC (sPBMC) treated with hGIFT7 are Ki67$^{hi}$ and PD1$^{low}$.
Figure 7B:
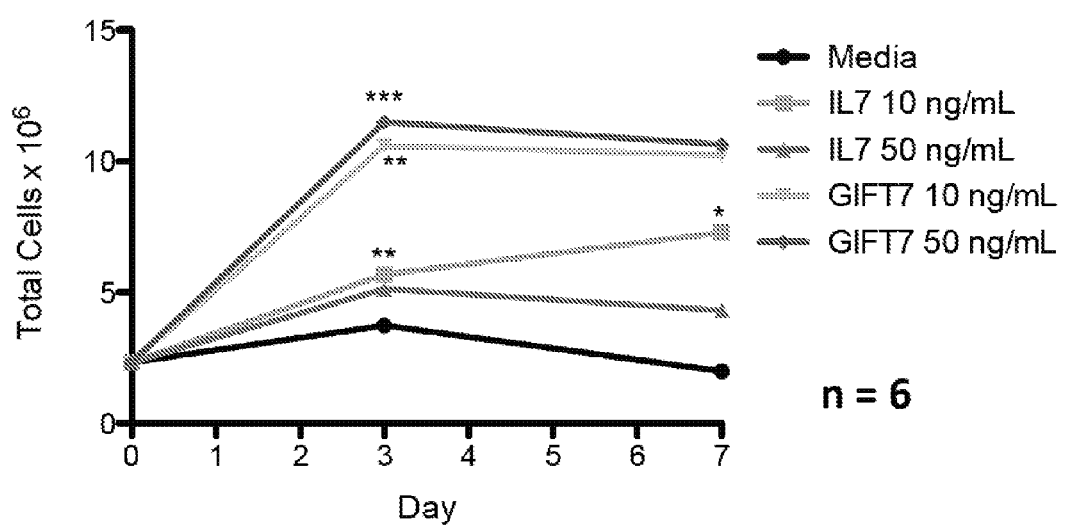
Figure 7C:
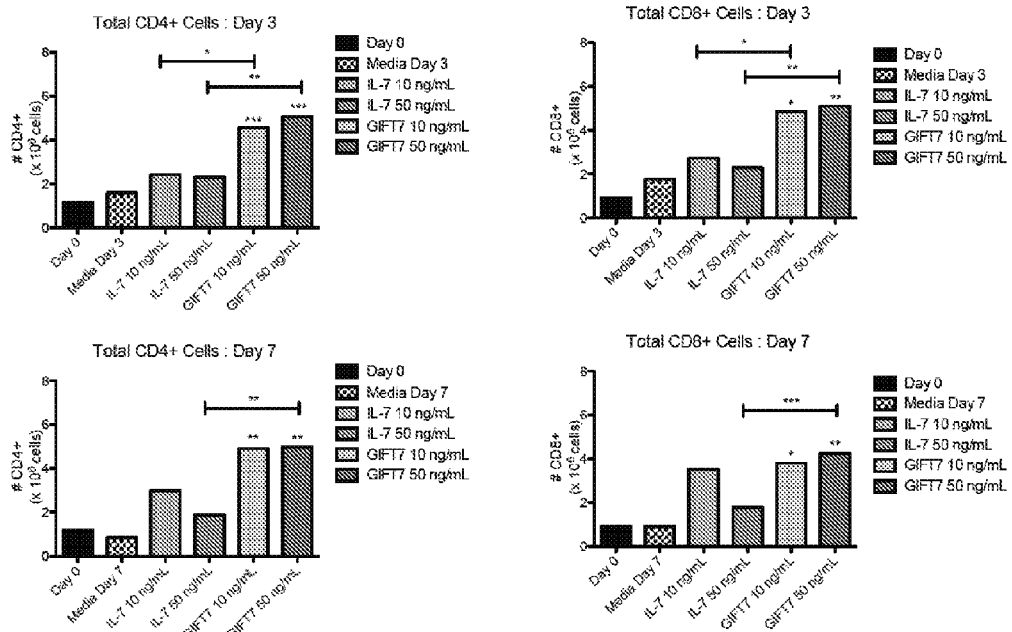
Figure 7D:
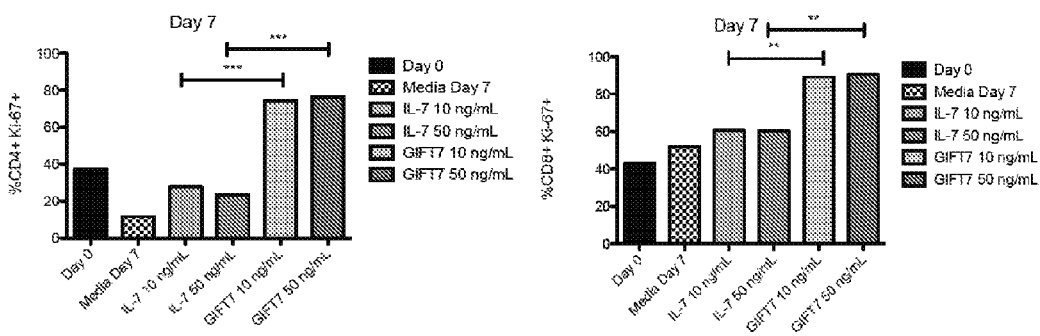
Figure 7E:
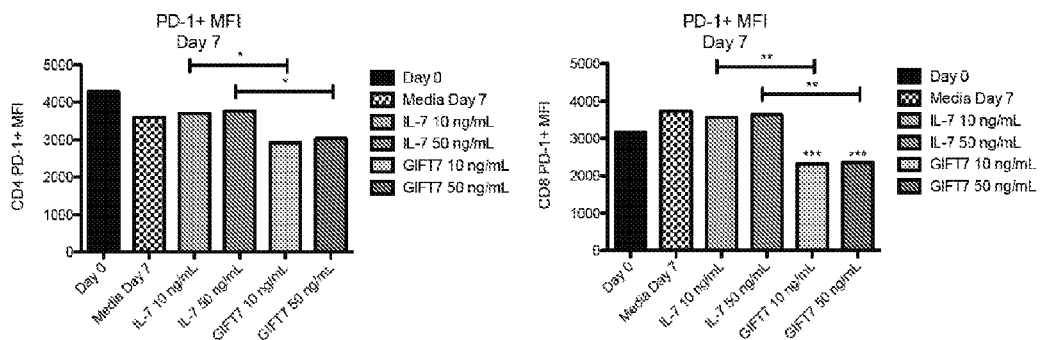

The effect of hGIFT7 on simian T cells was investigated. Pre-activated sPBMC were treated ex vivo with recombinant IL7 or GIFT7 (10 ng $mL^{-1}$ and 50 ng $mL^{-1}$) for 3 or 7 days (FIG. 7A). GIFT7-treated sPBMC (both 10 ng$mL^{-1}$ and 50 ng$mL^{-1}$) showed marked increase in absolute cell number as soon as day 3. On day 7, total cell number has been maintained (FIG. 7B). In both $CD4^+$ and $CD8^+$ T cells, GIFT7 treatment increases total cell number after 3 or 7 days (FIG. 7C). Importantly, on day 7, the frequency of $Ki67^+$ T cells are significantly higher in both CD4$^+$ (~2 fold increase) and CD8$^+$ subset (~50% increase), suggesting GIFT7 has maintained T cells in a proliferative state (FIG. 7C). Interestingly, GIFT7-mediated proliferative T cells have lower overall expression of PD-1, especially in the CD8$^+$ subset (FIG. 7D). Overall the data suggest that the human ortholog of GIFT7 maintains simian T cell expansion and prevents exhaustion during the contraction phase (i.e. post-activation).

GIFT7 Leads to the Generation of Central Memory-Like T Cells Post-Activation

Figure 8A:
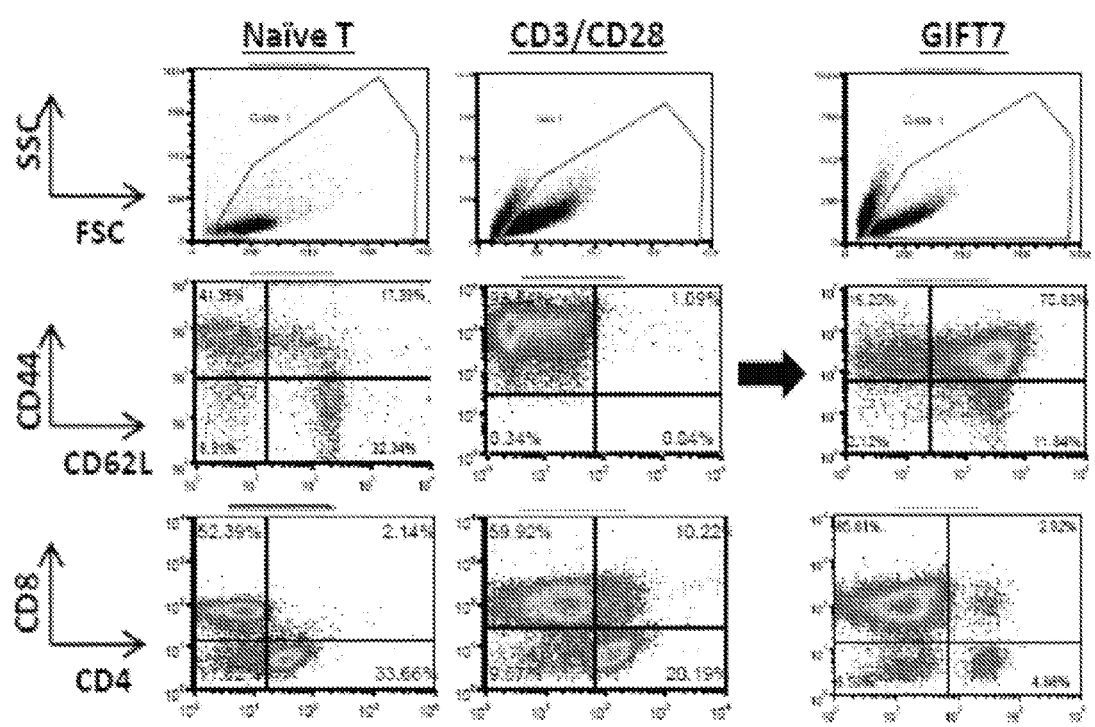
FIGS. 8A-C shows data indicating GIFT7 leads to the generation of central memory-like T cells post-activation.
Figure 8B:
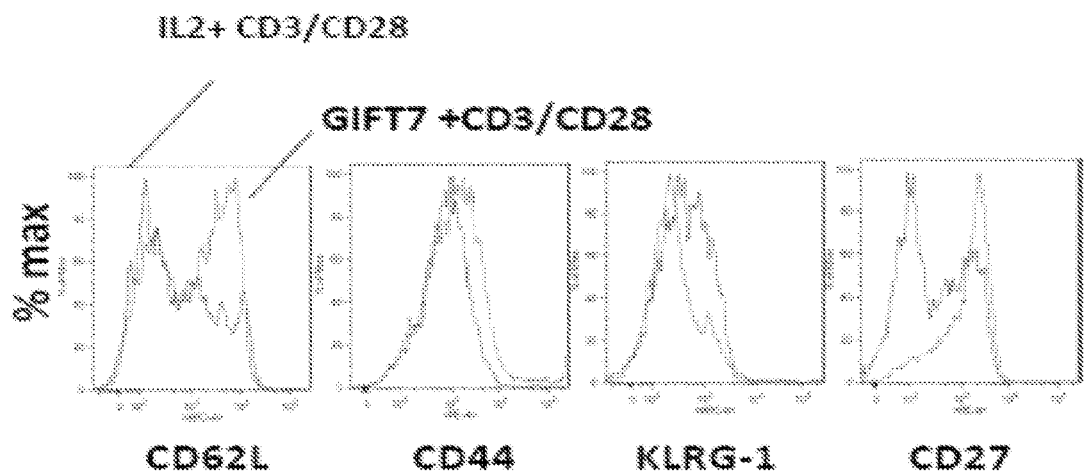
Figure 8C:
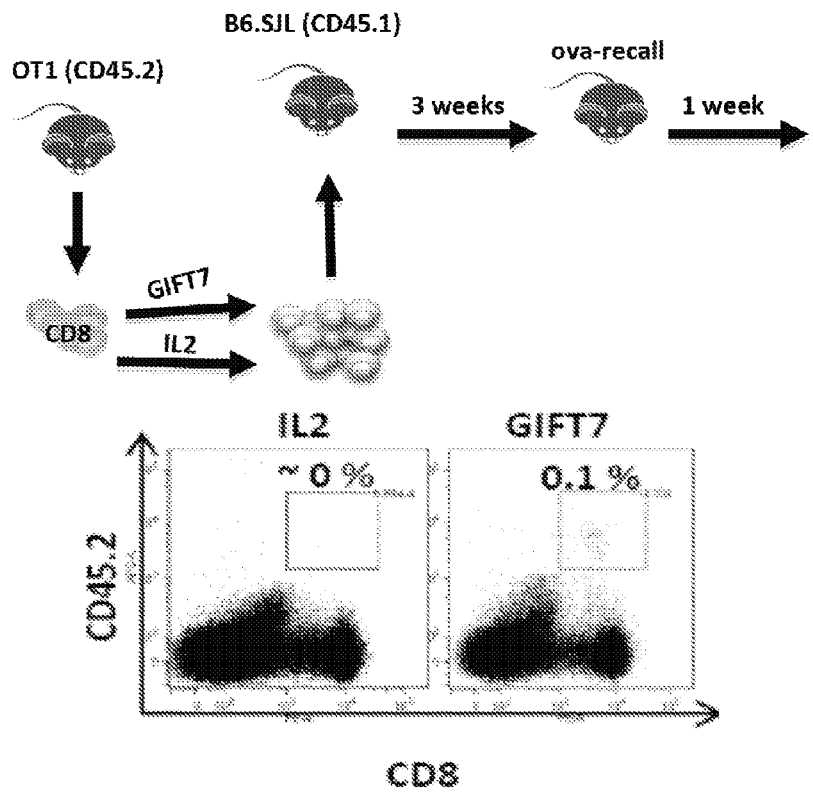

The effect of GIFT7 on T cells post-activation was examine to determine whether GIFT7 leads to the expansion of memory-type T cells. CD3$^+$ purified T cells from WT C57B/L6 spleen were heterogeneous based on CD44 and CD62L expression. αCD3/CD28 antibody-coated beads were used to mimic TCR stimulation. After 3 days, αCD3/CD28 beads were washed off and T cell culture were supplemented with GIFT7 or monomeric cytokine controls. TCR stimulation leads to significant cell activation and proliferation (increase in FSC and SSC) with concurrent up-regulation of CD44 and down-regulation of CD62L. Interestingly, GIFT7 signaling during post-activation maintained T cell population—preferentially enhanced the expansion of CD8$^+$ T cells—and induced the re-expression of CD62L, suggesting $T_{GIFT7}$ acquire homing capacity to secondary lymphoid system (FIG. 8A). To analyze the phenotype between $T_{GIFT7}$ and conventionally activated T cells (αCD3/CD28 in the presence of IL2), the expression of a number of T cell differentiation markers were examined. CD8$^+$ $T_{GIFT7}$ were found to be CD62L$^{hi}$CD44$^{hi}$KLRG-1$^{low}$/CD27$^{hi}$; in particular, there was a marked upregulation of CD62L and CD27 on $T_{GIFT7}$ compared to conventionally activated T cells (FIG. 8B). One of the hallmarks of memory-type T cells is their ability to persist in vivo. To determine whether ex vivo generated $T_{GIFT7}$ persist in vivo after reinfusion and expand upon recall challenge, CD8$^+$ T cells were purified from OVA-specific OTI mice (CD45.2) and stimulated with αCD3/CD28 in the presence of GIFT7 or IL2. OTI $T_{GIFT7}$ or $T_{IL2}$ were re-infused back to B6.SJL (CD45.1) mice. 3 weeks later ovalbumin was administered. After a week, splenocytes were analyzed for the co-expression of CD45.2 and CD8 to elucidate the persistence of the adoptive transferred T cells. There was a 10-fold increase in the survival of $T_{GIFT7}$ compared to $T_{IL2}$ after a recall challenge (FIG. 8C). GIFT7 signaling on T cells during the contraction phase not only rescues T cell pool but also expand a population of CD8$^+$ subset that exhibit a phenotype with better in vivo fitness.

GIFT7-Mediated Anti-Tumor Effect In Vivo

Figure 9A:
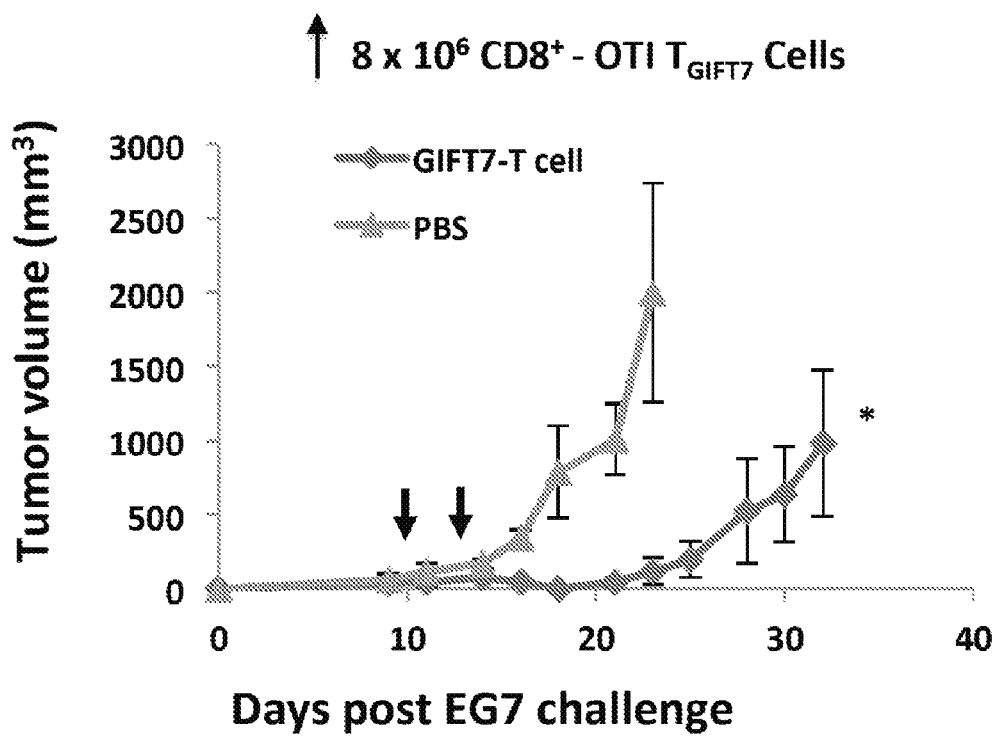
FIGS. 9A-B shows data indicating a GIFT7-mediated anti-tumor effect in vivo.
Figure 9B:
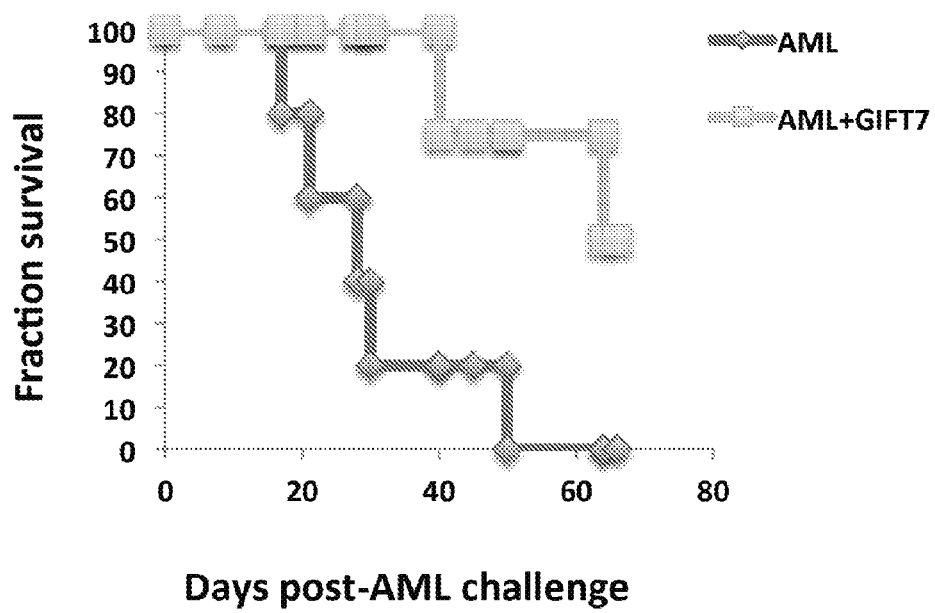

CD8$^+$ T cells were purified from OT1-trangenic mice and expanded in the presence of GIFT7. The ex vivo expanded $T_{GIFT7}$ cells were subsequently re-infused back to OVA-expressing EG7-bearing mice. Two doses of 8×10$^6$ $T_{GIFT7}$ adoptive transfer significantly delayed tumor progression (FIG. 9A). Acute myelogenous leukemia C1498 cells cause CD8$^+$ immune effector failure via PD-1 up-regulation. Disease mortality is related to hepatocellular metastasis and subsequent immune dysfunction. See Zhang et al., Blood., 2009, 114(8):1545-1552. In order to test if the in vivo administration of GIFT7 can overcome AML-induced T cell exhaustion thereby decreasing tumor burden and improving overall survival, gene-enhanced autologous mesenchymal stromal cells (MSC) were implanted subcutaneously to act as protein delivery vehicle. It is a neo-organoid system that we have demonstrated to have led to sustained protein production detectable systemically. See Eliopoulos et al., Cancer Res., 2008, 68(12):4810-4818. As such, mice challenged with 10$^6$ C1498 were co-transplanted with contigen-embedded MSC-GIFT7 or MSC-null (1.5×10$^6$ cells/contigen). Overall, GIFT7 administration significantly improved survival with 50% of mice surviving a lethal dose of C1498 challenge (FIG. 9B).

GIFT7 Acts as an IL7 Hyperagonist

To predict the possible binding mode of GIFT7 with IL7Rα, we in silico aligned the IL7 portion of GIFT7 with the crystal structure of IL7 in complex with IL7Rα. The GMCSF portion of GIFT7 is not in steric clash with IL7Rα. N-terminal GMCSF may contribute to the binding of GIFT7 with IL7Rα. Immunoblotting demonstrates that GIFT7 is translated, secreted, and recognized by both α-GMCSF and α-IL7 antibodies (FIG. 1B). GIFT7 stimulation leads to hyperphosphorylation of STAT5 downstream of IL7Rα (primary T cells) but not GMCSFR (RAW 264.7) compared to the combination of its parental monomeric cytokines (FIG. 2). To determine the impact of GIFT7-mediated hyperSTAT5 signalling, the surviving and proliferating fraction of GIFT7-treated splenic T cells prestimulated in vitro with α-CD3/CD28-coated beads for 3 days were measured. TCR stimulation withdrawal induced apoptosis in all control cytokine-treated T cells whereas GIFT7 treatment led to significantly increased surviving fraction (FIG. 2). GIFT7-treated T cells resist contraction-induced apoptosis, but also undergo substantial mitotic expansion.

GIFT7 Leads to DN Expansion In Vitro

Thymocytes were isolated from 6-8 week old mice and cultured in the presence or absence of GIFT7 (10 ngmL$^{-1}$). Consistent with reported literature, dissociated thymus consist of approximately 4.5% DN, 4.2% SPCD8, 8% SPCD4, and 83% DP. Compared to control thymocyte cultures, GIFT7-treated thymocytes show significant DN and SPCD8 expansion in the live cell fraction as early as 72 hours after stimulation. At later time point (day 7), the DN and SPCD8 fraction are 32% and 35% respectively in the GIFT7-treated thymocyte culture. 7AAD staining also demonstrated GIFT7 protect DN and SPCD8 but not SPCD4 from apoptosis. This phenomenon cannot be recapitulated by GMCSF, IL7 or the combination of both cytokines at equimolar concentrations. CFSE-pulsed DN cells show significant dilution after GIFT7 treatment in both TCRγδ$^-$ and TCRγδ$^+$ compartments, demonstrating the mitogenic effect of GIFT7 on DN subset in both αβ- and γδ-lineage (FIG. 4, panel C). GIFT7-expanded DN thymocytes increased expression of CD44 and granularity (FSC) but not CD25 or CD24, which corresponds to early thymic DN1 progenitors (FIG. 4, panel B).

To test the hypothesis that GIFT7 modulate early T cell differentiation, DN, SPCD4, SPCD8, and DP thymocytes were pre-sorted and subsequently stimulated them with GIFT7 for 9 days. GIFT7 did not alter the expression of CD4 and CD8 on pre-sorted cells. In all, these data indicate that GIFT7—by provision of its hyperphosphoSTAT5 effect—leads to the survival and expansion of CD4$^-$CD8$^-$CD25$^-$CD24$^-$CD44$^+$ early thymic progenitors and SPCD8 thymocytes in vitro without influencing their differentiation programming.

GIFT7 Leads to Transient Thymic Hyperplasia in Immune-Competent Young Mice

The systemic effect of GIFT7 administration on thymic tissue in normal 6-8 week old adult mice was investigated. Mice treated with GIFT7 or IL7 were analyzed for thymic cellularity on day 7, 14 or 35 post-treatment. On day 7, both IL7 and GIFT7-treated mice showed significant increase in total thymic cellularity, which continues to rise in GIFT7-treated group but starts to decline in the IL7 group by day 14 (237±51.3 v.s. 123±25.6×106, p<0.05) (FIG. 10A). In particular, compared to IL7, GIFT7 increased the percentage as well as the total number of DN1 cells by day 7 (5.48±1.01 v.s.

Figure 10B:
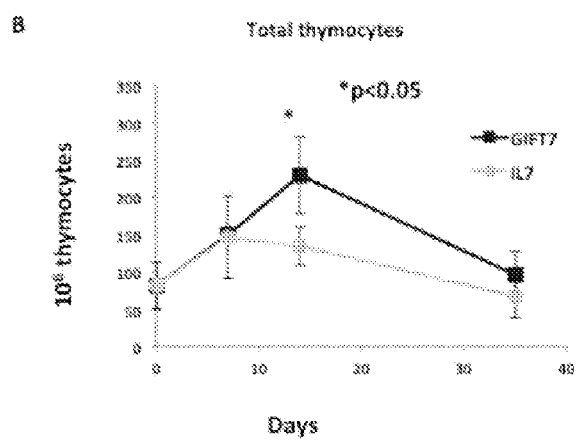

2.74±1.07×106, p<0.05) (FIG. 10B). The ratio of thymic subsets normalized between these two groups by day 14 despite an increase in total thymocytes and the DP compartment (FIG. 10C). On day 35 post-injection, total thymic cellularity in both GIFT7- and IL7-treated groups has declined to a level similar to that of prior to treatment (FIG. 10A). GIFT7 was able to overcome immune checkpoints, driving transient and reversible thymic hypertrophy. GIFT7 acts on the DN1 subset initially, which in turn contributed to the expansion of DP and total thymocytes at later stage even in an immune-replete state. This transient thymic-specific hypertrophic effect—splenic cellularity remains unchanged—demonstrates the gain of function of GIFT7 in vivo.

GIFT7 Corrects Age-Related Thymic Atrophy and Enhances Thymic Output

Whether GIFT7 can reverse age-associated thymic atrophy was investigated. Aged mice were injected with 7 doses of IL7 or GIFT7 (5 ug/Kg) every other day. On day 28 posttreatment, hematoxylin/eosin (H&E) staining on thymic tissues of IL7-treated aged mice shows extensive adipocyte deposit (*), reduced cortical thymic tissue (cortex: medulla ratio 2:1) with intact cortical medullary thymic lining (interrupted arrow) whereas GIFT7-treated mice exhibit minimal adipocyte deposits (*), hypercellularity in the cortex (cortex: medulla ratio 2.67:1) and disrupted cortical-medullary lining with thymocytes infiltrating the medulla, indicating foci of proliferation (solid arrow) (FIG. 11A). In accordance with the histology data, GIFT7-treated mice have significantly higher number of total thymocytes (111±22, 68±14, 60±4.6×106 p<0.05 for GIFT7-, IL7—treated, and untreated—groups respectively). The expansion is distributed in all four different subsets with DN exhibit the greatest fold difference (FIG. 11B). GIFT7 administration enhances de novo T cell production in the periphery as measured by the mRNA level of single joint TREC per TCRα in total splenic DNA (FIG. 11C). This indicates that GIFT7-mediated thymopoeisis undergo the normal process of T cell development, thus increasing the number of recent thymic emigrants in the periphery.

Figure 12A:
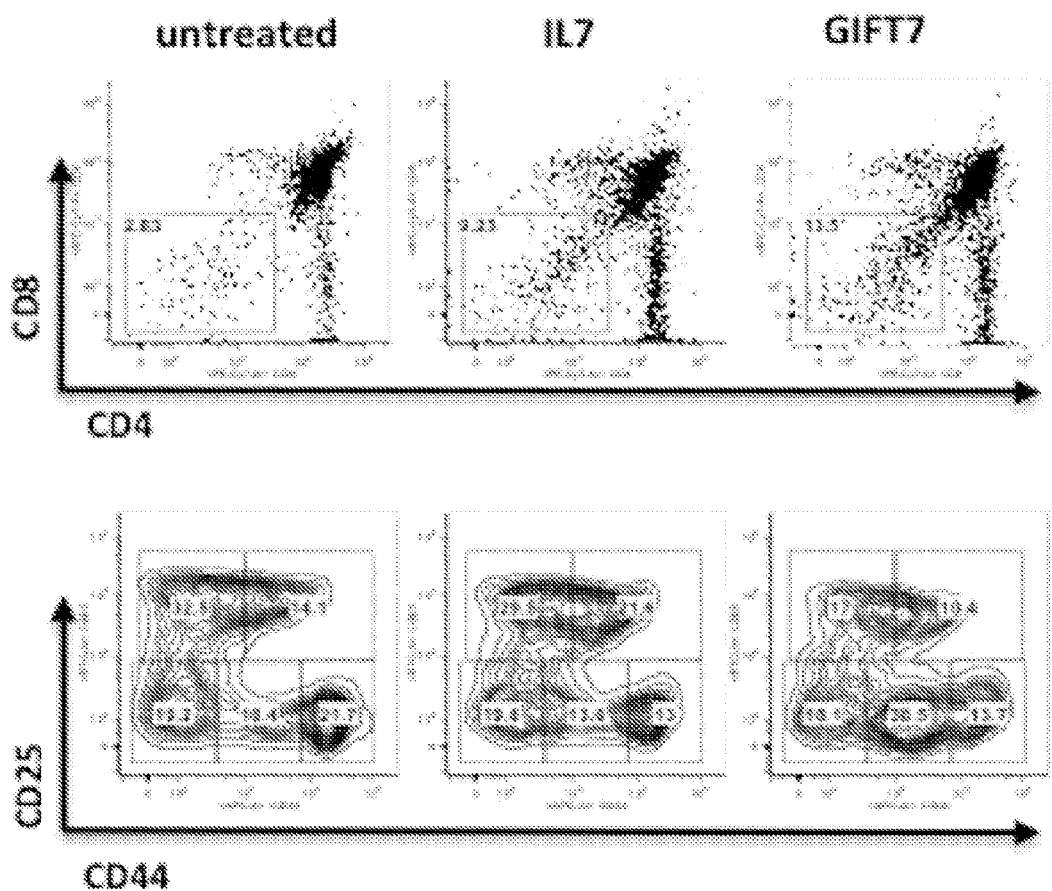
FIGS. 12A-C show data indicating CD44$^{int}$ DN resident thymocytes drives GIFT7—mediated reconstitution (A) Representative flow cytometry plots indicate GIFT7-mediated expansion in the frequency of CD44$^{int}$CD25⁻ DN thymocytes. Number represents the percentage in each gated region. (B) Increase in the number of total, DN4 and both CD44$^{int}$ and CD44$^{hi}$ DN1 in GIFT7-treated aged mice. Thymi were dissociated and analyzed by flow cytometry. Histogram represent mean number of cells+/−SD (n=6). (C) IL7Rα expression is primarily located in the DN1 CD44$^{hi}$ subset. Thymi derived from GIFT7-, IL7-, or untreated aged mice were dissociated and analyzed by surface expression of CD4, CD8, CD25, CD44, and CD127 (IL7Rα) by flow cytometry. Histogram represents IL7Rα expression in different subsets of DN thymocytes.

Regenerated $CD44^{int}$ DN Function as Progenitors in GIFT7-Driven Thymic Reconstitution Further analysis of the DN compartment shows that exogenous GIFT7 administration alters thymic composition in that $CD44^{int}CD25^-$ DN subset was significantly expanded in aged thyme (FIG. 12A). There is a 4-fold increase in the number of $CD44^{int}$ DN1 in addition to an expansion in total DN1 and DN4 subsets (FIG. 12B). This indicates that $CD44^{int}$ DN1 is the most responsive subset to pharmacologic IL7—hypersignalling despite lower expression of IL7Rα (FIG. 12C). This data indicates that $CD44^{int}$DN1 is the most responsive subset to IL7—mediated hypersignalling in vivo and is capable of partaking in T cell neogenesis.

GIFT7 Treatment Enhances Anti-CMV CTL Response in Aged Mice

Latent cytomegalovirus (CMV) reactivation frequently correlates with immune compromised state. Its clearance depends on functional T cell reconstitution in post bone marrow transplant (BMT) and sufficient naïve T cell output in the elderly. To analyze the effect of GIFT7 on acquired anti-viral immunity in aged mice, IL7-, $IL7^+GMCSF$-, GIFT7-, or PBSpreconditioned virus-naïve mice were challenged with a nonlethal dose of murine CMV (MCMV) 6 days post treatment. Mice were sacrificed 10 days after viral inoculation, and anti-MCMV T cells in the spleen were enumerated (FIG. 13A). viral-specific cytotoxic T lymphocyte (CTL) immunity was measured by MCMV-peptide MHC tetramer$^+$. Aged mice show relative reduced MCMVspecific CTL response. GIFT7 treatment significantly increased the frequency and number of MCMV-peptide MHC tetramer$^+$ CD8$^+$ T cells in the spleen (10.4±3.8 v.s. 2.9±1.4×10$^6$ for GIFT7 and untreated respectively, p<0.05) (FIGS. 13B,C, and D). This indicates that GITF7-mediated thymic stimulation in aged mice lead to enhanced thymic output and adaptive cellular immunity against a defined viral pathogen.

---

What is claimed:

1. A conjugate comprising a GM-CSF polypeptide and an IL-7 polypeptide, wherein the conjugate comprises the amino acid sequence of SEQ ID NO:1.

2. A pharmaceutical composition comprising the conjugate of claim 1, and a pharmaceutically acceptable excipient.

* * * * *

SEQUENCE LISTING

```
<160> NUMBER OF SEQ ID NOS: 4

<210> SEQ ID NO 1
<211> LENGTH: 290
<212> TYPE: PRT
<213> ORGANISM: Homo sapiens

<400> SEQUENCE: 1

Met Trp Leu Gln Asn Leu Leu Phe Leu Gly Ile Val Val Tyr Ser Leu
1               5                   10                  15

Ser Ala Pro Thr Arg Ser Pro Ile Thr Val Thr Arg Pro Trp Lys His
            20                  25                  30

Val Glu Ala Ile Lys Glu Ala Leu Asn Leu Leu Asp Asp Met Pro Val
        35                  40                  45

Thr Leu Asn Glu Glu Val Glu Val Val Ser Asn Glu Phe Ser Phe Lys
    50                  55                  60

Lys Leu Thr Cys Val Gln Thr Arg Leu Lys Ile Phe Glu Gln Gly Leu
65                  70                  75                  80

Arg Gly Asn Phe Thr Lys Leu Lys Gly Ala Leu Asn Met Thr Ala Ser
                85                  90                  95

Tyr Tyr Gln Thr Tyr Cys Pro Pro Thr Pro Glu Thr Asp Cys Glu Thr
            100                 105                 110
```

```
Gln Val Thr Thr Tyr Ala Asp Phe Ile Asp Ser Leu Lys Thr Phe Leu
        115                 120                 125

Thr Ser Pro Val Gly Gly Ala Asn Met Phe His Val Ser Phe Arg Tyr
130                 135                 140

Ile Phe Gly Ile Pro Pro Leu Leu Leu Val Leu Leu Pro Val Thr Ser
145                 150                 155                 160

Ser Glu Cys His Ile Lys Asp Lys Glu Gly Lys Ala Tyr Glu Ser Val
                165                 170                 175

Leu Met Ile Ser Ile Asp Glu Leu Asp Lys Met Thr Gly Thr Asp Ser
                180                 185                 190

Asn Cys Pro Asn Asn Glu Pro Asn Phe Phe Arg Lys His Val Cys Asp
                195                 200                 205

Asp Thr Lys Glu Ala Ala Phe Leu Asn Arg Ala Ala Arg Lys Leu Lys
        210                 215                 220

Gln Phe Leu Lys Met Asn Ile Ser Glu Glu Phe Asn Val His Leu Leu
225                 230                 235                 240

Thr Val Ser Gln Gly Thr Gln Thr Leu Val Asn Cys Thr Ser Lys Glu
                245                 250                 255

Glu Lys Asn Val Lys Glu Gln Lys Lys Asn Asp Ala Cys Phe Leu Lys
                260                 265                 270

Arg Leu Leu Arg Glu Ile Lys Thr Cys Trp Asn Lys Ile Leu Lys Gly
        275                 280                 285

Ser Ile
    290

<210> SEQ ID NO 2
<211> LENGTH: 325
<212> TYPE: PRT
<213> ORGANISM: Homo sapiens

<400> SEQUENCE: 2

Met Trp Leu Gln Ser Leu Leu Leu Leu Gly Thr Val Ala Cys Ser Ile
1               5                   10                  15

Ser Ala Pro Ala Arg Ser Pro Ser Pro Ser Thr Gln Pro Trp Glu His
                20                  25                  30

Val Asn Ala Ile Gln Glu Ala Arg Arg Leu Leu Asn Leu Ser Arg Asp
            35                  40                  45

Thr Ala Ala Glu Met Asn Glu Thr Val Glu Val Ile Ser Glu Met Phe
        50                  55                  60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
                85                  90                  95

Met Ala Ser His Tyr Lys Gln His Cys Pro Pro Thr Pro Glu Thr Ser
                100                 105                 110

Cys Ala Thr Gln Ile Ile Thr Phe Glu Ser Phe Lys Glu Asn Leu Lys
            115                 120                 125

Asp Phe Leu Leu Val Ile Pro Phe Asp Cys Trp Glu Pro Val Gln Glu
        130                 135                 140

Ser Pro Val Asn Met Phe His Val Ser Phe Arg Tyr Ile Phe Gly Leu
145                 150                 155                 160

Pro Pro Leu Ile Leu Val Leu Leu Pro Val Ala Ser Ser Asp Cys Asp
                165                 170                 175

Ile Glu Gly Lys Asp Gly Lys Gln Tyr Glu Ser Val Leu Met Val Ser
                180                 185                 190
```

```
Ile Asp Gln Leu Leu Asp Ser Met Lys Glu Ile Gly Ser Asn Cys Leu
            195                 200                 205

Asn Asn Glu Phe Asn Phe Phe Lys Arg His Ile Cys Asp Ala Asn Lys
210                 215                 220

Glu Gly Met Phe Leu Phe Arg Ala Ala Arg Lys Leu Arg Gln Phe Leu
225                 230                 235                 240

Lys Met Asn Ser Thr Gly Asp Phe Asp Leu His Leu Leu Lys Val Ser
            245                 250                 255

Glu Gly Thr Thr Ile Leu Leu Asn Cys Thr Gly Gln Val Lys Gly Arg
            260                 265                 270

Lys Pro Ala Ala Leu Gly Glu Ala Gln Pro Thr Lys Ser Leu Glu Glu
            275                 280                 285

Asn Lys Ser Leu Lys Glu Gln Lys Lys Leu Asn Asp Leu Cys Phe Leu
            290                 295                 300

Lys Arg Leu Leu Gln Glu Ile Lys Thr Cys Trp Asn Lys Ile Leu Met
305                 310                 315                 320

Gly Thr Lys Glu His
            325

<210> SEQ ID NO 3
<211> LENGTH: 978
<212> TYPE: PRT
<213> ORGANISM: Homo sapiens

<400> SEQUENCE: 3

Ala Thr Gly Thr Gly Gly Cys Thr Gly Cys Ala Gly Cys Gly Cys Cys
1               5                   10                  15

Thr Gly Cys Thr Gly Cys Thr Cys Thr Thr Gly Gly Gly Cys Ala Cys
            20                  25                  30

Thr Gly Thr Gly Gly Cys Cys Thr Gly Cys Ala Gly Cys Ala Thr Cys
            35                  40                  45

Thr Cys Thr Gly Cys Ala Cys Cys Cys Gly Cys Cys Gly Cys Thr
50                  55                  60

Cys Gly Cys Cys Ala Gly Cys Cys Cys Ala Gly Cys Ala Cys
65                  70                  75                  80

Gly Cys Ala Gly Cys Cys Thr Gly Gly Ala Gly Cys Ala Thr
            85                  90                  95

Gly Thr Gly Ala Ala Thr Gly Cys Cys Ala Cys Cys Ala Gly Gly
            100                 105                 110

Ala Gly Gly Cys Cys Cys Gly Gly Cys Gly Thr Cys Thr Cys Cys Thr
            115                 120                 125

Gly Ala Ala Cys Cys Thr Gly Ala Gly Thr Ala Gly Ala Gly Ala Cys
            130                 135                 140

Ala Cys Thr Gly Cys Thr Gly Cys Thr Gly Ala Gly Ala Thr Gly Ala
145                 150                 155                 160

Ala Thr Gly Ala Ala Cys Ala Gly Thr Ala Gly Ala Ala Gly Thr
            165                 170                 175

Cys Ala Thr Cys Thr Cys Ala Gly Ala Ala Thr Gly Thr Thr
            180                 185                 190

Gly Ala Cys Cys Thr Cys Cys Ala Gly Gly Ala Gly Cys Cys Gly Ala
            195                 200                 205

Cys Cys Thr Gly Cys Cys Thr Ala Cys Ala Gly Ala Cys Cys Cys Gly
            210                 215                 220
```

-continued

```
Cys Cys Thr Gly Gly Ala Gly Cys Thr Gly Thr Ala Cys Ala Ala Gly
225                 230                 235                 240
Cys Ala Gly Gly Gly Cys Cys Thr Gly Cys Gly Gly Gly Cys Ala
            245                 250                 255
Gly Cys Cys Thr Cys Ala Cys Cys Ala Ala Gly Cys Thr Cys Ala Ala
            260                 265                 270
Gly Gly Gly Cys Cys Cys Cys Thr Gly Ala Cys Cys Ala Thr Gly
        275                 280                 285
Ala Thr Gly Gly Cys Cys Ala Gly Cys Cys Ala Thr Ala Cys Ala
        290                 295                 300
Ala Gly Cys Ala Gly Cys Ala Cys Thr Gly Cys Cys Thr Cys Cys
305                 310                 315                 320
Ala Ala Cys Cys Cys Cys Gly Gly Ala Ala Cys Thr Thr Cys Cys
            325                 330                 335
Thr Gly Thr Gly Cys Ala Ala Cys Cys Cys Ala Gly Ala Thr Thr Ala
            340                 345                 350
Thr Cys Ala Cys Cys Thr Thr Gly Ala Ala Ala Gly Thr Thr Thr
        355                 360                 365
Cys Ala Ala Ala Gly Ala Gly Ala Ala Cys Cys Thr Gly Ala Ala Gly
        370                 375                 380
Gly Ala Cys Thr Thr Thr Cys Thr Gly Cys Thr Thr Gly Thr Cys Ala
385                 390                 395                 400
Thr Cys Cys Cys Cys Thr Thr Thr Gly Ala Cys Thr Gly Cys Thr Gly
            405                 410                 415
Gly Gly Ala Gly Cys Cys Ala Gly Thr Cys Cys Ala Gly Gly Ala Gly
            420                 425                 430
Thr Cys Ala Cys Cys Gly Gly Thr Cys Ala Ala Cys Ala Thr Gly Thr
            435                 440                 445
Thr Cys Cys Ala Thr Gly Thr Thr Thr Cys Thr Thr Thr Ala Ala Gly
        450                 455                 460
Gly Thr Ala Thr Ala Thr Cys Thr Thr Thr Gly Gly Ala Cys Thr Thr
465                 470                 475                 480
Cys Cys Thr Cys Cys Cys Cys Thr Gly Ala Thr Cys Cys Thr Thr Gly
            485                 490                 495
Thr Thr Cys Thr Gly Thr Thr Gly Cys Cys Ala Gly Thr Ala Gly Cys
            500                 505                 510
Ala Thr Cys Ala Thr Cys Thr Gly Ala Thr Gly Thr Gly Ala Thr
        515                 520                 525
Ala Thr Thr Gly Ala Ala Gly Gly Thr Ala Ala Ala Gly Ala Thr Gly
        530                 535                 540
Gly Cys Ala Ala Ala Cys Ala Ala Thr Ala Thr Gly Ala Gly Ala Gly
545                 550                 555                 560
Thr Gly Thr Thr Cys Thr Ala Ala Thr Gly Gly Thr Cys Ala Gly Cys
            565                 570                 575
Ala Thr Cys Gly Ala Thr Cys Ala Ala Thr Thr Ala Thr Thr Gly Gly
            580                 585                 590
Ala Cys Ala Gly Cys Ala Thr Gly Ala Ala Gly Ala Ala Ala Thr
        595                 600                 605
Thr Gly Gly Thr Ala Gly Cys Ala Ala Thr Gly Cys Cys Thr Gly
        610                 615                 620
Ala Ala Thr Ala Ala Thr Gly Ala Ala Thr Thr Thr Ala Ala Cys Thr
625                 630                 635                 640
```

Thr Thr Thr Thr Thr Ala Ala Ala Gly Ala Cys Ala Thr Ala Thr
                    645                 650                 655

Cys Thr Gly Thr Gly Ala Thr Gly Cys Thr Ala Ala Thr Ala Ala Gly
                660                 665                 670

Gly Ala Ala Gly Gly Thr Ala Thr Gly Thr Thr Thr Thr Ala Thr
                675                 680                 685

Thr Cys Cys Gly Thr Gly Cys Thr Gly Thr Cys Gly Cys Ala Ala
                690                 695                 700

Gly Thr Thr Gly Ala Gly Gly Cys Ala Ala Thr Thr Cys Thr Thr
705                 710                 715                 720

Ala Ala Ala Ala Thr Gly Ala Ala Thr Ala Gly Cys Ala Cys Thr Gly
                725                 730                 735

Gly Thr Gly Ala Thr Thr Thr Gly Ala Thr Cys Thr Cys Cys Ala
                740                 745                 750

Cys Thr Thr Ala Thr Ala Ala Ala Gly Thr Thr Thr Cys Ala
                755                 760                 765

Gly Ala Ala Gly Gly Cys Ala Cys Ala Ala Cys Ala Thr Ala Cys
                770                 775                 780

Thr Gly Thr Thr Gly Ala Ala Cys Thr Gly Cys Ala Cys Thr Gly Gly
785                 790                 795                 800

Cys Cys Ala Gly Gly Thr Thr Ala Ala Gly Gly Ala Ala Gly Ala
                805                 810                 815

Ala Ala Ala Cys Cys Ala Gly Cys Thr Gly Cys Cys Cys Thr Gly Gly
                820                 825                 830

Gly Thr Gly Ala Ala Gly Cys Cys Cys Ala Ala Cys Cys Ala Ala Cys
                835                 840                 845

Ala Ala Ala Gly Ala Gly Thr Thr Thr Gly Gly Ala Ala Gly Ala Ala
                850                 855                 860

Ala Ala Thr Ala Ala Ala Thr Cys Thr Thr Thr Ala Ala Gly Gly
865                 870                 875                 880

Ala Ala Cys Ala Gly Ala Ala Ala Ala Ala Cys Thr Gly Ala Ala
                885                 890                 895

Thr Gly Ala Cys Thr Thr Gly Thr Gly Thr Thr Thr Cys Cys Thr Ala
                900                 905                 910

Ala Ala Gly Ala Gly Ala Cys Thr Ala Thr Thr Ala Cys Ala Ala Gly
                915                 920                 925

Ala Gly Ala Thr Ala Ala Ala Ala Cys Thr Thr Gly Thr Thr Gly
                930                 935                 940

Gly Ala Ala Thr Ala Ala Ala Thr Thr Thr Thr Gly Ala Thr Gly
945                 950                 955                 960

Gly Gly Cys Ala Cys Thr Ala Ala Ala Gly Ala Ala Cys Ala Cys Thr
                965                 970                 975

Gly Ala

<210> SEQ ID NO 4
<211> LENGTH: 873
<212> TYPE: PRT
<213> ORGANISM: Homo sapiens

<400> SEQUENCE: 4

Ala Thr Gly Thr Gly Gly Cys Thr Gly Cys Ala Gly Ala Ala Thr Thr
1               5                   10                  15

Thr Ala Cys Thr Thr Thr Thr Cys Cys Thr Gly Gly Cys Ala Thr
                20                  25                  30

-continued

```
Thr Gly Thr Gly Gly Thr Cys Thr Ala Cys Ala Gly Cys Cys Thr Cys
        35                  40                  45

Thr Cys Ala Gly Cys Ala Cys Cys Cys Ala Cys Cys Cys Gly Cys Thr
    50                  55                  60

Cys Ala Cys Cys Cys Ala Thr Cys Ala Cys Thr Gly Thr Cys Ala Cys
65                  70                  75                  80

Cys Cys Gly Gly Cys Cys Thr Thr Gly Gly Ala Ala Gly Cys Ala Thr
                85                  90                  95

Gly Thr Ala Gly Ala Gly Gly Cys Cys Ala Thr Cys Ala Ala Ala Gly
            100                 105                 110

Ala Ala Gly Cys Cys Cys Thr Gly Ala Ala Cys Cys Thr Cys Cys Thr
        115                 120                 125

Gly Gly Ala Thr Gly Ala Cys Ala Thr Gly Cys Cys Thr Gly Thr Cys
    130                 135                 140

Ala Cys Gly Thr Thr Gly Ala Ala Thr Gly Ala Ala Gly Ala Gly Gly
145                 150                 155                 160

Thr Ala Gly Ala Ala Gly Thr Cys Gly Thr Cys Thr Cys Thr Ala Ala
                165                 170                 175

Cys Gly Ala Gly Thr Thr Cys Thr Cys Cys Thr Thr Cys Ala Ala Gly
            180                 185                 190

Ala Ala Gly Cys Thr Ala Ala Cys Ala Thr Gly Thr Gly Thr Gly Cys
        195                 200                 205

Ala Gly Ala Cys Cys Cys Gly Cys Cys Thr Gly Ala Ala Gly Ala Thr
    210                 215                 220

Ala Thr Thr Cys Gly Ala Gly Cys Ala Gly Gly Gly Thr Cys Thr Ala
225                 230                 235                 240

Cys Gly Gly Gly Gly Cys Ala Ala Thr Thr Thr Cys Ala Cys Cys Ala
                245                 250                 255

Ala Ala Cys Thr Cys Ala Ala Gly Gly Gly Cys Gly Cys Cys Thr Thr
            260                 265                 270

Gly Ala Ala Cys Ala Thr Gly Ala Cys Ala Gly Cys Cys Ala Gly Cys
        275                 280                 285

Thr Ala Cys Thr Ala Cys Cys Ala Gly Ala Cys Ala Thr Ala Cys Thr
    290                 295                 300

Gly Cys Cys Cys Cys Cys Cys Ala Ala Cys Thr Cys Cys Gly Gly Ala
305                 310                 315                 320

Ala Ala Cys Gly Gly Ala Cys Thr Gly Thr Gly Ala Ala Ala Cys Ala
                325                 330                 335

Cys Ala Ala Gly Thr Thr Ala Cys Cys Ala Cys Cys Thr Ala Thr Gly
            340                 345                 350

Cys Gly Gly Ala Thr Thr Thr Cys Ala Thr Ala Gly Ala Cys Ala Gly
        355                 360                 365

Cys Cys Thr Thr Ala Ala Ala Ala Cys Cys Thr Thr Thr Cys Thr Gly
    370                 375                 380

Ala Cys Thr Thr Cys Ala Cys Cys Gly Gly Thr Ala Gly Gly Ala Gly
385                 390                 395                 400

Gly Gly Gly Cys Cys Ala Ala Cys Ala Thr Gly Thr Thr Cys Cys Ala
                405                 410                 415

Thr Gly Thr Thr Thr Cys Thr Thr Thr Thr Ala Gly Ala Thr Ala Thr
            420                 425                 430

Ala Thr Cys Thr Thr Thr Gly Gly Ala Ala Thr Thr Cys Cys Thr Cys
        435                 440                 445
```

-continued

```
Cys Ala Cys Thr Gly Ala Thr Cys Cys Thr Thr Gly Thr Thr Cys Thr
    450                 455                 460

Gly Cys Thr Gly Cys Cys Thr Gly Thr Cys Ala Cys Ala Thr Cys Ala
465                 470                 475                 480

Thr Cys Thr Gly Ala Gly Thr Gly Cys Cys Ala Cys Ala Thr Thr Ala
                485                 490                 495

Ala Ala Gly Ala Cys Ala Ala Ala Gly Ala Ala Gly Gly Thr Ala Ala
            500                 505                 510

Ala Gly Cys Ala Thr Ala Thr Gly Ala Gly Ala Gly Thr Gly Thr Ala
        515                 520                 525

Cys Thr Gly Ala Thr Gly Ala Thr Cys Ala Gly Cys Ala Thr Cys Gly
    530                 535                 540

Ala Thr Gly Ala Ala Thr Thr Gly Gly Ala Cys Ala Ala Ala Ala Thr
545                 550                 555                 560

Gly Ala Cys Ala Gly Gly Ala Ala Cys Thr Gly Ala Thr Ala Gly Thr
                565                 570                 575

Ala Ala Thr Thr Gly Cys Cys Cys Gly Ala Ala Thr Ala Ala Thr Gly
            580                 585                 590

Ala Ala Cys Cys Ala Ala Ala Cys Thr Thr Thr Thr Thr Thr Ala Gly
        595                 600                 605

Ala Ala Ala Ala Cys Ala Thr Gly Thr Ala Thr Gly Thr Gly Ala Thr
    610                 615                 620

Gly Ala Thr Ala Cys Ala Ala Ala Gly Gly Ala Ala Gly Cys Thr Gly
625                 630                 635                 640

Cys Thr Thr Thr Thr Cys Thr Ala Ala Ala Thr Cys Gly Thr Gly Cys
                645                 650                 655

Thr Gly Cys Thr Cys Gly Cys Ala Ala Gly Thr Thr Gly Ala Ala Gly
            660                 665                 670

Cys Ala Ala Thr Thr Thr Cys Thr Thr Ala Ala Ala Ala Thr Gly Ala
        675                 680                 685

Ala Thr Ala Thr Cys Ala Gly Thr Gly Ala Ala Gly Ala Ala Thr Thr
    690                 695                 700

Cys Ala Ala Thr Gly Thr Cys Cys Ala Cys Thr Thr Ala Cys Thr Ala
705                 710                 715                 720

Ala Cys Ala Gly Thr Ala Thr Cys Ala Cys Ala Ala Gly Gly Cys Ala
                725                 730                 735

Cys Ala Cys Ala Ala Ala Cys Ala Cys Thr Gly Gly Thr Gly Ala Ala
            740                 745                 750

Cys Thr Gly Cys Ala Cys Ala Ala Gly Thr Ala Ala Gly Gly Ala Ala
        755                 760                 765

Gly Ala Ala Ala Ala Ala Ala Ala Cys Gly Thr Ala Ala Ala Gly Gly
    770                 775                 780

Ala Ala Cys Ala Gly Ala Ala Ala Ala Ala Gly Ala Ala Thr Gly Ala
785                 790                 795                 800

Thr Gly Cys Ala Thr Gly Thr Thr Thr Cys Cys Thr Ala Ala Ala Gly
                805                 810                 815

Ala Gly Ala Cys Thr Ala Cys Thr Gly Ala Gly Ala Gly Ala Ala Ala
            820                 825                 830

Thr Ala Ala Ala Ala Ala Cys Thr Thr Gly Thr Thr Gly Gly Ala Ala
        835                 840                 845

Thr Ala Ala Ala Ala Thr Thr Thr Thr Gly Ala Ala Gly Gly Gly Cys
    850                 855                 860
```

-continued

```
Ala Gly Thr Ala Thr Ala Thr Ala Ala
865                 870
```